United States Patent
Eklund

(10) Patent No.: US 9,782,515 B2
(45) Date of Patent: Oct. 10, 2017

(54) ORAL TISSUE REGENERATION AND REPAIR

(75) Inventor: Dario C. Eklund, Canton, MA (US)

(73) Assignee: Organogenesis, Inc., Canton, MA (US)

( * ) Notice: Subject to any disclaimer, the term of this patent is extended or adjusted under 35 U.S.C. 154(b) by 833 days.

(21) Appl. No.: 12/282,326

(22) PCT Filed: Mar. 5, 2007

(86) PCT No.: PCT/US2007/063301
§ 371 (c)(1), (2), (4) Date: Jan. 20, 2009

(87) PCT Pub. No.: WO2007/103865
PCT Pub. Date: Sep. 13, 2007

(65) Prior Publication Data
US 2009/0130068 A1    May 21, 2009

Related U.S. Application Data

(60) Provisional application No. 60/779,050, filed on Mar. 3, 2006.

(51) Int. Cl.
| | |
|---|---|
| *A61K 35/12* | (2015.01) |
| *A61L 27/36* | (2006.01) |
| *A61K 35/33* | (2015.01) |
| *A61L 27/38* | (2006.01) |
| *C12N 5/077* | (2010.01) |
| *C12N 5/071* | (2010.01) |

(52) U.S. Cl.
CPC .......... *A61L 27/3641* (2013.01); *A61K 35/33* (2013.01); *A61L 27/3633* (2013.01); *A61L 27/3804* (2013.01); *A61L 27/3813* (2013.01); *A61L 27/3839* (2013.01); *A61L 27/3891* (2013.01); *C12N 5/0656* (2013.01); *C12N 5/0698* (2013.01); *A61K 35/12* (2013.01); *C12N 2500/25* (2013.01); *C12N 2500/32* (2013.01); *C12N 2500/36* (2013.01); *C12N 2500/38* (2013.01); *C12N 2500/40* (2013.01); *C12N 2500/50* (2013.01); *C12N 2500/90* (2013.01); *C12N 2501/11* (2013.01); *C12N 2501/39* (2013.01); *C12N 2501/392* (2013.01); *C12N 2501/395* (2013.01); *C12N 2502/094* (2013.01); *C12N 2502/1323* (2013.01)

(58) Field of Classification Search
CPC .... A61K 35/33; A61K 35/12; C12N 2501/39; C12N 2500/90; C12N 2500/36; C12N 2500/38; C12N 2502/1323; C12N 2501/395; C12N 5/0656; C12N 5/0698; C12N 2500/25; C12N 2500/32; C12N 2501/11; C12N 2501/392; C12N 2500/50; C12N 2500/40; C12N 2502/094; A61L 27/3633; A61L 27/3813; A61L 27/3891; A61L 27/3641; A61L 27/3839; A61L 27/3804
See application file for complete search history.

(56) References Cited

U.S. PATENT DOCUMENTS

| | | | |
|---|---|---|---|
| 4,485,096 A | 11/1984 | Bell | |
| 5,536,656 A | 7/1996 | Kemp et al. | |
| 6,179,872 B1 * | 1/2001 | Bell et al. | 623/11.11 |
| 2002/0172705 A1 * | 11/2002 | Murphy | C12N 5/0698 424/422 |
| 2003/0143207 A1 * | 7/2003 | Livesey | A61K 35/36 424/93.7 |
| 2005/0053585 A1 * | 3/2005 | Black | A61L 27/3633 424/93.7 |
| 2006/0039896 A1 * | 2/2006 | Kleinsek et al. | 424/93.7 |
| 2006/0177492 A1 * | 8/2006 | Yunoki | A61K 9/06 424/445 |
| 2008/0118474 A1 * | 5/2008 | Okano et al. | 424/93.7 |

FOREIGN PATENT DOCUMENTS

| | | |
|---|---|---|
| EP | 1 748 064 | 1/2007 |
| WO | WO-83/04177 A1 | 12/1983 |
| WO | WO-00/29553 | 5/2000 |
| WO | WO-03/052084 | 6/2003 |
| WO | WO-2005/103233 | 11/2005 |

OTHER PUBLICATIONS

Aframian et al. Characterization of murine autologous salivary gland graft cells: a model for use with an artificial salivary gland, Tissue Eng. 10(5-6):914-20, 2004.*
Lallier et al., The putative collagen-binding peptide P-15 promotes fibroblast attachment to root shavings but not hydroxyapatite, J. Periodontol. 74(4):458-67, 2003.*
McGuire and Nunn. "Evaluation of the Safety and Efficacy of Periodontal Applications of a Living Tissue-Engineered Human Fibroblast-Derived Dermal Substitute. I. Comparison to the Gingival Autograft: A Randomized Controlled Pilot Study." Journal of Periodontology (Jun. 2005);76(6): pp. 867-880.*
Buurma et al., "Transplantation of human pulpal and gingival fibroblasts attached to synthetic scaffolds," Eur. J. Oral Sci., 107:282-289 (1999).
Bodner et al., "Autologous Cultured Musosel Graft to Cover Large Intraoral Muscosal Defects: A Clinical Study," J. Oral. Maxillofac. Surg.. 61:169-173 (2003).

(Continued)

*Primary Examiner* — Titilayo Moloye
(74) *Attorney, Agent, or Firm* — Foley Hoag LLP; Philip S. Choi

(57) ABSTRACT

A method for treating an oral condition of a subject by grafting cultured tissue constructs to the oral tissue. The cultured tissue constructs comprise cultured cells and endogenously produced extracellular matrix components without the requirement of exogenous matrix components or network support or scaffold members. Some tissue constructs of the invention are comprised of multiple cell layers or more than one cell type. The tissue constructs of the invention have morphological features and functions similar to tissues their cells are derived and their strength makes them easily handleable. Preferred cultured tissue constructs of the invention comprise cells derived from human tissue.

1 Claim, 11 Drawing Sheets

(56) References Cited

OTHER PUBLICATIONS

Imaizumi et al., "Cultured Mucosal Cell Sheet with a Double Layer of Keratinocytes and Fibroblasts o a Collagen Membrane," Tissue Engineering, 5/6:657-664 (2004).
Izumi et al., "Skin and oral mucosal substitutes," Oral Maxillofacial Surg. Clin. N. Am., 14:61-71 (2002).
McGuire et al., "Evaluation of the Safety and Efficacy of Periodontal Applications of a Living Tissue-Engineered Human Fibroblast-Derived Dermal Substitute. I. Comparison to the Gingival Autograft: A Randomized Controlled Pilot Study," J. Peridontal, 76:867-880 (2005).
Moriyama et al., "Development of Composite Cultured Oral Mucosa Utilizing Collagen Sponge Matrix and Contracted Collagen Gel: A Preliminary Study for Clinical Applications," Tissue Engineering, 7(4):415-427 (2001).
Pouliot et al., "Reconstructed Human Skin Produced in Vitro and Grafted on Athymic Mice," Transplantation, 73(11):1751-1757 (2002).
Raghoebar et al., "Use of Cultured Mucosal Grafts to Cover Defects Caused by Vestibuloplasty: An In Vivo Study," J. Oral Maxillofac. Surg., 53:872-878 (1995).
International Search Report dated Sep. 17, 2008 from PCT/US2007/063301.
Supplementary European Search Report dated Mar. 24, 2010 from EP 07 75 7907.
McGuire et al., "A Pilot Study to Evaluate a Tissue-Engineered Bilayered Cell Therapy as an Alternative to Tissue from the Palate," J Periodontol, 79(10): 1847-1856 (2008).

\* cited by examiner

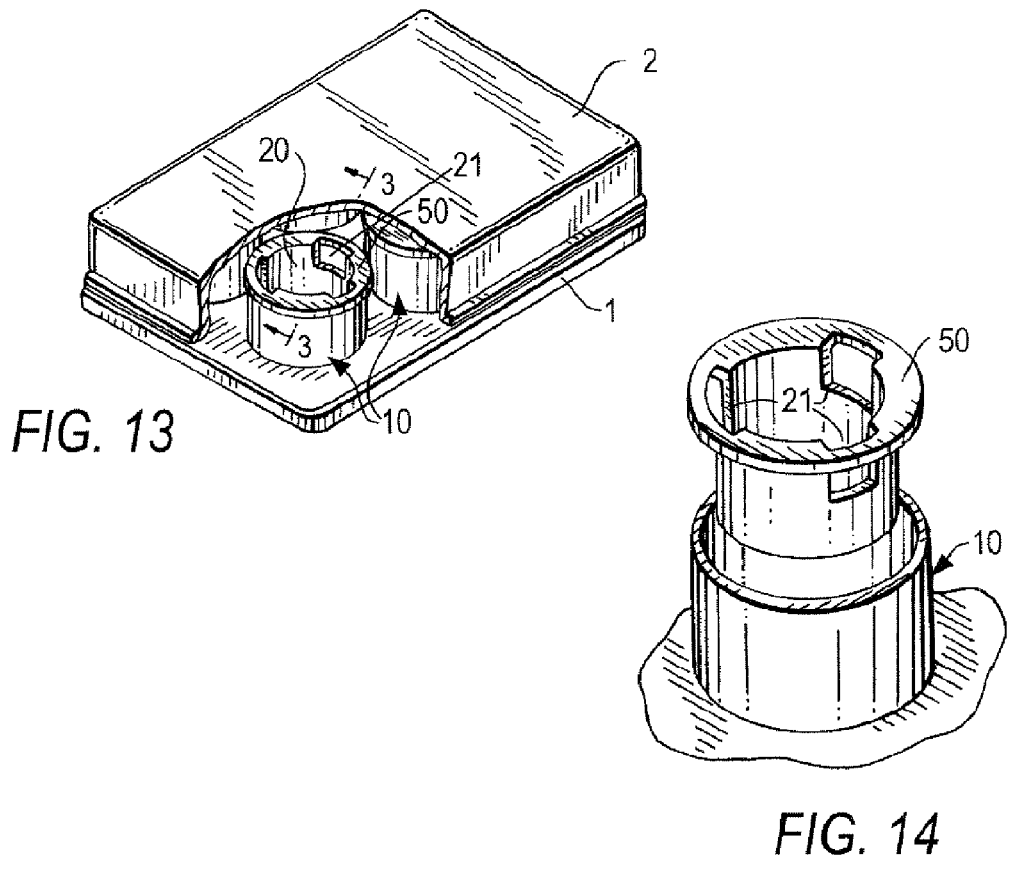
FIG. 13
FIG. 14
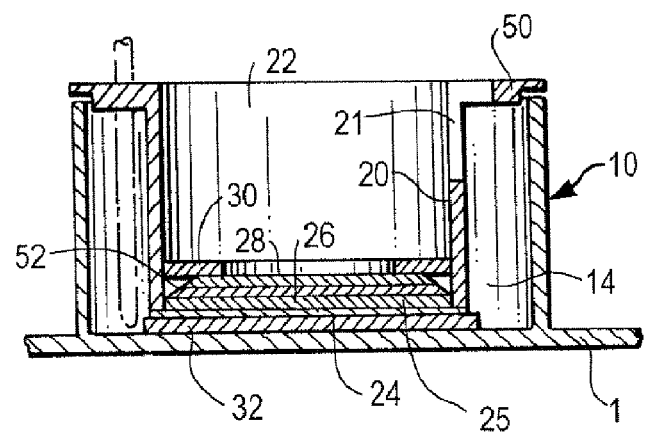
FIG. 15

ORAL TISSUE REGENERATION AND REPAIR

FIELD OF THE INVENTION

The invention is in the field of tissue engineering, particularly for the use of a cultured tissue construct for oral tissue regeneration and repair.

BACKGROUND OF THE INVENTION

The field of tissue engineering combines bioengineering methods with the principles of life sciences to understand the structural and functional relationships in normal and pathological mammalian tissues. The goal of tissue engineering is the development and ultimate application of biological substitutes to restore, maintain, or improve tissue functions. Thus, through tissue engineering, it is possible to design and manufacture a bioengineered tissue in a laboratory. Bioengineered tissues can include cells that are usually associated with a native mammalian or human tissues and synthetic or exogenous matrix scaffolds.

The new bioengineered tissue must be functional when grafted onto a host, and be permanently incorporated within the host's body or progressively bioremodeled by cells from the recipient host patient. Fabrication of a tissue equivalent without a support member or scaffold leads to scientific challenges in creating the new bioengineered tissue.

Most of the oral soft tissue grafting procedures are done using autologous tissue from the palate. Although this might work very well in some of the procedures, it has the disadvantage of requiring the creation of a "donor site" that can be quite painful for patients. This additional donor site also provides limited tissue, meaning that only few teeth can be treated at one time. This can result in the need for multiple surgeries or the dentist only treating the "worst teeth" even though there may be several left untreated that could also have benefited from a grafting procedure.

SUMMARY OF THE INVENTION

The invention is directed to methods for treating an oral condition of a subject by grafting a cultured tissue construct to the oral tissue of the subject.

The cultured tissue constructs of the invention comprise cultured cells and endogenously produced extracellular matrix components without the requirement of exogenous matrix components or network support or scaffold members. The invention can thus advantageously be made entirely from human cells, and human matrix components produced by those cells for use in humans The graft of cultured tissue constructs comprises fibroblasts producing extracellular matrix components without the addition of either exogenous matrix components, network support, or scaffold members.

The cultured tissue constructs comprise fibroblasts producing extracellular matrix components in a defined medium system and/or without the use of undefined or non-human-derived biological components, such as bovine serum or organ extracts.

Further, cultured tissue constructs can be made by serial seeding cell of different types which produce a cultured tissue construct that mimics the cell composition and tissue structures of native tissues. Specifically, this cultured tissue construct comprises at least a layer of epithelial cells applied over a layer of cultured fibroblast cells. Still further, the tissue construct is produced and self-assembled by cultured cells without the need for scaffold support or the addition of exogenous extracellular matrix components.

The cultured tissue construct graft of this invention also comprises a gel mixture of a collagen solution with a contractile agent.

Further, the cultured tissue construct grafts of this invention comprise a layer of collagen gel comprising collagen with a contractile agent disposed over a layer of an acellular collagen gel.

In yet another embodiment of the present invention, epithelial cells are added to the layer comprising the collagen gel and the contractile agent.

The strength characteristics of the tissue constructs make it handleable for it to be easily and peelably removed from the culture apparatus in which it is formed and directly transplanted without the need for any support or carrier in clinical or testing applications. The tissue constructs of the invention are indicated for treatment of patients with oral tissue affections such as recessed oral gingiva, loss of interdental papilla, alveolar deficiency, failing oral implant, dental furcation defects and patients in need of tissue reconstruction following maxillofacial tumor resections.

DESCRIPTION OF THE FIGURES

FIG. 13 is an isometric view, partially broken away, of one apparatus according to the present invention.

FIG. 14 is an exploded isometric view of the apparatus shown in FIG. 13.

FIG. 15 is section along 3-3 through the apparatus shown in FIG. 13.

DETAILED DESCRIPTION OF THE INVENTION

Figure 1:
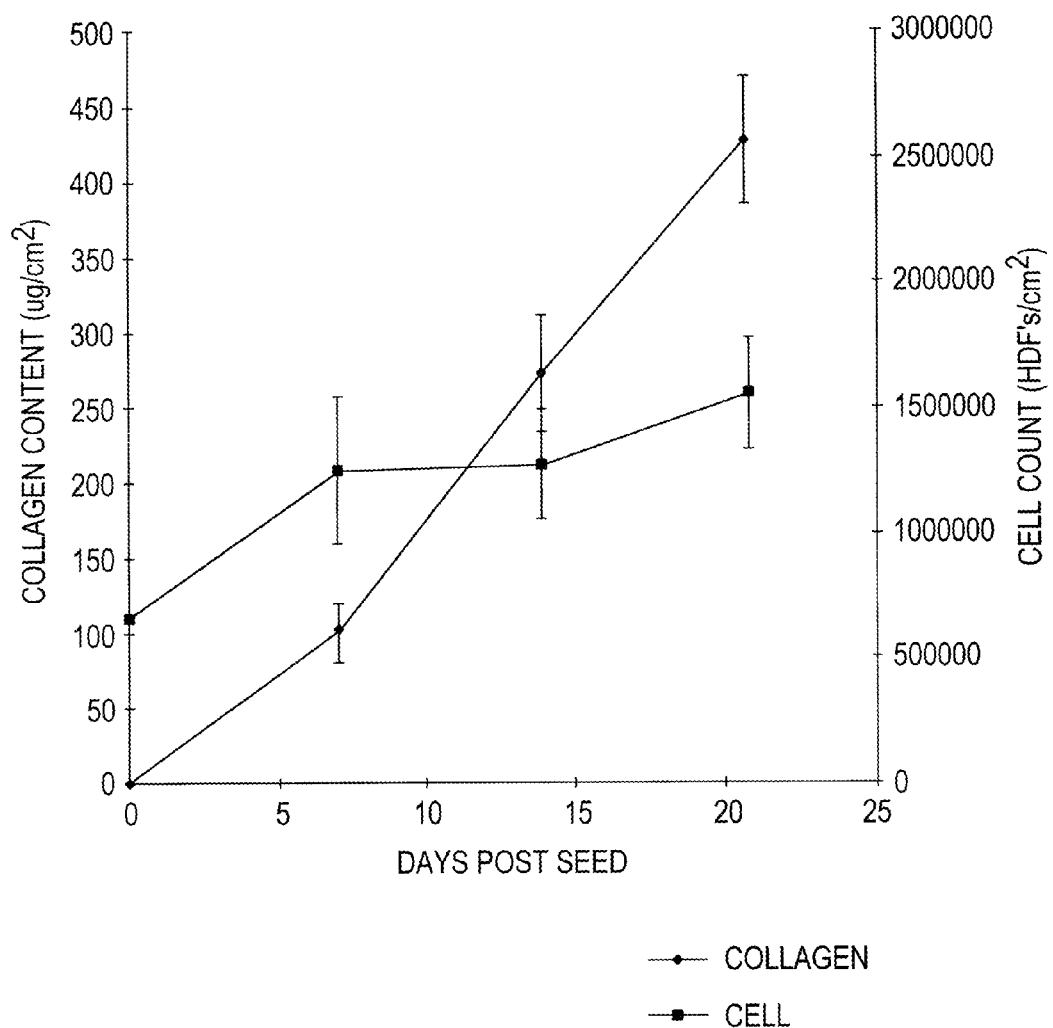
FIG. 1 is a graph depicting the increase in collagen concentration as determined by hydroxyproline assay as compared to the cell number in the human neonatal foreskin cell derived dermal construct described in Example 1.

The invention is directed to methods for treating an oral condition of a subject by grafting a cultured tissue construct.

It should be noted that "cultured tissue construct," "engineered living tissue," "cell-matrix construct," "cell-matrix layer," "skin equivalent," "living tissue" and "living connecting tissue" may be used interchangeably as embodiments of the cultured tissue constructs of the present invention.

Heretofore, current engineered living tissue constructs are not completely cell assembled and must rely on either the addition or incorporation of exogenous matrix components or synthetic members for structure or support, or both.

The bioengineered tissue constructs described herein exhibit many of the native features of the tissue from which their cells are derived. The tissue constructs thus produced can be used for treating an oral condition of a patient One preferred embodiment is a cell-matrix construct comprising a first cell type and endogenously produced extracellular matrix wherein the first cell type is capable of synthesizing and secreting extracellular matrix to produce the cell-matrix construct.

Another preferred embodiment is a bilayer construct comprising a first cell type and endogenously produced extracellular matrix and a layer of cells of a second type disposed thereon or within the cell-matrix construct formed by the first cell type.

A more preferred embodiment is a cell-matrix construct comprising fibroblasts, such as those derived from dermis, to form a cultured dermal construct.

Another more preferred embodiment is a cell-matrix construct comprising fibroblasts, such as those derived from dermis, to form a cultured dermal construct with a layer of keratinocytes cultured thereon to form an epidermal layer to result in a cultured bilayer skin construct. The cultured skin constructs of the invention express many physical, morphological, and biochemical features of native skin.

In an even more preferred embodiment, the cell-matrix construct is a tissue construct that is similar to the dermal layer of skin, a human dermal construct, that is formed in a defined system comprising human-derived cells utilizing no chemically undefined components during its culture.

In the most preferred embodiment, the tissue constructs of the invention are fabricated in a chemically defined system comprising human-derived cells but no chemically undefined or non-human biological components or cells.

In another embodiment of this invention, the cultured tissue constructs comprise a gel mixture comprising a collagen solution and a contractile agent.

In the preferred embodiment of the invention, the cultured tissue constructs comprise a first layer comprising an acellular collagen gel and a second layer disposed on the first layer, wherein the second layer comprises a second collagen gel containing collagen and a contractile agent. In a even more preferred embodiment of the invention, the second layer of collagen with a contractile agent is seeded with keratinocyte cells.

A: Applications for the Cultured Tissue Constructs:

The culture tissue construct of the invention may be applied for treating oral conditions such as recessed oral gingival, loss of interdental papilla, alveolar ridge deficiency, consequences of a failed oral implant or of a maxillofacial tumor recession.

It is generally agreed that a functional zone of attached gingiva around each tooth is necessary for health. In the absence of this tissue, gingival recession frequently occurs, resulting in the loss of a portion of the cortical plate creating a worse prognosis for the tooth. In addition, the mucosa facial to the teeth without a functional zone of attached gingiva is often times found to be inflamed despite the subject's good homecare. This inflammation has the potential to cause bone loss around the tooth.

Since the late 1960s this type of problem has routinely been corrected by a free autogenous graft. The mucosa is removed facial to the tooth in question and keratinized tissue is harvested from the palate and sutured to the graft bed. Initially the graft is supported by a plasmotic circulation and later is revascularized from the surrounding bed. The success of this type of graft verges on 100%. There is, however, a strong desire by most subjects to try to identify a donor material that could be used instead of the palatal tissue. This, of course, would reduce the number of surgical sites necessary for this procedure by one-half. A number of substitute donor materials have been used over the years. Freeze-dried cadaver skin has been used in the past and recently an acellular dermal graft has been used as a donor material. Although extremely remote, the potential infection risk associated with these types of dermal materials (primarily AIDS and hepatitis) serves as a relative deterrent to their use. In addition to that, the final esthetic outcome of grafts utilizing this donor material is usually less than ideal.

B: Culture Tissue Constructs Comprising a Structural Layer of at Least One Type of Extracellular Layer-Producing Cells with Endogenously Produced Extracellular Matrix One preferred embodiment of the invention comprises a structural layer of at least one type of extracellular matrix-producing cells and endogenously produced extracellular matrix components, more simply termed "matrix", wherein the matrix is completely cell-synthesized and assembled by culturing the cells. This layer is herein termed a "cell-matrix construct" or a "cell-matrix layer" because the cells secrete and contain themselves within and through their matrix. As disclosed in copending U.S. patent application Ser. No. 09/523,809, filed Mar. 3, 200, incorporated herein by reference in its entirety, the cultured tissue constructs do not require, thus do not include, exogenous matrix components, that is, matrix components not produced by the cultured cells but introduced by other means. In a more preferred embodiment, the cell-matrix construct produced by human dermal fibroblasts is shown to have a predominant concentration of collagen similar to native skin. As evidenced by electron microscopy, the matrix is fibrous in nature comprising collagen that exhibits the quarter-staggered 67 nm banding pattern, as well as packing organization of fibrils and fibril bundles similar to native collagen.

Delayed reduction SDS-PAGE has detected the presence of both type I and type III collagen in these constructs, the predominant collagen types found in native human skin. Using standard immunohistochemistry (IHC) techniques, the dermal cell-matrix construct stains positively for decorin, a dermatan sulfate proteoglycan known to be associated with collagen fibrils and believed to regulate fibril diameter in vivo. Decorin can also be visualized in the construct with TEM. The produced tissue also stains positive for tenascin, an extracellular matrix glycoprotein found, for example, in mesenchyme or tissues under repair. Much like tissue under repair in vivo, the tissue produced in culture has been shown to increase its ratio of type I to type III collagen as the matrix is formed.

While not wishing to be bound by theory, it is believed that the cells fill in the open space between them quickly with a loose matrix analogous to granulation tissue comprised of mostly type III collagen and fibronectin, and then remodel this loose matrix with a denser matrix comprised of mostly type I collagen. The produced cell-matrix has been shown to contain glycosaminoglycans (GAG), such as hyaluronic acid (HA); fibronectin; proteoglycans besides decorin such as biglycan and versican; and, a profile of sulfated glycosaminoglycans such as di-hyaluronic acid; di-chondroitin-O-sulfate; di-chondroitin-4-sulfate; di-chondroitin-6-sulfate; di-chondroitin-4,6-sulfate; di-chondroitin-4-sulfate-UA-2S; and di-chondroitin-6-sulfate-UA-2S. These structural and biochemical features exhibit themselves as the construct develops in culture and are distinctively evident when the construct approaches its final form. The presence of these components in fully formed cultured dermal cell-matrix construct indicates that the construct has structural and biochemical features approaching that of normal dermis.

While the aforementioned list is a list of biochemical and structural features a cultured cell-matrix construct formed from dermal fibroblasts, it should be recognized that cultured cell-matrix constructs formed from other types of fibroblasts will produce many of these features and others phenotypic for tissue type from which they originated. In some cases, fibroblasts can be induced to express non-phenotypic components by either chemical exposure or contact, physical stresses, or by transgenic means.

Another preferred embodiment of the invention is a cell-matrix layer having second layer of cells disposed thereon. The second layer of cells is cultured on the cell-matrix layer to form a bioengineered bilayered tissue construct. In a more preferred embodiment, the cells of the second layer are of epithelial origin. In the most preferred embodiment, the second layer comprises cultured human keratinocytes that together with a first cell-matrix layer, a cell-matrix construct formed from dermal fibroblasts and endogenous matrix to form a dermal layer, comprise a living skin construct. When fully formed, the epidermal layer is a multilayered, stratified, and well-differentiated layer of keratinocytes that exhibit a basal layer, a suprabasal layer, a granular layer and a stratum corneum. The skin construct has a well-developed basement membrane present at the dermal-epidermal junction as exhibited by transmission electron microscopy (TEM). The basement membrane appears thickest around hemidesmosomes, marked by anchoring fibrils that are comprised of type VII collagen, as visualized by TEM. The anchoring fibrils can seen exiting from the basement membrane and entrapping the collagen fibrils in the dermal layer. These anchoring fibrils, as well as other basement membrane components, are secreted by keratinocytes. It is also known that while keratinocytes are capable of secreting basement membrane components on their own, a recognizable basement membrane will not form in the absence of fibroblasts. Immunohistochemical staining of the skin construct of the present invention has also shown that laminin, a basement membrane protein is present.

In a preferred method of the invention for forming a cell-matrix construct, a first cell type, an extracellular matrix-producing cell type, is seeded to a substrate, cultured, and induced to synthesize and secrete an organized extracellular matrix around them to form a cell-matrix construct. In another preferred method of the invention, a surface of the cell-matrix construct is seeded with cells of a second cell type and are cultured to form bilayered tissue construct. In a more preferred method, a full thickness skin construct having features similar to native human skin is formed by culturing fibroblasts, such as human dermal fibroblasts, under conditions sufficient to induce matrix synthesis to form a cell-matrix of dermal cells and matrix, a dermal layer, onto which human epithelial cells, such as keratinocytes, are seeded and cultured under conditions sufficient to form a fully differentiated stratified epidermal layer.

Therefore, one method of obtaining the cultured tissue constructs of the present invention comprises:

(a) culturing at least one extracellular matrix-producing cell type in the absence of exogenous extracellular matrix components or a structural support member; and, (b) stimulating the cells of step (a) to synthesize, secrete, and organize extracellular matrix components to form a tissue-construct comprised of cells and matrix synthesized by those cells; wherein steps (a) and (b) may be done simultaneously or consecutively.

To form a bilayer cultured tissue construct comprising a cell-matrix construct and a second cell layer thereon, the method additionally comprises the step of: (c) culturing cells of a second type on a surface of the formed tissue-construct to produce a bilayered tissue construct.

An extracellular matrix-producing cell type for use in the invention may be any cell type capable of producing and secreting extracellular matrix components and organizing the extracellular matrix components to form a cell-matrix construct. More than one extracellular matrix-producing cell type may be cultured to form a cell-matrix construct. Cells of different cell types or tissue origins may be cultured together as a mixture to produce complementary components and structures similar to those found in native tissues. For example, the extracellular matrix-producing cell type may have other cell types mixed with it to produce an amount of extracellular matrix that is not normally produced by the first cell type. Alternatively, the extracellular matrix-producing cell type may also be mixed with other cell types that form specialized tissue structures in the tissue but do not substantially contribute to the overall formation of the matrix aspect of the cell-matrix construct, such as in certain skin constructs of the invention.

While any extracellular matrix-producing cell type may be used in accordance with this invention, the preferred cell types for use in this invention are derived from mesenchyme. More preferred cell types are fibroblasts, stromal cells, and other supporting connective tissue cells, most preferably human dermal fibroblasts found in human dermis for the production of a human dermal construct. Fibroblast cells, generally, produce a number of extracellular matrix proteins, primarily collagen. There are several types of collagens produced by fibroblasts, however, type I collagen is the most prevalent in vivo. Human fibroblast cell strains can be derived from a number of sources, including, but not limited to neonate male foreskin, dermis, tendon, lung, umbilical cords, cartilage, urethra, corneal stroma, oral mucosa, and intestine. The human cells may include but need not be limited to fibroblasts, but may include: smooth muscle cells, chondrocytes and other connective tissue cells of mesenchymal origin. It is preferred, but not required, that the origin of the matrix-producing cell used in the production of a tissue construct be derived from a tissue type that it is to resemble or mimic after employing the culturing methods of the invention. For instance, in the embodiment where a skin-construct is produced, the preferred matrix-producing cell is a fibroblast, preferably of dermal origin.

In another preferred embodiment, fibroblasts isolated by microdissection from the dermal papilla of hair follicles can be used to produce the matrix alone or in association with other fibroblasts. In the embodiment where a corneal-construct is produced, the matrix-producing cell is derived from corneal stroma. Cell donors may vary in development and age. Cells may be derived from donor tissues of embryos, neonates, or older individuals including adults. Embryonic progenitor cells such as mesenchymal stem cells may be used in the invention and induced to differentiate to develop into the desired tissue.

Although human cells are preferred for use in the invention, the cells to be used in the method of the are not limited to cells from human sources. Cells from other mammalian species including, but not limited to, equine, canine, porcine, bovine, and ovine sources; or rodent species such as mouse or rat may be used. In addition, cells that are spontaneously, chemically or virally transfected or recombinant cells or genetically engineered cells may also be used in this invention. For those embodiments that incorporate more than one cell type, chimeric mixtures of normal cells from two or more sources; mixtures of normal and genetically modified or transfected cells; or mixtures of cells of two or more species or tissue sources may be used.

Recombinant or genetically-engineered cells may be used in the production of the cell-matrix construct to create a tissue construct that acts as a drug delivery graft for a patient needing increased levels of natural cell products or treatment with a therapeutic. The cells may produce and deliver to the patient via the graft recombinant cell products, growth factors, hormones, peptides or proteins for a continuous amount of time or as needed when biologically, chemically, or thermally signaled due to the conditions present in the patient. Either long or short-term gene product expression is desirable, depending on the use indication of the cultured tissue construct. Long term expression is desirable when the cultured tissue construct is implanted to deliver therapeutic products to a patient for an extended period of time.

Conversely, short term expression is desired in instances where the cultured tissue construct is grafted to a patient having a wound where the cells of the cultured tissue construct are to promote normal or near-normal healing or to reduce scarification of the wound site. Once the wound has healed, the gene products from the cultured tissue construct are no longer needed or may no longer be desired at the site. Cells may also be genetically engineered to express proteins or different types of extracellular matrix components which are either 'normal' but expressed at high levels or modified in some way to make a graft device comprising extracellular matrix and living cells that is therapeutically advantageous for improved wound healing, facilitated or directed neovascularization, or minimized scar or keloid formation. These procedures are generally known in the art, and are described in Sambrook et al, *Molecular Cloning A Laboratory Manual*, Cold Spring Harbor Press, Cold Spring Harbor, N.Y. (1989), incorporated herein by reference. All of the above-mentioned types of cells are included within the definition of a "matrix-producing cell" as used in this invention.

The predominant major extracellular matrix component produced by fibroblasts is fibrillar collagen, particularly collagen type I. Fibrillar collagen is a key component in the cell-matrix structure; however, this invention is not to be limited to matrices comprised of only this protein or protein type. For instance, other collagens, both fibrillar and non-fibrillar collagen from the collagen family such as collagen types II, III, IV, V, VI, VII, VIII, IX, X, XI, XII, XIII, XIV, XV, XVI, XVII, XVIII, XIX, may be produced by use of the appropriate cell type. Similarly, other matrix proteins which can be produced and deposited using the current method include, but are not limited to elastin; proteoglycans such as decorin or biglycan; or glycoproteins such as tenascin; vitronectin; fibronectin; laminin, thrombospondin I, and glycosaminoglycans (GAG) such as hyaluronic acid (HA).

The matrix-producing cell is cultured in a vessel suitable for animal cell or tissue culture, such as a culture dish, flask, or roller-bottle, which allows for the formation of a three-dimensional tissue-like structure. Suitable cell growth surfaces on which the cells can be grown can be any biologically compatible material to which the cells can adhere and provide an anchoring means for the cell-matrix construct to form. Materials such as glass; stainless steel; polymers, including polycarbonate, polystyrene, polyvinyl chloride, polyvinylidene, polydimethylsiloxane, fluoropolymers, and fluorinated ethylene propylene; and silicon substrates, including fused silica, polysilicon, or silicon crystals may be used as a cell growth surfaces. The cell growth surface material may be chemically treated or modified, electrostatically charged, or coated with biologicals such as poly-l-lysine or peptides. An example of a peptide coating is RGD peptide.

While the tissue construct of the invention may be grown on a solid cell growth surface, a cell growth surface with pores that communicate both top and bottom surfaces of the membrane to allow bilateral contact of the medium to the developing tissue construct or for contact from only below the culture is preferred. Bilateral contact allows medium to contact both the top and bottom surfaces of the developing construct for maximal surface area exposure to the nutrients contained in the medium. Medium may also contact only the bottom of the forming cultured tissue construct so that the top surface may be exposed to air, as in the development of a cultured skin construct.

The preferred culture vessel is one that utilizes a carrier insert, a culture-treated permeable member such as a porous membrane that is suspended in the culture vessel containing medium. Typically, the membrane is secured to one end of a tubular member or framework that is inserted within and interfaces with a base, such as a petri or culture dish that can be covered with a lid. Culture vessels incorporating a carrier insert with a porous membrane are known in the art and are preferred for carrying out the invention and are described in a number United States patents in the field, some of which have been made commercially available, including for instance: U.S. Pat. Nos. 5,766,937, 5,466,602, 5,366,893, 5,358,871, 5,215,920, 5,026,649, 4,871,674, 4,608,342, the disclosures of which are incorporated herein. When these types of culture vessels are employed, the tissue-construct is produced on one surface of the membrane, preferably the top, upwardly facing surface and the culture is contacted by cell media on both top and bottom surfaces.

The pores in the growth surface allow for the passage of culture media for providing nutrients to the underside of the culture through the membrane, thus allowing the cells to be fed bilaterally or solely from the bottom side. A preferred pore size is one that is small enough that it does not allow for the growth of cells through the membrane, yet large enough to allow for free passage of nutrients contained in culture medium to the bottom surface of the cell-matrix construct, such as by capillary action.

Preferred pore sizes are about less than 3 microns but range between about 0.1 microns to about 3 microns, more preferably between about 0.2 microns to about 1 micron and most preferably about 0.4 micron to about 0.6 micron sized pores are employed. In the case of human dermal fibroblasts, the most preferred material is polycarbonate having a pore size is between about 0.4 to about 0.6 microns. The maximum pore size depends not only on the size of the cell but also the ability of the cell to alter its shape and pass through the membrane. It is important that the tissue-like construct adheres to the surface but does not incorporate or envelop the substrate so it is removable from it such as by peeling with minimal force.

The size and shape of the tissue construct formed is dictated by the size of the vessel surface or membrane on which it grown. Substrates may be round or angular or shaped with rounded corner angles, or irregularly shaped. Substrates may also be flat or contoured as a mold to produce a shaped construct to interface with a wound or mimic the physical structure of native tissue. To account for greater surface areas of the growth substrate, proportionally more cells are seeded to the surface and a greater volume of media is needed to sufficiently bathe and nourish the cells. When the tissue construct is finally formed, whether it is a single layer cell-matrix construct or a bilayer construct, it is removed by peeling from the membrane substrate before grafting to a patient.

The cultured tissue constructs of the invention do not rely on synthetic or bioresorbable members for, such as a mesh member for the formation of the tissue constructs. The mesh member is organized as a woven, a knit, or a felt material. In systems where a mesh member is employed, the cells are cultured on the mesh member and growing on either side and within the interstices of the mesh to envelop and incorporate the mesh within the cultured tissue construct. The final construct formed by methods that incorporate such a mesh rely on it for physical support and for bulk. Examples of cultures tissue constructs that rely on synthetic mesh members are found in U.S. Pat. Nos. 5,580,781, 5,443,950, 5,266,480, 5,032,508, 4,963,489 to Naughton, et al.

The system for the production of the cell-matrix layer may be either static or may employ a perfusion means to the culture media. In the static system, the culture medium is still and relatively motionless as contrasted to the perfusion system where the medium is in motion. The perfusion of medium affects the viability of the cells and augments the development of the matrix layer. Perfusion means include, but are not limited to: using a magnetic stirbar or motorized impeller in the culture dish subjacent (below) or adjacent to the substrate carrier containing the culture membrane to stir the medium; pumping medium within or through the culture dish or chamber; gently agitating the culture dish on a shaking or rotating platform; or rolling, if produced in a roller bottle. Other perfusion means can be determined by one skilled in the art for use in the method of the invention.

Culture media formulations suitable for use in the present invention are selected based on the cell types to be cultured and the tissue structure to be produced. The culture medium that is used and the specific culturing conditions needed to promote cell growth, matrix synthesis, and viability will depend on the type of cell being grown.

In some instances, such as in the fabrication of bioengineered bilayer skin constructs of the present invention, the media composition varies with each stage of fabrication as different supplementation is necessary for different purposes. In a preferred method, the cell-matrix layer is formed under defined conditions, that is, cultured in chemically defined media. In another preferred method, a tissue construct comprises a cell-matrix layer provided with a second layer of cells disposed and cultured thereon wherein both cell types are cultured in a defined culture media system. Alternatively, the tissue construct comprises a cell-matrix layer fabricated under defined media conditions and a second layer formed thereon under undefined media conditions. In the converse, the tissue construct comprises a cell-matrix layer may be fabricated under undefined media conditions and the second layer formed thereon under defined media conditions.

The use of chemically defined culture media is preferred, that is, media free of undefined animal organ or tissue extracts, for example, serum, pituitary extract, hypothalamic extract, placental extract, or embryonic extract or proteins and factors secreted by feeder cells. In a most preferred embodiment, the media is free of undefined components and defined biological components derived from non-human sources. Although the addition of undefined components is not preferred, they may be used in accordance with the disclosed methods at any point in culture in order to fabricate successfully a tissue construct. When the invention is carried out utilizing screened human cells cultured using chemically defined components derived from no non-human animal sources, the resultant tissue construct is a defined human tissue construct. Synthetic functional equivalents may also be added to supplement chemically defined media within the purview of the definition of chemically defined for use in the most preferred fabrication method. Generally, one of skill in the art of cell culture will be able to determine suitable natural human, human recombinant, or synthetic equivalents to commonly known animal components to supplement the culture media of the invention without undue investigation or experimentation. The advantages in using such a construct in the clinic is that the concern of adventitious animal or cross-species virus contamination and infection is diminished. In the testing scenario, the advantages of a chemically defined construct is that when tested, there is no chance of the results being confounded due to the presence of the undefined components.

Culture medium is comprised of a nutrient base usually further supplemented with other components. The skilled artisan can determine appropriate nutrient bases in the art of animal cell culture with reasonable expectations for successfully producing a tissue construct of the invention. Many commercially available nutrient sources are useful on the practice of the present invention. These include commercially available nutrient sources which supply inorganic salts, an energy source, amino acids, and B-vitamins such as Dulbecco's Modified Eagle's Medium (DMEM); Minimal Essential Medium (MEM); M199; RPMI 1640; Iscove's Modified Dulbecco's Medium (EDMEM). Minimal Essential Medium (MEM) and M199 require additional supplementation with phospholipid precursors and non-essential amino acids. Commercially available vitamin-rich mixtures that supply additional amino acids, nucleic acids, enzyme cofactors, phospholipid precursors, and inorganic salts include Ham's F-12, Ham's F-10, NCTC 109, and NCTC 135. Albeit in varying concentrations, all basal media provide a basic nutrient source for cells in the form of glucose, amino acids, vitamins, and inorganic ions, together with other basic media components. The most preferred base medium of the invention comprises a nutrient base of either calcium-free or low calcium Dulbecco's Modified Eagle's Medium (DMEM), or, alternatively, DMEM and Ham's F-12 between a 3-to-1 ratio to a 1-to-3 ratio, respectively.

The base medium is supplemented with components such as amino acids, growth factors, and hormones. Defined culture media for the culture of cells of the invention are described in U.S. Pat. No. 5,712,163 to Parenteau and in International PCT Publication No. WO 95/31473, the disclosures of which are incorporated herein by reference. Other media are known in the art such as those disclosed in Ham and McKeehan, Methods in Enzymology, 58:44-93 (1979), or for other appropriate chemically defined media, in Bottenstein et al., Methods in Enzymology, 58:94-109 (1979). In the preferred embodiment, the base medium is supplemented with the following components known to the skilled artisan in animal cell culture: insulin, transferrin, triiodothyronine (T3), and either or both ethanolamine and o-phosphoryl-ethanolamine, wherein concentrations and substitutions for the supplements may be determined by the skilled artisan.

Insulin is a polypeptide hormone that promotes the uptake of glucose and amino acids to provide long term benefits over multiple passages. Supplementation of insulin or insulin-like growth factor (IGF) is necessary for long term culture as there will be eventual depletion of the cells' ability to uptake glucose and amino acids and possible degradation of the cell phenotype. Insulin may be derived from either animal, for example bovine, human sources, or by recombinant means as human recombinant insulin. Therefore, a human insulin would qualify as a chemically defined component not derived from a non-human biological source. Insulin supplementation is advisable for serial cultivation and is provided to the media at a wide range of concentrations. A preferred concentration range is between about 0.1 μg/ml to about 500 μg/ml, more preferably at about 5 μg/ml to about 400 μg/ml, and most preferably at about 375 μg/ml. Appropriate concentrations for the supplementation of insulin-like growth factor, such as IGF-1 or IGF-2, may be easily determined by one of skill in the art for the cell types chosen for culture.

Transferrin is in the medium for iron transport regulation. Iron is an essential trace element found in serum. As iron can be toxic to cells in its free form, in serum it is supplied to cells bound to transferrin at a concentration range of preferably between about 0.05 to about 50 μg/ml, more preferably at about 5 μg/ml.

Triiodothyronine (T3) is a basic component and is the active form of thyroid hormone that is included in the medium to maintain rates of cell metabolism. Triiodothyronine is supplemented to the medium at a concentration range between about 0 to about 400 pM, more preferably between about 2 to about 200 pM and most preferably at about 20 pM.

Either or both ethanolamine and o-phosphoryl-ethanolamine, which are phospholipids, are added whose function is an important precursor in the inositol pathway and fatty acid metabolism. Supplementation of lipids that are normally found in serum is necessary in a serum-free medium. Ethanolamine and o-phosphoryl-ethanolamine are provided to media at a concentration range between about $10^{-6}$ to about $10^{-2}$ M, more preferably at about $1 \times 10^{-4}$ M.

Throughout the culture duration, the base medium is additionally supplemented with other components to induce synthesis or differentiation or to improve cell growth such as hydrocortisone, selenium, and L-glutamine.

Hydrocortisone has been shown in keratinocyte culture to promote keratinocyte phenotype and therefore enhance differentiated characteristics such as involucrin and keratinocyte transglutaminase content (Rubin et al., J. Cell Physiol., 138:208-214 (1986)). Therefore, hydrocortisone is a desirable additive in instances where these characteristics are beneficial such as in the formation of keratinocyte sheet grafts or skin constructs. Hydrocortisone may be provided at a concentration range of about 0.01 ug/ml to about 4.0 μg/ml, most preferably between about 0.4 μg/ml to 16 ug/ml.

Selenium is added to serum-free media to resupplement the trace elements of selenium normally provided by serum. Selenium may be provided at a concentration range of about $10^{-9}$ M to about $10^{-7}$ M; most preferably at about $5.3 \times 10^{-8}$ M.

The amino acid L-glutamine is present in some nutrient bases and may be added in cases where there is none or insufficient amounts present. L-glutamine may also be provided in stable form such as that sold under the mark, GlutaMAX-1™ (Gibco BRL, Grand Island, N.Y.). GlutaMAX-1™ is the stable dipeptide form of L-alanyl-L-glutamine and may be used interchangeably with L-glutamine and is provided in equimolar concentrations as a substitute to L-glutamine. The dipeptide provides stability to L-glutamine from degradation over time in storage and during incubation that can lead to uncertainty in the effective concentration of L-glutamine in medium. Typically, the base medium is supplemented with preferably between about 1 mM to about 6 mM, more preferably between about 2 mM to about 5 mM, and most preferably 4 mM L-glutamine or GlutaMAX-1™.

Growth factors such as epidermal growth factor (EGF) may also be added to the medium to aid in the establishment of the cultures through cell scale-up and seeding. EGF in native form or recombinant form may be used. Human forms, native or recombinant, of EGF are preferred for use in the medium when fabricating a skin equivalent containing no non-human biological components. EGF is an optional component and may be provided at a concentration between about 1 to 15 ng/mL, more preferably between about 5 to 10 ng/mL.

The medium described above is typically prepared as set forth below. However, it should be understood that the components of the present invention may be prepared and assembled using conventional methodology compatible with their physical properties. It is well known in the art to substitute certain components with an appropriate analogous or functionally equivalent acting agent for the purposes of availability or economy and arrive at a similar result. Naturally occurring growth factors may be substituted with recombinant or synthetic growth factors that have similar qualities and results when used in the performance of the invention.

Media in accordance with the present invention are sterile. Sterile components are bought sterile or rendered sterile by conventional procedures, such as filtration, after preparation. Proper aseptic procedures were used throughout the following Examples. DMEM and F-12 are first combined and the individual components are then added to complete the medium. Stock solutions of all components can be stored at −20° C., with the exception of nutrient source that can be stored at 4° C. All stock solutions are prepared at 500× final concentrations listed above. A stock solution of insulin, transferrin and triiodothyronine (all from Sigma) is prepared as follows: triiodothyronine is initially dissolved in absolute ethanol in 1N hydrochloric acid (HCl) at a 2:1 ratio. Insulin is dissolved in dilute HCl (approximately 0.1N) and transferrin is dissolved in water. The three are then mixed and diluted in water to a 500× concentration. Ethanolamine and o-phosphoryl-ethanolamine are dissolved in water to 500× concentration and are filter sterilized. Progesterone is dissolved in absolute ethanol and diluted with water. Hydrocortisone is dissolved in absolute ethanol and diluted in phosphate buffered saline (PBS). Selenium is dissolved in water to 500× concentration and filter sterilized. EGF is purchased sterile and is dissolved in PBS. Adenine is difficult to dissolve but may be dissolved by any number of methods known to those skilled in the art. Serum albumin may be added to certain components in order to stabilize them in solution and are presently derived from either human or animal sources. For example, human serum albumin (HSA) or bovine serum albumin (BSA) may be added for prolonged storage to maintain the activity of the progesterone and EGF stock solutions. The medium can be either used immediately after preparation or, stored at 4° C. If stored, EGF should not be added until the time of use.

In order to form the cell-matrix layer by the culture of matrix-producing cells, the medium is supplemented with additional agents that promote matrix synthesis and deposition by the cells. These supplemental agents are cell-compatible, defined to a high degree of purity and are free of contaminants. The medium used to produce the cell-matrix layer is termed "matrix production medium".

To prepare the matrix production medium, the base medium is supplemented with an ascorbate derivative such as sodium ascorbate, ascorbic acid, or one of its more chemically stable derivatives such as L-ascorbic acid phosphate magnesium salt n-hydrate. Ascorbate is added to promote hydroxylation of proline and secretion of procollagen, a soluble precursor to deposited collagen molecules. Ascorbate has also been shown to be an important cofactor for post-translational processing of other enzymes as well as an upregulator of type I and type III collagen synthesis.

While not wishing to be bound by theory, supplementing the medium with amino acids involved in protein synthesis conserves cellular energy by not requiring the cells produce the amino acids themselves. The addition of proline and glycine is preferred as they, as well as the hydroxylated form of proline, hydroxyproline, are basic amino acids that make up the structure of collagen.

While not required, the matrix-production medium is optionally supplemented with a neutral polymer. The cell-matrix constructs of the invention may be produced without a neutral polymer, but again not wishing to be bound by theory, its presence in the matrix production medium may collagen processing and deposition more consistently between samples. One preferred neutral polymer is polyethylene glycol (PEG), which has been shown to promote in vitro processing of the soluble precursor procollagen produced by the cultured cells to matrix deposited collagen. Tissue culture grade PEG within the range between about 1000 to about 4000 MW (molecular weight), more preferably between about 3400 to about 3700 MW is preferred in the media of the invention. Preferred PEG concentrations are for use in the method may be at concentrations at about 5% w/v or less, preferably about 0.01% w/v to about 0.5% w/v, more preferably between about 0.025% w/v to about 0.2% w/v, most preferably about 0.05% w/v. Other culture grade neutral polymers such dextran, preferably dextran T-40, or polyvinylpyrrolidone (PVP), preferably in the range of 30,000-40,000 MW, may also be used at concentrations at about 5% w/v or less, preferably between about 0.01% w/v to about 0.5% w/v, more preferably between about 0.025% w/v to about 0.2% w/v, most preferably about 0.05% w/v. Other cell culture grade and cell-compatible agents that enhance collagen processing and deposition may be ascertained by the skilled routineer in the art of mammalian cell culture.

When the cell producing cells are confluent, and the culture medium is supplemented with components that assist in matrix synthesis, secretion, or organization, the cells are said to be stimulated to form a tissue-construct comprised of cells and matrix synthesized by those cells.

Therefore, a preferred matrix production medium formulation comprises: a base 3:1 mixture of Dulbecco's Modified Eagle's Medium (DMEM) (high glucose formulation, without L-glutamine) and Hams F-12 medium supplemented with either 4 mM L-glutamine or equivalent, 5 ng/ml epidermal growth factor, 0.4 μg/ml hydrocortisone, $1\times10^{-4}$ M ethanolamine, $1\times10^{-4}$ M o-phosphoryl-ethanolamine, 5 μg/ml insulin, 5 μg/ml transferrin, 20 pM triiodothyronine, 6.78 ng/ml selenium, 50 ng/ml L-ascorbic acid, 0.2 μg/ml L-proline, and 0.1 μg/ml glycine. To the production medium, other pharmacological agents may be added to the culture to alter the nature, amount, or type of the extracellular matrix secreted. These agents may include polypeptide growth factors, transcription factors or inorganic salts to up-regulate collagen transcription. Examples of polypeptide growth factors include transforming growth factor-beta 1 (TGF-β1) and tissue-plasminogen activator (TPA), both of which are known to upregulate collagen synthesis. Raghow et al., Journal of Clinical Investigation, 79:1285-1288 (1987); Pardes et al., Journal of Investigative Dermatology, 100:549 (1993). An example of an inorganic salt that stimulates collagen production is cerium. Shivakumar et al., Journal of Molecular and Cellular Cardiology 24:775-780 (1992).

The cultures are maintained in an incubator to ensure sufficient environmental conditions of controlled temperature, humidity, and gas mixture for the culture of cells. Preferred conditions are between about 34° C. to about 38° C., more preferably 37±1° C. with an atmosphere between about 5-10±1% $CO_2$ and a relative humidity (Rh) between about 80-90%.

In the preferred embodiment, the cell-matrix construct is a dermal construct formed of dermal fibroblasts and their secreted matrix. Preferably, human dermal fibroblasts are used, derived as primary cells from dermis or more preferably from serially passaged or subcultured from established cell stocks or banks that have been screened against viral and bacterial contamination and tested for purity. Cells are cultured under sufficient conditions in growth medium to cause them to proliferate to an appropriate number for seeding the cells to the culture substrate on which to form a cell-matrix construct. Alternatively, cells from frozen cell stocks may be seeded directly to the culture substrate.

Once sufficient cell numbers have been obtained, cells are harvested and seeded onto a suitable culture surface and cultured under appropriate growth conditions to form a confluent sheet of cells. In the preferred embodiment, the cells are seeded on a porous membrane that is submerged to allow medium contact from below the culture through the pores and directly above. Preferably, cells are suspended in either base or growth media and are seeded on the cell culture surface at a density between about $1\times10^5$ cells/cm$^2$ to about $6.6\times10^5$ cells/cm$^2$, more preferably between about $3\times10^5$ cells/cm$^2$ to about $6.6\times10^5$ cells/cm$^2$, and most preferably at about $6.6\times10^5$ cells/cm$^2$ (cells per square centimeter area of the surface). Cultures are cultured in growth medium to establish the culture and are cultured to between about 80% to 100% confluence at which time they are induced chemically by changing the medium to matrix production medium in order to upregulate the synthesis and secretion of extracellular matrix. In an alternate method, cells are seeded directly in production media to eliminate the need to change from the basic media to the production media but it is a method that requires higher seeding densities.

During the culture, fibroblasts organize the secreted matrix molecules to form a three dimensional tissue-like structure but do not exhibit significant contractile forces to cause the forming cell-matrix construct to contract and peel itself from the culture substrate. Media exchanges are made every two to three days with fresh matrix production medium and with time, the secreted matrix increases in thickness and organization. The time necessary for creating a cell-matrix construct is dependent on the ability of the initial seeding density, the cell type, the age of the cell line, and the ability of the cell line to synthesize and secrete matrix. When fully formed, the constructs of the invention have bulk thickness due to the fibrous matrix produced and organized by the cells; they are not ordinary confluent or overly confluent cell cultures where the cells may be loosely adherent to each other. The fibrous quality gives the constructs cohesive tissue-like properties unlike ordinary cultures because they resist physical damage, such as tearing or cracking, with routine handling in a clinical setting. In the fabrication of a cultured dermal construct, the cells will form an organized matrix around themselves on the cell culture surface preferably at least about 30 microns in thickness or more, more preferably between about 60 to about 120 microns thick across the surface of the membrane; however, thicknesses have been obtained in excess of 120 microns and are suitable for use in testing or clinical applications where such greater thicknesses are needed.

In a more preferred method, an epithelial cell layer is applied to one surface, preferably the top, upwardly facing surface of the cell-matrix construct. To the cell-matrix construct, epithelial cells may be seeded and cultured thereon to form a multilayer tissue construct. In the most preferred method, keratinocytes derived from skin are grown on the cell construct to form a skin construct. In other preferred embodiments, corneal epithelial cells, also termed corneal keratinocytes, may be seeded on the cell-matrix construct to form a corneal construct. Epithelial cells from the oral mucosa may be grown on the cell-matrix construct to form a construct of oral mucosa. Epithelial cells from esophagus may be seeded on the cell-matrix construct to form a construct of esophageal tissue. Uroepithelial cells from the urogenital tract may be seeded on the cell-matrix construct to form a construct of uroepithelium. Other cells of epithelial origin may be selected to form a construct of tissue from which those cells were derived.

Methods for providing epidermal cells to a dermal substrate, and methods for their culture, including induction of differentiation and cornification to form a differentiated keratinocyte layer are known in the art and are described in U.S. Pat. No. 5,712,163 to Parenteau, et al. and in U.S. Pat. No. 5,536,656 to Kemp, et al., the contents of which are incorporated herein by reference in their entirety. Typically to perform the epidermalization of the cell-matrix construct, keratinocytes are seeded to the cell-matrix construct and cultured thereon until the layer is about one to three cell layers thick. The keratinocytes are then induced to differentiate to form a multilayer epidermis and are then induced to cornify to form a stratum corneum.

In the method of forming a differentiated epidermal layer, subcultured keratinocytes are taken from the cell stock and their cell numbers are expanded. When an necessary number of cells have been obtained, they are released from the culture substrate, suspended, counted, diluted and then seeded to the top surface of the cell-matrix construct at a density between about $4.5 \times 10^3$ cells/cm$^2$ to about $5.0 \times 10^5$ cells/cm$^2$, more preferably between about $1.0 \times 10^4$ cells/cm$^2$ to about $1.0 \times 10^5$ cells/cm$^2$, and most preferably at about $4.5 \times 10^4$ cells/cm$^2$. The constructs are then incubated for between about 60 to about 90 minutes at $37 \pm 1°$ C., 10% $CO_2$ to allow the keratinocytes to attach. After the incubation, the constructs are submerged in epidermalization medium. After a sufficient length of time in culture, the keratinocytes proliferate and spread to form a confluent monolayer across the cell-matrix construct. Once confluent, the cell media formulation is changed to differentiation medium to induce cell differentiation. When a multilayer epithelium has formed, cornification media is then used and the culture is brought to the air-liquid interface. For the differentiation and cornification of keratinocytes, the cells are exposed to a dry or low humidity air-liquid interface. A dry or low-humidity interface can be characterized as trying to duplicate the low moisture levels of skin. With time, keratinocytes will express most or all keratins and other features found in native skin when exposed to these conditions.

As mentioned above, the system for the production of a cell-matrix construct may be used in the formation of a corneal construct. The corneal epithelial cells can be derived from a variety of mammalian sources. The preferred epithelial cell is a rabbit or human corneal epithelial cell (corneal keratinocyte) but any mammalian corneal keratinocyte may be used. Other epithelial keratinocytes such as those derived from the sclera (outer white opaque portion) of the eye or epidermis may be substituted, but corneal keratinocytes are preferable. In the method for forming a corneal construct, the medium is removed from the culture insert (containing the cell-matrix construct) and its surround. Normal rabbit corneal epithelial cells are expanded via subculture, trypsinized to remove them from the cultures substrate, suspended in culture medium, and seeded on top of the membrane at a density between about $7.2 \times 10^4$ to about $1.4 \times 10^5$ cells/cm$^2$. The constructs are then incubated without medium for about four hours at $37 \pm 1°$ C., 10% $CO_2$ to allow the epithelial cells to attach. After incubation, the constructs are submerged in Corneal Maintenance Medium (CMM) (Johnson et al., 1992.) The epithelial cells are cultured until the cell-matrix construct is covered with the epithelial cells. Completeness of epithelial coverage can be ascertained by a variety of methods, for illustration by staining the culture with a solution of Nile Blue sulfate (1:10,000 in phosphate buffered saline). Once the cell-matrix construct is covered, after approximately seven days, the constructs are aseptically transferred to new culturing trays with sufficient cornea maintenance medium (CMM) to achieve a fluid level just to the surface of the construct to maintain a moist interface without submersion of the epithelial layer. The constructs are incubated at $37 \pm 1°$ C., 10% $CO_2$, and greater than 60% humidity, with the CMM, making media changes, as necessary, typically, three times per week.

For the differentiation, but not the cornification of the epithelial cell layer, as necessary in the production of a corneal construct, the epithelial cell surface is exposed to a moist air-liquid interface. Methods for providing a moist air-liquid interface are described in U.S. Pat. No. 5,374,515 to Parenteau. As used herein, the term "moist interface" is intended to mean a culture environment which is regulated so that the surface of the construct is moist, with high humidity, but not dry or submerged. The exact level of moisture and humidity in the culture environment is not critical, but it should be sufficiently moist and humid to avoid the formation of cornified cells. A moist interface can be characterized as trying to duplicate similar moisture levels of the human eye.

In an alternate preferred embodiment, a seeding of a second matrix-producing cell may be performed on a first formed cell-matrix construct to obtain a thicker cell-matrix construct or a bilayer cell-matrix construct. The second seeding can be performed with the same cell type or strain or with a different cell type or strain, depending on the desired result. The second seeding is performed under the same conditions employing the procedures and matrix production medium used in the production of the first layer. One result in performing the second seeding with a different cell type is to have a matrix formed with different matrix component profiles or matrix packing density to affect wound healing when the construct is grafted to a patient. The first cell seeding produces a matrix analogous to the reticular layer of dermis, a more densely packed layer of Type I collagen and constituent extracellular matrix components. The second cell seeding would produces a matrix similar to the papillary layer of dermis characterized by looser collagen fibrils and extracellular matrix. Another result is the second cell type may produce a therapeutic substance that would also affect wound healing, such as improved graft take or graft integration or the minimization or prevention of scar formation.

In another preferred embodiment, mixed cell populations of two or more cell types may be cultured together during the formation of a cell-matrix construct provided that at least one of the cell types used is capable of synthesizing extracellular matrix. The second cell type may be one needed to perform other tissue functions or to develop particular structural features of the tissue construct. For instance, in the production of a skin construct, dermal papilla cells or epithelial cells from adnexas may be cultured with the matrix-producing cells to allow the formation of epithelial appendages or their components. Epidermal appendages such as sweat or sebaceous gland structures or components or hair follicle structures or components may form when cultured together with the matrix-producing cells. Epithelial cells may be derived from the appendageal structures of gland and hair located in deep dermis, such as by microdissection, and include eccrine cells, myoepithelial cells, glandular secretory cells, hair follicle stem cells. Other cell types normally found in skin that constitute skin may also be added such as melanocytes, Langerhans cells, and Merkel cells. Similarly, vascular endothelial cells may be co-cultured to produce rudimentary components for new vasculature formation. Adipocytes may also be cultured with the matrix-producing cells to form a construct used for reconstructive surgery. As alternate mode of delivery of this second cell type, the cells may locally seeded as a spot or as an arrangement of any number of spots of cells on or within a forming or completely formed cell-tissue matrix for localized development of these structures. To seed the cells within the cell-matrix construct, the cells may be injected between the top and bottom surfaces, within the cell-matrix, for the cells to grow, form specialized structures and perform their specialized function. To produce a three-layered tissue construct, a first seeding of cells comprising a matrix-producing cell type or a non-matrix-producing cell type is seeded on the culture substrate for a time sufficient to produce a cell-matrix construct or a cell layer. Once the first cell-matrix construct or cell layer is formed, a second seeding of cells comprising a matrix-producing cell type is seeded on the top surface of the first cell-matrix construct or cell layer and cultured for a time under conditions sufficient to form a second cell-matrix construct on the first construct. On the second cell-matrix construct, a third seeding of a third cell type is seeded and cultured under sufficient conditions to produce the third layer. As an example, to produce a three-layer corneal construct, the cell of the first cell-type may be comprised of endothelial origin, such as corneal endothelial cells; the second cell type may comprise cells of connective tissue origin, such as corneal keratocytes; and the third cell type may comprise cells of epithelial origin, such as corneal epithelial cells. As another example of a three-layer construct of skin, the cell of the first seeding may be of vascular origin to provide components for vascularization, the cells of the second seeding may comprise dermal fibroblasts to form a cell-matrix construct to serve as a dermal construct, and the cells of the third seeding may be epidermal keratinocytes to form an epidermal layer.

Tissue constructs of the invention can be stored at cryogenic temperatures when vitrification or cryopreservation methods are employed. Methods for vitrification of tissue constructs are described in U.S. Pat. No. 5,518,878 and methods for cryopreservation are described in U.S. Pat. Nos. 5,689,961 and 5,891,617 and in International PCT Application WO 96/24018, the disclosures of which are incorporated herein by reference.

C: Culture Tissue Constructs Comprising a Gel Mixture of a Collagen Solution with a Contractile Agent In another embodiment of this invention, the cultured tissue constructs comprise a gel mixture comprising a collagen solution and a contractile agent.

This cultured tissue construct is produced by forming a hydrated collagen lattice, in vitro, as disclosed in U.S. Pat. No. 4,485,096 to Bell incorporated herein by reference in its entirety. This lattice is contracted into a cultured tissue construct with a contractile agent incorporated in it. Examples of contractile agents are fibroblast cells and blood platelets.

A skin-equivalent can be produced from this living connecting tissue substrate by plating keratinocyte cells on it and providing for their growth. This skin-equivalent is uniquely different from the previously described artificial skins because its basic organization is like that of skin and its living constituent cells may even be donated by a potential graft recipient.

Gland/organ equivalents or small vessel equivalents can be formed from the contracted hydrated collagen lattices described herein.

Thus, it can be seen that the cultured tissue construct produced according to this invention offer the potential of producing living tissue, gland and organ equivalents of many types and functions. Such equivalents may even be fabricated and stored as inventory until a need to employ them arises.

One of the major advantages of such cultured tissue constructs is that they can be employed in a host other than the donor of the cells used to produce the cultured tissue constructs without suffering from the serious problems of rejection which might be expected. This is because selection against cells responsible for rejection by a recipient's immune system takes place when the cells used for the fabrication of the living tissue are propagated according to this invention. In addition, certain cells lose their ability to stimulate rejection when preserved in tissue culture under certain conditions according to recent research reports.

Hydrated collagen lattices can be prepared employing collagen derived from rat tail tendon and calf skin collagen. Other sources of collagen including human fetal skin have been employed, and still other sources would be suitable. Solutions of collagen are prepared and maintained under slightly acidic conditions. Lattices are formed by adding fibroblast cells with nutrient medium and base which raises the pH sufficiently to precipitate collagen fibrils from solution. Preparation of hydrated collagen lattices is described in more detail in the following references, the teachings of which are incorporated by reference: Elsdale, T. and Bard, J., "Collagen Substrata For Studies On Cell Behavior," J. Cell Biol. 54, 626-637 (1972); Ehrmann, R. L. and Gey, G. 0., "The Growth of Cells on A Transparent Gel of Reconstituted Rat-Tail Collagen," J. Natl. Cancer Inst., 16, 1375-1403 (1956); Emermann, J. T. and Pitelka, D. R., "Hormonal Effects on Intracellular and Secreted Casein in Cultures of Mouse Mammary Epithelial Cells on Floating Collagen Membranes," In Vitro, 13, 316-328 (1977); Michalopoulous, G. and Pitot, H. C., "Primary Culture of Parenchymal Liver Cells on Collagen Membranes," Exp. Cell Res. 94, 70-78 (1975); Gey, G. 0. Svotelis, M., Foard, M. and Bang, F. B., "Long-Term Growth of Chicken Fibroblasts On A Collagen Substrate," Exp. Cell Res., 84, 63-71 (1974); and Hillis, W. D. and Band, F. B., "The Cultivation of Human Embryonic Liver Cells," Exp. Cell Res., 26, 9-36 (1962).

Fibroblast cells actually used in the experiments described herein as a contractile agent were human foreskin fibroblasts and guinea pig dermal fibroblasts. Fibroblasts from other sources have also be used, and it is believed, in fact, that fibroblasts from any vertebrate animal would be suitable for contracting hydrated collagen lattices. A convenient technique for simultaneously forming the lattice and plating cells therein involves neutralizing an acidic collagen solution maintained in a culture dish with nutrient medium containing fibroblast cells. Upon neutralization, collagen fibrils precipitate from the solution to form the lattice with fibroblast cells homogeneously dispersed therethrough. The cells and collagen lattice are then maintained under conditions which allow the cells to attach to the collagen lattice and to contract it to a fraction of its original size, thereby providing the living tissue.

The incorporation of fibroblast cells into hydrated collagen lattices causes the lattices to contract as trapped water was squeezed out. If the surface on which the lattice was formed is non-wettable, e.g., a hydrophobic plate, the resulting tissue is of regular geometry. On tissue culture plates, some cells migrate from the lattice to the plate surface and contraction of the lattice is not always regular. When a non-wettable surface, such as a bacteriological Petri plate is used, the lattice remains nearly a perfect disc as its radius is decreased by the cells.

Fibroblast cells are found homogeneously dispersed throughout collagen lattices and not merely upon the lattices' surface. This simulates, then, the dermal layer of humans and other mammals.

In the absence of cells, lattices undergo no change in radius. For example, conditioned medium prepared by growing $1 \times 10^6$ human foreskin fibroblast cells for five days in nutrient medium caused no contraction when no cells were present.

Contracted collagen lattices with cells resemble the skin or dermis; even when partially contracted, they have reasonable consistency and can be readily handled. When first made up with cells, the lattices are almost transparent but gradually become opaque as water is excluded and the diameter reduced. After a 20-30-fold decrease in lattice area, they have a firm rubbery consistency, a whitish pink tint, and can be stretched somewhat without being torn or deformed.

The initial diameter of a lattice is determined by the quantity of materials used and by the plate on which it is formed. Thus, maximal contraction is an arbitrary measure, but is related to cell number and protein concentration.

Although most contracted hydrated collagen lattices have been formed as sheets, other shapes can be formed. Tubes, for example, can be formed by forming the contracted lattice in an annular mold, or a glove of skin might be prepared in an appropriate mold.

Human skin keratinocytes, obtained in biopsies, have been deposited on contracted hydrated collagen lattices. The same has been done with keratinocytes cultivated in vitro. Plating of keratinocytes can be done at the time the matrix gel forms, at any time during the period of contraction of the lattice, or any time after contraction has been completed. Within three days after plating suspensions of dissociated keratinocytes, the cells formed a confluent layer on the lattice surface and the process of keratinization begins leading to the formation of a cornified layer which would prevent loss of tissue fluids.

There are other cellular contractile agents, in addition to fibroblast cells. Among these are smooth muscle cells, striated muscle cells and heart muscle cells.

Lattice contraction by a contractile agent such as fibroblast cells or platelets converts the collagen lattice into a tissue equivalent of relatively high tensile strength compared to that of the collagen lattice cast without a contractile agent, when both are maintained under 100% relative humidity conditions. Cast without a contractile agent, the collagen lattice has a consistency similar to fresh gelatine and falls apart on handling. Lattices contracted by platelets or cells can be handled, stretched and sutured without damage.

Tensile strength has been tested by determining the maximum weight for a given time which could be suspended on contracted lattices. In one example, a lattice of 5 ml volume formed in a 5.3 cm diameter dish and contracted to about 2 cm in diameter by fibroblast cells supported 3.5 grams for 7 min. Another lattice also of 5 ml volume in a 5.3 cm diameter dish was contracted from a height of 0.23 cm to one of 0.09 cm with no change of diameter, by platelets, and supported 11 grams for 10 minutes.

It has been noted that tensile strength, and other properties, are a function of many parameters, including the types and amounts of collagen and contractile agent employed and the other additives employed. The work described herein, for example, employed type I collagen. It is known, however, that type III collagen imparts additional tensile strength to skin and blood vessels, and so it would be expected that the use of type III collagen in the collagen lattices described herein would increase their tensile strength. Similarly, the addition of glycosaminoglycans, such as hyaluronic acid, chondroitin 4-sulfate, and dermatan sulfate, have been found to improve tensile strength and water-retention properties.

Antibiotics, such as penicillin, streptomycin and fungizone can also be added, if desired, to prevent microbial infection.

Although most of the work described herein relates to the formation of skin-equivalents by growing keratinocytes on contracted collagen lattices, other cell types could be grown on or in lattices. Examples are smooth and striated muscle cells, cartilage, bone cells, pancreatic cells, liver cells, etc.

Certain methods and devices have been developed to assist in casting contracted collagen lattices into sheets of controllable dimensions and/or various shapes. With fibroblast cells as the contractile agent, unconstrained collagen lattices typically undergo contraction in all dimensions. However, a sheet whose borders are held fixed contract only in the thickness dimension.

A device suitable for constraining the borders can be made from a sheet of stainless steel mesh of any shape. The desired shape to be cast is cut from the center of the stainless steel mesh after which the excess of the sheet is trimmed off to leave approximately a one-half inch border of mesh around the shape. This forms a frame of stainless steel mesh which can be laid into a pan coated with a non-stick material, such as Teflon® polytetrafluoroethylene, after which the components used to form the lattice are introduced. When the components are poured and the lattice forms, it fills the lacunae of the steel mesh to which is becomes anchored. As the cellular elements of the lattice compact it by pulling together the collagen fibrils, the volume of the lattice decreases, but because the perimeter is held fixed, the dimension which is reduced is the thickness. In the process, the lattice loses fluid.

The special advantage of the steel frame is that the final size of the tissue equivalent is exactly the size of the inside dimensions of the frame and particularly, the lattice acquires additional strength because of the orientation of cells imposed by the constraining frame. Further, since the dimensions of the lattice do not change in width or length, if it is cast in a rectangular frame, even after it is cut away from the frame, it is possible to apply the epidermal component of skin-equivalent to the dermal equivalent as soon as one day after casting the latter thus shaving at least four days off the time needed to prepare a skin-equivalent graft from a biopsy provided by a patient.

Components of a lattice can be poured into the coated pan to cover the restraining mesh. As the lattice sets, it becomes anchored in the mesh so that on contraction, the length and width remain unchanged. Only the thickness decreases. The ultimate dimension of the thickness is a function of (1) the initial volume of the lattice, (2) the cell concentration and (3) the collagen content. The presence of proteoglycans, such as hyaluronic acid and chondroitin sulfate, result in increased contraction and a decrease in lattice thickness. The rectangular mesh which holds the lattice or dermal equivalent onto which epidermal cells are seeded can be applied intact to a wound requiring skin. While in place, it can be cut away from the inside perimeter of the mesh immediately or at some later time since its presence could help to maintain the integrity of the graft.

Another technique and method which are helpful in anchoring epidermis on the dermal equivalent of skin equivalent preparations is as follows. The dermal equivalent is first cast and a plastic sheet, e.g., Teflon® polytetrafluoroethylene, through which needle points have been passed and allowed to remain in a regular pattern, is laid over the fresh casting. The plastic sheets and needle points are removed 1-4 days afterward, when the casting is seeded with epidermal cells. This results in the formation of pits into which the epidermal cells flow thereby providing greater surface contact between the epidermis and dermal equivalent.

Follicle and glandular cells, which can be isolated by an enzymatic dissociation technique, might be seeded with the suspensions of epidermal cells to occupy such pits.

A major advantage of the living tissue described herein is the absence of rejection encountered when the recipient is different than the donor of the cells employed in producing the tissue-equivalent. For example, skin-equivalent grafts fabricated with cells other than those of the graft recipient have now been made to animal hosts. Skin-equivalent grafts made up as described above but assembled with cells from female animals of the Sprague-Dawley strain of rats have been grafted to male Fischer rat hosts and allowed to remain in place for various periods. It can be generalized that equivalent grafts of any kind which are fabricated without specialized immune cells that are ubiquitous in native tissues will not be rejected since the antigenic determinants responsible for graft rejection are not expressed on the surfaces of cells incorporated into equivalent tissues. Their absence makes it impossible for the immune cells of the host to sense the foreign cells. This provides an opportunity to replace or add types of cells, tissue or organs which a recipient needs, because his own are deficient or absent.

D: Cultured Tissue Constructs Comprising a Collagen Gel Layered on a Collagen Gel:

The cultured tissue constructs of this embodiment, although similar in both methods of preparation and use to those comprising a hydrated collagen lattice further comprise a layer of collagen.

It has been discovered that a collagen lattice cast on an acellular, hydrated collagen gel in contact with a permeable member does not undergo substantial radial or lateral contraction while contracting in the thickness dimension, thus eliminating the need to anchor the collagen lattice on, e.g., a stainless steel frame, to control radial or lateral contraction. By way of an example, a 24 mm diameter collagen lattice cast as described above but without an anchoring means, would contract radially to a diameter of 5 mm or less. In contrast, a 24 mm diameter collagen lattice cast on an acellular, hydrated collagen gel in contact with a permeable member will typically contract radially to a diameter of about 15 mm. The elimination of the anchoring means to control lateral/radial contraction offers advantages in terms of cost reduction and ease of fabrication of tissue equivalents. It should be understood that such anchoring means can be used in conjunction with hydrated collagen gel in contact with a permeable member if desired.

One method of obtaining the tissue equivalents of present invention comprises:

(a) forming a mixture comprising collagen and at least one contractile agent; and (b) applying the mixture obtained in step (a) to an acellular, hydrated collagen gel in contact with a permeable member, and maintaining the mixture and gel under conditions which permit formation of the tissue equivalent.

In some embodiments of the present invention, one or more absorbent members, including but not limited to, fibrous pads, cotton pads and gels, agarose, are used in conjunction with the collagen gel described above. Such absorbent members have been found to provide a consistent and level physical support and to promote uniform contact between the tissue equivalent and the cell culture medium. Typically, the absorbent member is adjacent to the surface of the collagen gel opposite the hydrated collagen lattice. Where the absorbent member(s) is itself a gel, e.g., agarose, the gel may be provided together with a nutrient media to provide nutrients to the tissue equivalent.

The following experimental endpoints have been monitored in tissue equivalents maintained with and without the hydrated collagen gel and/or the absorbent member during various phases of development of a skin tissue equivalent:

1. Glucose utilization;
2. The extent and quality of epidermal stratification and cornification;
3. pH of medium.

The observed pH of media obtained from tissue equivalents maintained with the absorbent member(s) were consistently higher, and closer to physiological pH than tissue equivalents maintained in the absence of these members. In addition, glucose utilization was observed to be generally lower in tissue equivalents maintained with the absorbent member.

It has surprisingly been found that mature cornification is promoted in skin tissue equivalents made by use of the absorbent member(s) compared to control skin equivalents made without such members. Although the mechanism by which these absorbent members may influence epidermal differentiation is unknown, it is postulated that such members may act as diffusion barriers, e.g., a permeability barrier, and may filter the medium and/or to retain secreted cellular products in close proximity to the tissue equivalents.

Living skin equivalents of the present invention are prepared as described above, except that in accordance with this embodiment, the hydrated collagen lattice is cast on an acellulor, hydrated collagen gel.

One method of producing a skin tissue equivalent in accordance with the present invention comprises:
(a) forming a mixture comprising collagen and at least one contractile agent;
(b) applying the mixture obtained in step (a) to an acellulor, hydrated collagen gel in contact with a permeable member, and maintaining the mixture and gel under conditions which permit formation of the tissue equivalent; and
(c) seeding the tissue equivalent obtained in step (b) with keratinocytes.

By way of background, one convenient protocol for casting the tissue equivalents of the present invention, involves rapidly mixing together an acidic solution of collagen having a pH of about 3 to 4, with nutrient media, adjusting the pH of the resultant solution, if necessary, to about pH 6.6 to pH 7.8, adding fibroblast cells, transferring the resultant mixture (the "casting mixture") into an appropriate mold or casting device having an acellular, hydrated collagen gel disposed therein and, then, incubating at a temperature preferably about 35° C. to 38° C. It is most convenient to adjust pH and combine the ingredients of the casting mixture simultaneously. However, these steps may be carried out in any desired order, provided that the steps are completed so that the casting mixture can be transferred to a mold for appropriate setting. The collagen fibrils precipitate from the casting mixture as a result of warming the solution and raising the pH to form a hydrated collagen gel contracted by a contractile agent and disposed on hydrated collagen gel.

Although the methods of making living tissue provided by this embodiment are applicable to the fabrication of tissue equivalents in general, these methods will be illustrated in connection with the production of skin equivalents for use in skin grafting applications and in test systems incorporating skin equivalents.

Referring to the drawings, FIGS. 13-15 illustrate one embodiment of an apparatus for determining the interaction of skin and one or more agents by use of skin tissue equivalents in accordance with the present invention, wherein multiple containers 10,22 having tissue equivalents of the present invention disposed therein are provided in a base or holder. The apparatus shown in FIGS. 13-15 is also provided with a cover means 2. In some embodiments a covering (not shown) is provided for each container 10, 20. The covering is selected from any biocompatible material which will hold a seal on the container. Acceptable covering materials include foils and barrier films which may be sealed to the apparatus by means of an adhesive or heat. A heat sealable polyester film is particularly useful in the practice of the present invention.

The containers for the tissue equivalents comprise an outer container 10 and an inner container 20. The inner container 20 is provided with a rim 50 to provide means for positioning the inner container 20 in the outer container 10 thereby defining an outer area 14 and an inner area 22. The inner container 20 is provided with a skin tissue equivalent 26, 28 disposed on hydrated collagen gel 25 which is in turn disposed adjacent a permeable member 24. The permeable member is sealably attached to the inner container 20 to form the bottom surface thereof. The skin tissue equivalent comprises two layers 26, 28, layer 28 comprising an epidermal layer, layer 26 comprising a dermal layer. In some embodiments, a sealing member 30 provides a seal between the inner wall of the inner container 20 and the skin equivalent 26, 28 and covers the perimeter of hydrated collagen gel 25 in the case where the outer edge of the tissue equivalent 26, 28 is positioned inward of hydrated collagen gel 25. In the embodiments pictured in the Figures, the container 10 is provided with an opening 21 which provide access to the outer area 14.

The apparatus depicted in FIG. 15 is further provided with a absorbent member 32. In yet other embodiments, the outer chamber 14 may have a gel, not shown, disposed therein.

Figure 16:
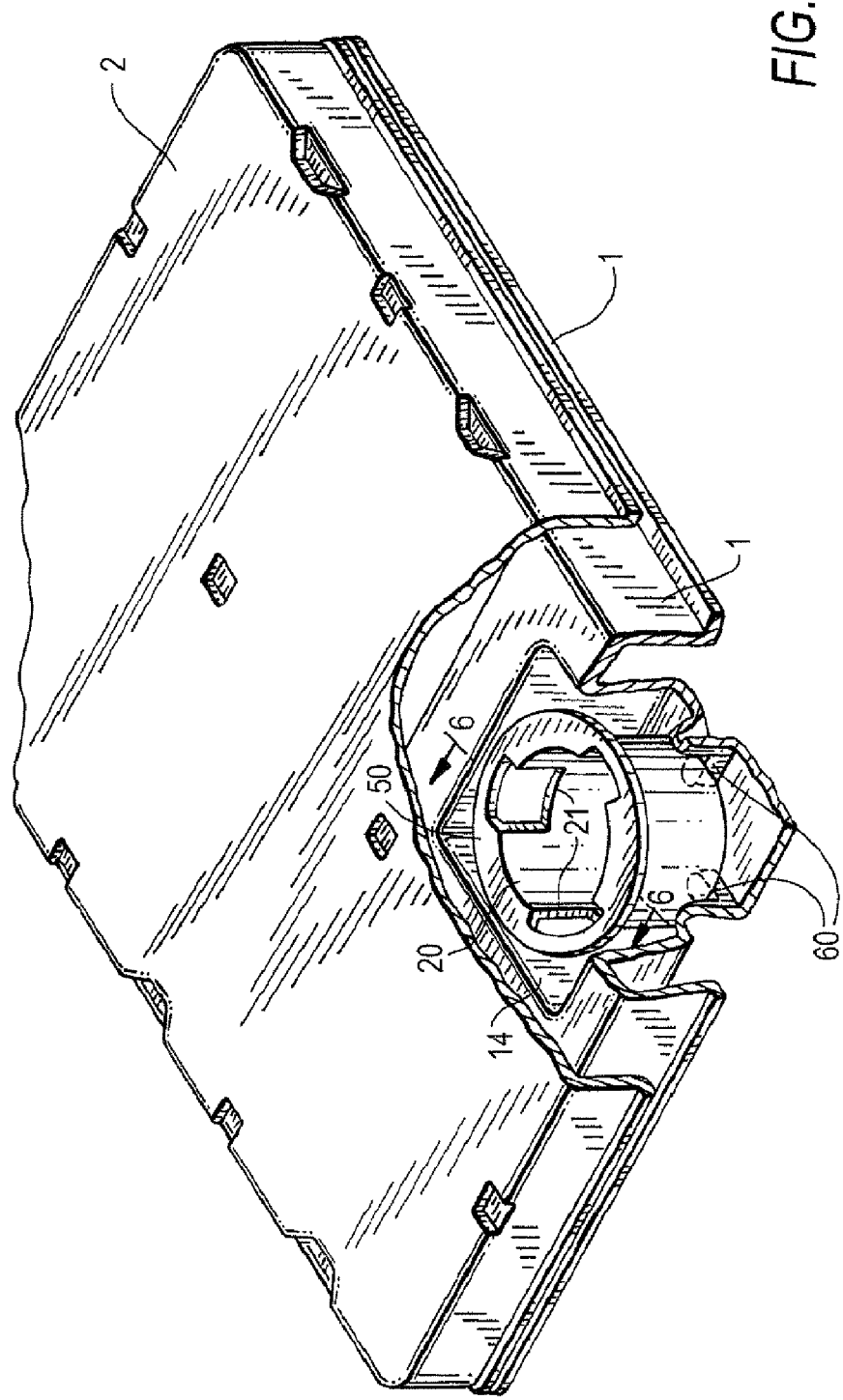
FIG. 16 is an isometric view, partially broken away, of another apparatus in accordance with the present invention.
Figure 17:
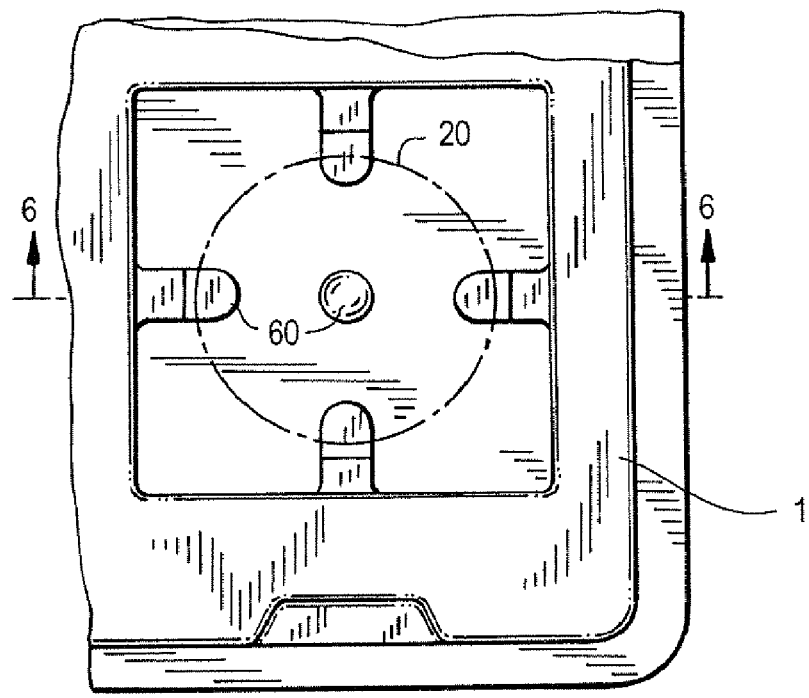
FIG. 17 is an exploded view from above of the apparatus shown in FIG. 16.
Figure 18:
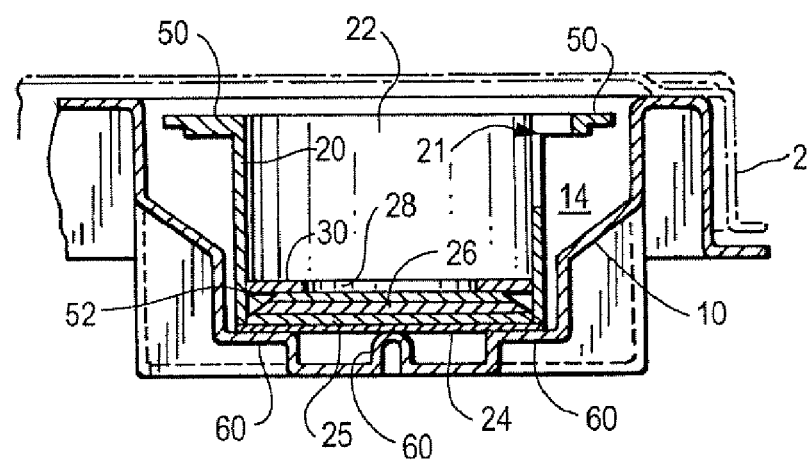
FIG. 18 is an exploded section along 6-6 through the apparatus shown in FIG. 16.

FIGS. 16-18 illustrate another embodiment of an apparatus for determining the interaction of tissue and one or more agents by use of tissue equivalents in accordance with the present invention. Elements similar to those in other described embodiments are indicated by the same numeral. In this embodiment, the outer well 10 is square and is provided with elevated sections 60 in the bottom on which the inner container 20 may be positioned. The outer well 10 rather than projecting upwardly from the bottom of the apparatus is formed as a pocket from the top of the apparatus.

The outer well 10 is provided with nutrient medium for the tissue equivalent. Such media are known in the art. Preferred serum free nutrient media are disclosed in co-pending U.S. Pat. No. 361,041. The volume of medium must be selected to fill the outer container 14 to an appropriate level so as not to build up a head of pressure which would force the medium through the permeable member 24, the hydrated collagen gel 25, the tissue equivalent 26, 28, into the inner container 20.

In some embodiments of the present invention, the outer container 10 is provided with an absorbent member 32 which is disposed in the outer container 10 so as to contact the outer surface of the permeable member 24. The absorbent member 32 must be compatible with living tissue equivalents. Preferred materials for the absorbent member include cotton, polyester and rayon. A particularly preferred material is absorbent cotton. In general, it is preferred that the absorbent member be free of additives such as detergents.

In other embodiments of the present invention, the outer well 10 is provided with a gel (not shown), such as agarose, which serves to trap the medium. Because the agarose gel can be added up to just below the level of the openings 21, a greater amount of nutrient medium is made available to the tissue equivalent and nutrient supply to the tissue equivalent 26, 28 is not exhausted as quickly. The use of such gels provides benefits in storing and shipping the apparatus of the present invention in terms of minimizing leakage of the media and resultant potential contamination of the tissue equivalent.

The outer 10 and inner 20 containers may be made of any desired material which does not react with or have an undesirable effect on the components of the assay, including the tissue equivalent. For example, the casting mixture for the living tissue equivalent must not adhere to the walls of the inner container during contraction so as to interfere with formation of the tissue equivalent.

It has been found that methods used to sterilize the inner container 20 may impact adherence of the tissue equivalent. For example, the forming tissue will adhere to polystyrene, one preferred material for the inner container, when it is sterilized by electron beam but not when it is sterilized by ethylene oxide. In contrast, K-RESIN® butadiene-styrene polymer, an alloy of polystyrene and butadiene and a particularly preferred material for the inner container, may be sterilized by electron beam without causing the forming tissue equivalent to adhere. (K-RESIN® butadiene-styrene polymer is a trademark of Phillips Petroleum.) In some embodiments, it is desirable that the containers be made so that the tissue equivalent is visible through the container, e.g., through the walls of the container or through a window in the container. Preferred materials for the container 10 include polystyrene and PETG.

The inner container 20 may be of any shape and volume which will accommodate the size and shape of the desired tissue equivalent. The dimensions of the container will again depend upon the size and shape of the desired tissue equivalent and the desired assay volumes. For example, a container having an outer diameter of about 25 mm and a volume of about 5 ml is useful in practicing the present invention. In the embodiment shown in FIGS. 13-15, multiple containers are provided in a base or holder.

The permeable member 24 must have sufficient strength to support the acellular, hydrated collagen gel 25 and the tissue equivalent 26, 28. Porous membranes are useful in the practice of the present invention. The pore size of such membranes is selected so as to provide attachment for the acellular, hydrated collagen gel 25. Preferred membranes are hydrophylic, have a thickness of about 1 to 10 mm, and pore diameters ranging from about 1 to about 10.mu. Preferred materials for the permeable member 24 include polycarbonate. A particularly preferred permeable member is a polycarbonate membrane, preferably free of wetting agents, commercially available from Nuclepore and having a pore size of about 3 to 10.mu.

The sealing means 30 may be made of any material which is inert to the conditions of the assay and the tissue equivalents being used, as well as provides a good seal between the inner container 20 and the tissue equivalent. Preferred materials include polyethylene, TEFLON® PTFE Polytetrafluoroethylene, a trademark of E.I. Du Pont de Nemours and Company, polycarbonate and nylon. The sealing means is especially useful where it is desired to keep the contents of the outer container separated from any solution or substance applied to the epidermis 25, e.g., when measuring the diffusion or permeation of a substance through a tissue equivalent.

Both the tissue equivalents and the acellular, hydrated collagen gel in accordance with the present invention may be prepared using collagen derived from skin and tendon, including rat tail tendon, calf skin collagen, and calf extensor tendon. Other sources of collagen would be suitable. A particularly preferred collagen composition derived from calf common digital extensor tendon and methods of deriving such collagen compositions are disclosed in co-pending U.S. patent application Ser. No. 07/407,465 filed Feb. 9, 1994, the disclosure of which is incorporated herein by reference.

In one method of the present invention, an acellular, hydrated collagen gel 25 is prepared from a collagen composition comprising collagen at about 0.5 to 2.0 mg/ml, preferably about 0.9 to 1.1 mg/ml and nutrient media. This collagen composition is added to the inner container 20 and maintained under conditions which permit the collagen composition to set and form an acellular, hydrated collagen gel of suitable dimensions, typically about 1 to 5 mm thick, a preferred thickness range being about 2 to about 3 mm. An acellular, hydrated collagen gel 25 is preferably thick enough so that a portion remains acellular as cells migrate from the tissue equivalent into an acellular, hydrated collagen gel and thin enough so that the tissue equivalent is not undesirably removed from the nutrient source provided in outer container 10.

A dermal equivalent is next cast on an acellular, hydrated collagen gel using procedures in accordance with the patents and as described hereinafter. A casting mixture containing collagen and fibroblasts is added to inner container 20 over an acellular, hydrated collagen gel 25 and maintained under conditions which enable the tissue equivalent to form. As the tissue equivalent forms on an acellular, hydrated collagen gel 25, it contracts radially. However, an acellular, hydrated collagen gel 25 prevents excessive radial contraction of the tissue equivalent without the need of mechanical restraining means such as textured metals and plastics or VELCRO® Hook and Loop Fasteners, a trademark of Velcro Corporation.

Figure 6:
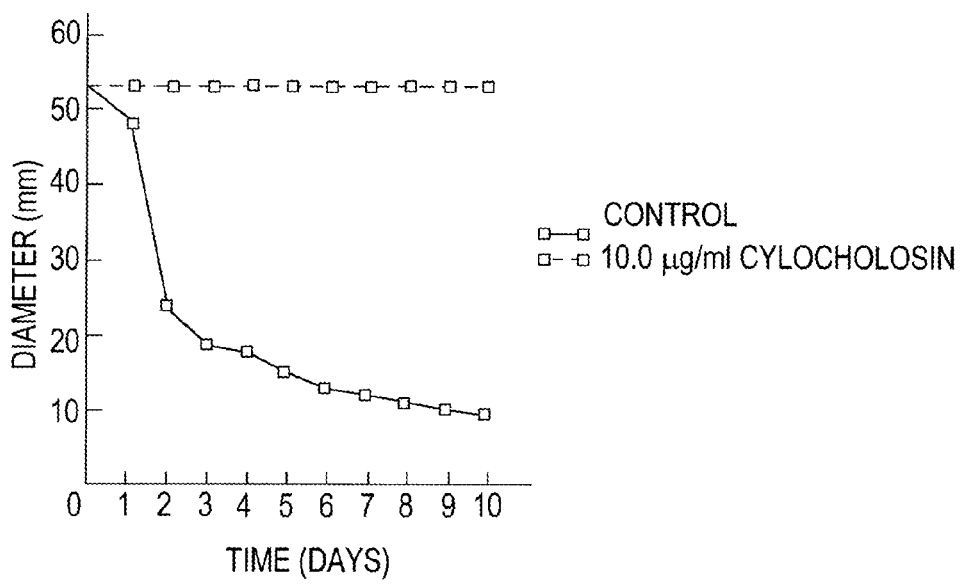
FIG. 6 is a plot of data illustrating the effect of 10.0 .mu.g/ml of the inhibitor cytochalasin B on the capacity of fibroblast cells to contract a hydrated collagen lattice.

Typically, the sides of the tissue equivalent 26 slope towards the outer periphery of hydrated collagen gel 25 to form a mesa as shown in FIGS. 15 and 6 at 52. The tissue equivalent 26 is now seeded with epithelial cells to form the epidermal layer 28. The epidermal cells are seeded in culture medium at a concentration of at about $0.3 \times 10^6$ to $30 \times 10^6$ cells/ml. The volume of epidermal cells seeded will depend upon the size of the mesa.

The concentration of collagen, the number of cells and the volume of the casting mixture can be controlled to optimize the diameter and thickness of the living tissue equivalent. The casting mixture comprises cells at a concentration of about 1.25 to $5 \times 10^4$ cells/ml and collagen at about 0.5 to 2.0 mg/ml in a nutrient medium. A preferred cell concentration is about $2.5 \times 10^4$ cells/ml. It has been found that the ratio of the volume of the casting mixture for the tissue equivalent to the volume of the casting mixture for the acellular, hydrated collagen gel has an effect upon cell viability and differentiation. Useful ratios, v/v, of tissue equivalent casting mixture to collagen gel casting mixture are about 3:1 to 1:3. A preferred ratio wherein the cell concentration in the collagen lattice is at about $2.5 \times 10^4$ cells/ml is 3:1.

The invention will be further understood with reference to the following examples, which are purely exemplary in nature, and are not meant to be utilized to limit the scope of the invention.

Materials used in the following examples were obtained from the sources indicated in the examples or made in accordance with the indicated publications. Sterile procedures were used throughout the Examples. The tissue equivalents were maintained under 10% $CO_2$ in the incubator and sterile procedures were used throughout.

The following examples are provided to better explain the practice of the present invention and should not be interpreted in any way to limit the scope of the present invention. Those skilled in the art will recognize that various modifications can be made to the methods described herein while not departing from the spirit and scope of the present invention.

EXAMPLES

Example 1: Formation of a Collagenous Matrix by Human Neonatal Foreskin Fibroblasts Human neonatal foreskin fibroblasts (originated at Organogenesis, Inc. Canton, Mass.) were seeded at $5 \times 10^5$ cells/162 $cm^2$ tissue culture treated flask (Costar Corp., Cambridge, Mass., cat #3150) and grown in growth medium. The growth medium consisted of: Dulbecco's Modified Eagle's medium (DMEM) (high glucose formulation, without L-glutamine, BioWhittaker, Walkersville, Md.) supplemented with 10% newborn calf serum (NBCS) (HyClone Laboratories, Inc., Logan, Utah) and 4 mM L-glutamine (BioWhittaker, Walkersville, Md.). The cells were maintained in an incubator at 37±1° C. with an atmosphere of 10±1% $CO_2$. The medium was replaced with freshly prepared medium every two to three days. After 8 days in culture, the cells had grown to confluence, that is, the cells had formed a packed monolayer along the bottom of the tissue culture flask, and the medium was aspirated from the culture flask. To rinse the monolayer, sterile-filtered phosphate buffered saline was added to the bottom of each culture flask and then aspirated from the flasks. Cells were released from the flask by adding 5 mL trypsin-versene glutamine (BioWhittaker, Walkersville, Md.) to each flask and gently rocking to ensure complete coverage of the monolayer. Cultures were returned to the incubator. As soon as the cells were released 5 ml of SBTI (Soybean Trypsin Inhibitor) was added to each flask and mixed with the suspension to stop the action of the trypsin-versene. The cell suspension was removed from the flasks and evenly divided between sterile, conical centrifuge tubes. Cells were collected by centrifugation at approximately 800-1000×g for 5 minutes.

Cells were resuspended using fresh medium to a concentration of $3.0 \times 10^6$ cells/ml, and seeded onto 0.4 micron pore size, 24 mm diameter tissue culture treated inserts (TRANSWELL®, Corning Costar) in a six-well tray at a density of $3.0 \times 10^6$ cells/insert ($6.6 \times 10^5$ cells/cm$^2$). The cells were maintained in an incubator at 37±1° C. with an atmosphere of 10±1% $CO_2$ and fed fresh production medium every 2 to 3 days for 21 days. The production medium comprised: a 3:1 base mixture of DMEM and Hams F-12 medium (Quality Biologics Gaithersburg, Md.), 4 mM GlutaMAX-1™ (Gibco BRL, Grand Island, N.Y.) and additives to a resultant concentration of: 5 ng/ml human recombinant epidermal growth factor (Upstate Biotechnology Lake Placid, N.Y.), 2% newborn calf serum (Hyclone, Logan, Utah), 0.4 µg/ml hydrocortisone (Sigma St. Louis, Mo.), $1 \times 10^{-4}$ M ethanolamine (Fluka, Ronkonkoma, N.Y. ACS grade), $1 \times 10^{-4}$ M o-phosphoryl-ethanolamine (Sigma, St. Louis), 5 µg/ml insulin (Sigma, St. Louis, Mo.), 5 µg/ml transferrin (Sigma, St. Louis, Mo.), 20 pM triiodothyronine (Sigma, St. Louis, Mo.), and 6.78 ng/ml selenium (Sigma Aldrich Fine Chemicals Co., Milwaukee, Wis.), 50 ng/ml L-ascorbic acid (WAKO Chemicals USA, Inc.#013-12061), 0.2 µg/ml L-proline (Sigma, St. Louis, Mo.), 0.1 µg/ml glycine (Sigma, St. Louis, Mo.) and 0.05% poly-ethylene glycol (PEG) 3400-3700 MW (cell culture grade) (Sigma, St. Louis, Mo.).

Samples for histological analysis were taken at days 7, 14 and 21 and fixed in formalin, then embedded in paraffin. The formalin fixed samples were embedded in paraffin and 5 micrometer section were stained with hematoxylin-eosin (H&E) according to procedures known in the art. Using H&E stained slides, thickness measurements were made to ten randomly picked microscopic fields utilizing a 10× eyepiece loaded with a 10 mm/100 micrometer reticle.

Results for two different cell strains of human dermal fibroblasts are summarized in Table 1, which shows the thickness of the cell-matrix construct as it develops.

TABLE 1

| | Thickness (microns) | | | |
|---|---|---|---|---|
| | Day 0 | Day 7 | Day 14 | Day 21 |
| B119 Average (n = 3) | 0 | 30.33 ± 2.61 | 63.33 ± 4.40 | 84.00 ± 4.67 |
| B156 Average (n = 4) | 0 | 42.00 ± 5.14 | 63.85 ± 4.50 | 76.25 ± 8.84 |

Samples were also submitted for collagen concentration analysis on days 7, 14, and 21. Collagen content was estimated by employing a calorimetric assay for hydroxyproline content known in the art (Woessner, 1961). At those same timepoints cell number was also determined. Table 2 is a summary of collagen concentration and Table 3 is a summary of the cell data from cell-matrix constructs produced from two different cell strains (B156 and B119) using the procedure described above.

TABLE 2

| | Collagen (µg/cm$^2$) | | | |
|---|---|---|---|---|
| | Day 0 | Day 7 | Day 14 | Day 21 |
| B119 Average (n = 3) | 0 | 93.69 ± 22.73 | 241.66 ± 21.08 | 396.30 ± 29.38 |
| B156 Average (n = 3) | 0 | 107.14 ± 17.16 | 301.93 ± 23.91 | 457.51 ± 25.00 |

TABLE 3

| | Cells (cells/cm$^2$) | | | |
|---|---|---|---|---|
| | Day 0 | Day 7 | Day 14 | Day 21 |
| B119 Average (n = 3) | $6.6 \times 10^5$ | $11.8 \pm 4.4 \times 10^5$ | $11.4 \pm 1.7 \times 10^5$ | $13.9 \pm 1.2 \times 10^5$ |
| B156 Average (n = 3) | $6.6 \times 10^5$ | $13.1 \pm 0.5 \times 10^5$ | $14.0 \pm 2.1 \times 10^5$ | $17.1 \pm 1.7 \times 10^5$ |

Samples of the human cell derived dermal matrix from days 7, 14, and 21 were analyzed by delayed reduction SDS-PAGE to determine collagen composition revealing type I and type III collagen alpha bands in the samples.

Biochemical characteristics of the dermal matrix were determined using immunohistochemical methods. Fibronectin identification was carried out on paraffin fixed sections using the Zymed Histostain strepavidin-biotin system (Zymed Laboratories Inc., South San Francisco, Calif.). Tenascin presence was determined by primary anti-tenascin antibody staining (Dako, Carpintheria, Calif.) followed by anti-mouse horseradish peroxidase labeled antibody (Calbiochem) as a secondary antibody. Samples were visualized by applying diaminobenzyne (Sigma St. Louis, Mo.) and counterstained with Nuclear Fast red.

Glycosaminoglycan (GAG) quantification was performed on 21 day samples using the previously described method (Farndale, 1986). The assay showed the presence of 0.44 grams of GAG per $cm^2$ in a sample of human cell derived dermal matrix taken 21 days post seeding.

Example 2: Full Thickness Skin Construct

Using a dermal construct formed using the method described in Example 1, normal human neonatal foreskin epidermal keratinocytes (originated at Organogenesis, Inc. Canton, Mass.) were plated onto the cell-matrix construct to form the epidermal layer of the skin construct.

The medium was aseptically removed from the culture insert and its surrounds. Normal human epidermal keratinocytes were scaled up to passage 4 from frozen subculture cell stock to confluence. Cells were then released from the culture dishes using trypsin-versene, pooled, centrifuged to form a cell pellet, resuspended in epidermalization medium, counted and seeded on top of the membrane at a density of $4.5 \times 10^4$ cells/$cm^2$. The constructs are then incubated for 90 minutes at $37 \pm 1°$ C., 10% $CO_2$ to allow the keratinocytes to attach. After the incubation, the constructs were submerged in epidermalization medium. The epidermalization medium is composed of: a 3:1 base mixture of Dulbecco's Modified Eagle's Medium (DMEM) (high glucose formulation, without L-glutamine (BioWhittaker, Walkersville, Md.) and Hams F-12 medium (Quality Biologics Gaithersburg, Md.), supplemented with 0.4 µg/ml hydrocortisone (Sigma St. Louis, Mo.), $1 \times 10^{-4}$ M ethanolamine (Fluka, Ronkonkoma, N.Y.), $1 \times 10^{-4}$ M O-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), 6.78 ng/ml selenium (Aldrich), 24.4 µg/ml adenine (Sigma Aldrich Fine Chemicals Company, Milwaukee, Wis.), 4 mM L-glutamine (BioWhittaker, Walkersville, Md.), 0.3% chelated new born calf serum (Hyclone, Logan, Utah), 0.628 ng/ml progesterone (Amersham Arlington Heights, Ill.), 50 µg/ml L-ascorbate sodium salt (Sigma Aldrich Fine Chemicals Company, Milwaukee, Wis.), 10 ng/ml epidermal growth factor (Life Technologies Inc., MD), and 50 µg/ml gentamycin sulfate (Amersham, Arlington Heights, Ill.). The constructs were cultured in the epidermalization medium for 2 days at $37 \pm 1°$ C., 10% $CO_2$.

After 2 days the construct was submerged in media composed of, 3:1 mixture of Dulbecco's modified Eagle's medium (DMEM) (high glucose formulation, without L-glutamine, BioWhittaker, Walkersville, Md.), Hams F-12 medium (Quality Biologics, Gaithersburg, Md.), supplemented with 0.4 µg/ml hydrocortisone (Sigma St. Louis, Mo.), $1 \times 10^{-4}$ ethanolamine (Fluka, Ronkonkoma, N.Y.), $1 \times 10^{-4}$ o-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), and 6.78 ng/ml selenium (Sigma Aldrich Fine Chemicals Company, Milwaukee, Wis.), 24.4 µg/ml adenine (Sigma Aldrich Fine Chemicals Company), 4 mM L-glutamine (BioWhittaker, Walkersville, Md.), 0.3% chelated new born calf serum (BioWhittaker, Walkersville, Md.), 0.628 ng/ml progesterone (Amersham, Arlington Heights, Ill.), 50 µg/ml sodium ascorbate, 265 µg/ml calcium chloride (Mallinckrodt, Chesterfield, Mo.), and 50 µg/ml gentamycin sulfate (Amersham, Arlington Heights, Ill.). Again the construct was incubated at $37 \pm 1°$ C., 10% $CO_2$ for 2 days.

After the 2 days the carrier containing the construct was aseptically transferred to new culturing trays with a sufficient amount cornification media, 9 mL, to achieve a fluid level just to the surface of the carrier membrane to maintain a dry interface to allow stratification of the epithelial layer. The constructs were incubated at $37 \pm 1°$ C., 10% $CO_2$, and low humidity, in media with media changes every 2-3 days for 7 days. This medium is composed of, a 1:1 mixture of Dulbecco's modified Eagle's medium (DMEM) (high glucose formulation, without L-glutamine BioWhittaker, Walkersville, Md.), Hams F-12 medium (Quality Biologics, Gaithersburg, Md.), supplemented with 0.4 µg/ml hydrocortisone (Sigma, St. Louis, Mo.), $1 \times 10^{-4}$ M ethanolamine (Fluka, Ronkonkoma, N.Y.), $1 \times 10^{-4}$ M O-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 µM triiodothyronine (Sigma, St. Louis, Mo.), 6.78 ng/ml selenium (Aldrich), 24.4 µg/ml adenine (Sigma Aldrich Fine Chemicals Company), 4 mM L-glutamine (BioWhittaker, Walkersville, Md.), 2% new born calf serum (BioWhittaker, Walkersville, Md.), 50 µg/ml sodium ascorbate, and 50 µg/ml gentamycin sulfate (Amersham, Arlington Heights, Ill.). After 7 days the construct was fed for 10 more days, with changes every 2-3 days with a maintenance medium. This maintenance medium was composed of, 1:1 mixture of Dulbecco's modified Eagle's medium (DMEM) (high glucose formulation, without L-glutamine, BioWhittaker, Walkersville, Md.), Hams F-12 medium (Quality Biologics Gaithersburg, Md.), 0.4 µg/ml hydrocortisone (Sigma St. Louis, Mo.), $1 \times 10^{-4}$ M ethanolamine (Fluka, Ronkonkoma, N.Y.), $1 \times 10^{-4}$ M o-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 µM triiodothyronine (Sigma, St. Louis, Mo.), and 6.78 ng/ml selenium (Sigma Aldrich Fine Chemicals Company, Milwaukee, Wis.), 24.4 µg/ml adenine (Sigma Aldrich Fine Chemicals Company, Milwaukee, Wis.), 4 mM L-glutamine (BioWhittaker, Walkersville, Md.), 1% new born calf serum (BioWhittaker, Walkersville, Md.), and 50 µg/ml gentamycin sulfate (Amersham, Arlington Heights, Ill.).

Final samples were submitted for hemotoxylin and eosin processing as described in Example 1 to determine gross appearance under light microscopy. The resulting construct consisted of a lower (dermal) layer consisting of fibroblasts surrounded by matrix having features described in Example 1, and was completely overlaid by a multilayered, stratified and well-differentiated layer of keratinocytes that exhibit a basal layer, a suprabasal layer, a granular layer and a stratum corneum similar to that of skin in situ. The skin construct has a well-developed basement membrane present at the dermal-epidermal junction as exhibited by transmission electron microscopy (TEM). The basement membrane appears thickest around hemidesmosomes, marked by anchoring fibrils that are comprised of type VII collagen, as visualized by TEM. As expected these anchoring fibrils can easily be seen exiting from the basement membrane and entrapping the collagen fibrils. The presence of laminin, a basement membrane glycoprotein, was shown using the previously described avidin-biotin immunoenzymatic technique (Guesdon, 1979).

Example 3: In Vitro Formation of a Collagenous Matrix by Human Neonatal Foreskin Fibroblasts in Chemically Defined Medium Human neonatal foreskin fibroblasts were expanded using the procedure described in Example 1. Cells were then resuspended to a concentration of $3\times10^6$ cells/ml, and seeded on to 0.4 micron pore size, 24 mm diameter tissue culture treated membrane inserts in a six-well tray at a density of $3.0\times10^6$ cells/TW ($6.6\times10^5$ cells/cm$^2$). These cells were then maintained as Example 1 with newborn calf serum omitted from the media throughout. More specifically the medium contained: a base 3:1 mixture of DMEM, Hams F-12 medium (Quality Biologics, Gaithersburg, Md.), 4 mM GlutaMAX (Gibco BRL, Grand Island, N.Y.) and additives: 5 ng/ml human recombinant epidermal growth factor (Upstate Biotechnology, Lake Placid, N.Y.), 0.4 µg/ml hydrocortisone (Sigma, St. Louis, Mo.), $1\times10^{-4}$ M ethanolamine (Fluka, Ronkonkoma, N.Y. cat. #02400 ACS grade), $1\times10^{-4}$ M O-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), and 6.78 ng/ml selenium (Sigma Aldrich Fine Chemicals Company, Milwaukee, Wis.), 50 ng/ml L-ascorbic acid (WAKO Chemicals USA, Inc.), 0.2 µg/ml L-proline (Sigma, St. Louis, Mo.), 0.1 µg/ml glycine (Sigma, St. Louis, Mo.) and 0.05% poly-ethylene glycol (PEG) (Sigma, St. Louis, Mo.). Samples were checked at day 7, 14, and 21 for collagen concentration and cell number using described procedures. Results are summarized in tables 4 (cell number) and 5 (collagen). Samples were also formalin fixed and processed for hemotoxylin and eosin staining for light microscope analysis as described in Example 1. Histological evaluation demonstrated that the constructs grown in defined medium was similar to those grown in the presence of 2% newborn calf serum. Samples also stained positively for fibronectin, using procedure described in Example 1.

TABLE 4

| | Collagen (µg/cm$^2$) | | | |
|---|---|---|---|---|
| | Day 0 | Day 7 | Day 14 | Day 21 |
| Average amount of collagen in each construct (n = 3) | 0 | 107.63 ± 21.96 | 329.85 ± 27.63 | 465.83 ± 49.46 |

TABLE 5

| | Cells (cells/cm$^2$) | | | |
|---|---|---|---|---|
| | Day 0 | Day 7 | Day 14 | Day 21 |
| Average number of cells in each construct (n = 3) | $6.6 \times 10^5$ | $7.8 \pm 2.2 \times 10^5$ | $9.6 \pm 2.5 \times 10^5$ | $1.19 \pm 2.1 \times 10^5$ |

Besides endogenously produced fibrillar collagen, decorin and glycosaminoglycan were also present in the cell-matrix construct.

Example 4: Full Thickness Skin Construct Formed Using Chemically Defined Media

Using a 25 day dermal construct formed by human dermal fibroblasts under chemically defined conditions similar to the method described in Example 3, normal human neonatal foreskin epidermal keratinocytes were seeded on the top surface of the cell-matrix construct to form the epidermal layer of the skin construct.

The medium was aseptically removed from the culture insert and its surrounds. Normal human epidermal keratinocytes were scaled up to passage 4 from frozen subculture cell stock to confluence. Cells were then released from the culture dishes using trypsin-versene, pooled, centrifuged to form a cell pellet, resuspended in epidermalization medium, counted and seeded on top of the membrane at a density of $4.5\times10^4$ cells/cm$^2$. The constructs were then incubated for 90 minutes at 37±1° C., 10% CO$_2$ to allow the keratinocytes to attach. After the incubation, the constructs were submerged in epidermalization medium. The epidermalization medium is composed of: a 3:1 base mixture of Dulbecco's Modified Eagle's Medium (DMEM) (containing no glucose and no calcium, BioWhittaker, Walkersville, Md.) and Hams F-12 medium (Quality Biologics Gaithersburg, Md.), supplemented with 0.4 µg/ml hydrocortisone (Sigma St. Louis, Mo.), $1\times10^{-4}$ M ethanolamine (Fluka, Ronkonkoma, N.Y.), $1\times10^{-4}$ M o-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), 6.78 ng/ml selenium (Aldrich), 24.4 µg/ml adenine (Sigma Aldrich Fine Chemicals Company, Milwaukee, Wis.), 4 mM L-glutamine (BioWhittaker, Walkersville, Md.), 50 µg/ml L-ascorbate sodium salt (Sigma Aldrich Fine Chemicals Company, Milwaukee, Wis.), 16 µM linoleic acid (Sigma, St. Louis, Mo.), 1 µM tocopherol Acetate (Sigma, St. Louis, Mo.) and 50 µg/ml gentamicin sulfate (Amersham, Arlington Heights, Ill.). The constructs were cultured in the epidermalization medium for 2 days at 37±1° C., 10±1% CO$_2$.

After 2 days the medium was exchanged with fresh medium composed as above, and returned to the incubator set at 37±1° C., 10±1% CO$_2$ for 2 days. After the 2 days, the carrier containing the construct was aseptically transferred to new culturing trays with sufficient media to achieve a fluid level just to the surface of the carrier membrane to maintain the developing construct at the air-liquid interface. The air contacting the top surface of the forming epidermal layer allows stratification of the epithelial layer. The constructs were incubated at 37±1° C., 10% CO$_2$, and low humidity, in media with media changes every 2-3 days for 7 days. This medium contained a 1:1 mixture of Dulbecco's modified Eagle's medium (DMEM) (containing no glucose and no calcium, BioWhittaker, Walkersville, Md.), Hams F-12 medium (Quality Biologics, Gaithersburg, Md.), supplemented with 0.4 µg/ml hydrocortisone (Sigma, St. Louis, Mo.), $5\times10^{-4}$ M ethanolamine (Fluka, Ronkonkoma, N.Y.), $5\times10^{-4}$ M o-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), 6.78 ng/ml selenium (Sigma Aldrich Fine Chemicals Company), 24.4 µg/ml adenine (Sigma Aldrich Fine Chemicals Company), 4 mM L-glutamine (BioWhittaker, Walkersville, Md.), 2.65 µg/ml calcium chloride (Mallinckrodt, Chesterfield, Mo.), 16 µM linoleic acid (Sigma, St. Louis, Mo.), 1 µM tocopherol acetate (Sigma, St. Louis, Mo.), 1.25 mM serine (Sigma, St. Louis, Mo.), 0.64 mM choline chloride (Sigma, St. Louis, Mo.) and 50 µg/ml gentamicin sulfate (Amersham, Arlington Heights, Ill.). The cultures were fed every 2-3 days, for 14 days.

Samples, in triplicate, were submitted 10, 12, and 14 days after the construct was lifted to the air-liquid interface for hematoxylin and eosin processing as described in Example 1 to determine gross appearance under light microscopy. The resulting construct consisted of a lower (dermal) layer consisting of fibroblasts surrounded by matrix having features as described in Example 3, and was overlaid by a layer of stratified and differentiated keratinocytes.

Example 5: In Vitro Formation of a Collagenous Matrix by Human Achilles Tendon Fibroblasts Cell-matrix constructs were formed using the same method described in Example 1 replacing the human neonatal foreskin fibroblasts with human Achilles tendon fibroblasts (HATF.). Following 21 days in production medium, samples were also submitted for H&E staining and thickness determination using the procedure described in Example 1. The resulting construct was visualized as a cell matrix tissue like construct with a thickness of 75.00±27.58 microns (n=2). Endogenously produced fibrillar collagen, decorin and glycosaminoglycan were also present in the construct.

Example 6: In Vitro Formation of a Collagenous Matrix by Transfected Human Neonatal Foreskin Fibroblasts Transfected human dermal fibroblasts were produced using the following procedure. One vial of jCRIP-43 platelet derived growth factor (PDGF) viral producers (Morgan, J, et al.) was thawed, and the cells were seeded at $2\times10^6$ cells/162 cm$^2$ flask (Corning Costar, Cambridge, Mass.). These flasks were fed a growth medium, and maintained in an incubator at 37±1° C. with an atmosphere of 10±1% $CO_2$. The growth medium consisted of: Dulbecco's modified Eagle's medium (DMEM) (high glucose formulation, without L-glutamine, BioWhittaker, Walkersville, Md.) supplemented with 10% newborn calf serum (HyClone Laboratories, Inc., Logan, Utah) and 4 mM L-glutamine (BioWhittaker, Walkersville, Md.). On the same day, 1 vial of human neonatal foreskin fibroblast (HDFB156) was also thawed and plated at 1.5×$10^6$ cells/162 cm$^2$ flask (Corning Costar, Cambridge, Mass.). After three days the jCRIP PDGF-43 viral producers were fed with fresh growth medium. The HDFB156 were fed with the above growth medium plus 8 µg/ml polybrene (Sigma, St. Louis, Mo.). The next day the HDFB156's cells were infected as follows. The spent medium from the jCRIP PDGF-43 viral producers was collected and filtered through a 0.45 micron filter. 8 µg/ml polybrene was added to this filtered spent medium. The spent medium was then placed on the HDF. On the next two days the HDF were fed fresh growth medium. The day after the HDF were passed from p5 to p6 and seeded at a density of $2.5\times10^6$ cells/162 cm$^2$ flask (Corning Costar, Cambridge, Mass.). Cells were passed as follows; spent medium was aspirated off. The flasks were then rinsed with a phosphate buffered saline to remove any residual newborn calf serum. Cells were released from the flask by adding 5 mL trypsin-versene to each flask and gently rocking to ensure complete coverage of the monolayer. Cultures were returned to the incubator. As soon as the cells were released, 5 mL of SBTI (Soybean Trypsin Inhibitor) was added to each flask and mixed with the suspension to stop the action of the trypsin-versene. The cell/Trypsin/SBTI suspension was removed from the flasks and evenly divided between sterile, conical centrifuge tubes. Cells were collected by centrifugation at approximately 800-1000×g for 5 minutes). The cells were resuspended in the growth media for seeding at the density listed above. After two days the cells were fed fresh growth medium. The following day the cells were harvested as above, and diluted to a density of $1.5\times10^6$ cells/ml in growth medium containing 10% newborn calf serum (NBCS) with 10% dimethyl sulfoxide (DMSO) (Sigma, St. Louis, Mo.). The cells were then frozen 1 ml/cryovial at about −80° C.

Production of the collagenous matrix for this example utilize the same procedure as Examples 1 and 3, replacing the human neonatal foreskin fibroblasts with human neonatal foreskin fibroblasts transformed to produce high levels of platelet derived growth factor (PDGF) as described above. Samples were taken for H&E staining as described above on day 18 post seeding. Samples were also stained using the avidin-biotin methods for the presence of fibronectin listed in Example 10. Samples were taken on day 18 post seeding for H&E staining as described in Example 1, and exhibited a similar cell-matrix gross appearance to that described in Example 1, with a measured thickness of 123.6 microns (N=1). PDGF output of the transfected cells in the cell-matrix construct was measured to be 100 ng/mL by ELISA throughout the duration of the culture (18 days) while control output of PDGF was undetectable.

Example 7: Use of the Dermal Construct as a Graft Material

Cell-matrix constructs were prepared according to the methods in Example 1 using human dermal fibroblasts derived from neonate foreskin and were grafted onto full excision wounds created on nude athymic mice. Mice were grafted according to the methods described by Parenteau, et al. (1996), the disclosure of which is incorporated herein. Grafts were examined at 14, 28 and 56 days for signs of adherence to the wound bed, evidence of wound contraction, areas of graft loss, and presence of vascularization (color). The graft areas were photographed while intact on the mice. A number of mice were sacrificed at each timepoint, and the graft areas and their surrounds were excised along with a surrounding rim of murine skin to at least the panniculus carnosus. Junctions between the graft and the murine skin were preserved in each sample. The explanted tissue samples were then fixed in phosphate buffered 10% formalin and fixation in methanol. Formalin fixed samples were processed for H&E staining according to procedure described in Example 1. Grafts were able to integrate with the mouse skin, with minimal contraction noted. Within 14 days of grafting, the mouse epidermis had migrated completely over the graft. Using the H&E stained samples, vessels were obvious within the graft at 14 days, and throughout the experiment. By gross observation and by H&E stained samples, it was determined that the graft persisted and remained healthy looking contained living cells, no gross matrix abnormalities, etc.) throughout the length of the experiment.

Example 8: Use of Full Thickness Skin Construct as a Skin Graft

Bilayer skin constructs were prepared as described in Example 2 using human dermal fibroblasts derived from neonate foreskin in the dermal layer and human keratinocytes derived from a different neonate foreskin in the epidermal layer. The skin constructs were able to be manually peeled from the membrane, handled without carrier support, and placed onto the graft site. The bilayer skin constructs were grafted onto full excision wounds created on athymic nude mice according to the methods described by Parenteau, et al. (1996), the disclosure of which is incorporated herein. Timepoints for taking samples were days 7, 14, 28, 56, and 184 days post-graft. The graft areas were photographed while intact on the mice. A number of mice were sacrificed at each timepoint, and the graft areas and their surrounds were excised along with a surrounding rim of murine skin to at least the panniculus carnosus. Junctions between the graft and the murine skin were preserved in each sample. The explanted tissue samples were then fixed in phosphate buffered 10% formalin and fixation in methanol. Formalin fixed samples were processed for H&E staining according to procedure described in Example 1.

The grafts integrated with the host tissue within 7 days by gross observation as well as by histological appearance. By H&E staining, vessels were visualized growing into the graft from the host tissue within 7 days of grafting. The grafts remained healthy and persisted through the experiment, with minimal contraction noted. Utilizing anti-human Involucrin staining the persistence of human epidermal cells was shown for the entire graft period.

Example 9: In Vitro Formation of a Matrix by Human Corneal Keratocytes

Human corneal keratocyte cells (originated at Organogenesis, Inc. Canton, Mass.) were used in the production of a stromal construct of cornea. Confluent cultures of human keratocytes were released from their culture substrates using trypsin-versene. When released, soybean trypsin inhibitor was used to neutralize the trypsin-versene, the cell suspension was centrifuged, the supernatant discarded and the cells were then resuspended in base media to a concentration of $3\times10^6$ cells/ml. Cells were seeded onto 0.4 micron pore size, 24 mm diameter tissue culture treated transwells in a six-well tray at a density of $3.0\times10^6$ cells/TW ($6.6\times10^5$ cells/cm$^2$). These cultures were maintained overnight in seed medium. The seed medium was composed of: a base 3:1 mixture of Dulbecco's Modified Eagle's Medium (DMEM) and Hams F-12 Medium (Quality Biologics Gaithersburg, Md. cat.), 4 mM GlutaMAX (Gibco BRL, Grand Island, N.Y.) and additives: 5 ng/ml human recombinant epidermal growth factor (EGF) (Upstate Biotechnology Lake Placid, N.Y.), 0.4 µg/ml hydrocortisone (Sigma St. Louis, Mo.), $1\times10^{-4}$ M ethanolamine (Fluka, Ronkonkoma, N.Y.), $1\times10^{-4}$ M o-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), and 6.78 ng/ml selenium (Sigma Aldrich Fine Chemicals Company, Milwaukee, Wis.). Following this the cultures were fed fresh production medium. The production medium was composed of: a base 3:1 mixture of DMEM, Hams F-12 medium (Quality Biologics Gaithersburg, Md.), 4 mM GlutaMAX (Gibco BRL., Grand Island, N.Y.) and additives: 5 ng/ml Human Recombinant Epidermal growth factor (Upstate Biotechnology Lake Placid, N.Y.), 2% newborn calf serum (Hyclone, Logan, Utah), 0.4 µg/ml hydrocortisone (Sigma, St. Louis, Mo.), $1\times10^{-4}$ M ethanolamine (Fluka, Ronkonkoma, N.Y. ACS grade), $1\times10^{-4}$ M o-phosphoryl-ethanolamine (Sigma, St. Louis), 5 µg/ml insulin (Sigma, St. Louis, Mo.), 5 µg/ml transferrin (Sigma, St. Louis, Mo.), 20 pM triiodothyronine (Sigma, St. Louis, Mo.), and 6.78 ng/ml selenium (Sigma Aldrich Fine Chemicals Co., Milwaukee, Wis.), 50 ng/ml L-ascorbic acid (WAKO pure chemical company), 0.2 µg/ml L-proline (Sigma, St. Louis, Mo.), 0.1 µg/ml glycine (Sigma, St. Louis, Mo.) and 0.05% poly-ethylene glycol (PEG) (Sigma, St. Louis, Mo., cell culture grade).

The cells were maintained in an incubator at 37±1° C. with an atmosphere of 10%±1% $CO_2$ and fed fresh production medium every 2-3 days for 20 days (for a total of 21 days in culture. After 21 days in culture, the keratocytes had deposited a matrix layer of about 40 microns in thickness, as measured by the method described in Example 1. Endogenously produced fibrillar collagen, decorin and glycosaminoglycan were also present in the cell-matrix construct.

Example 10: In Vitro Formation of a Collagenous Matrix by Human Neonatal Foreskin Fibroblasts Seeded in Production Media Human neonatal foreskin fibroblasts (originated at Organogenesis, Inc. Canton, Mass.) were seeded at $1\times10^5$ cells/0.4 micron pore size, 24 mm diameter tissue culture treated carriers in a six-well tray (TRANSWELL®, Costar Corp. Cambridge, Mass.) and grown in growth medium. The growth medium consisted of: Dulbecco's Modified Eagle's medium (DMEM) (high glucose formulation, without L-glutamine, BioWhittaker, Walkersville, Md.) supplemented with 10% newborn calf serum (HyClone Laboratories, Inc., Logan, Utah) and 4 mM L-Glutamine (BioWhittaker, Walkersville, Md.). The cells were maintained in an incubator at 37±1° C. with an atmosphere of 10±1% $CO_2$. The medium was replaced every two to three days. After 9 days in culture the medium was aspirated from the culture dish, and replaced with production medium. The cells were maintained in an incubator at 37±1° C. with an atmosphere of 10±1% $CO_2$ and fed fresh production medium every 2-3 days for 21 days. The production medium was composed of: a base 3:1 mixture of DMEM, Hams F-12 medium (Quality Biologics, Gaithersburg, Md.), 4 mM GlutaMAX (Gibco BRL, Grand Island, N.Y.) and additives: 5 ng/ml human recombinant epidermal growth factor (Upstate Biotechnology, Lake Placid, N.Y.), 2% newborn calf serum (Hyclone, Logan, Utah), 0.4 µg/ml hydrocortisone (Sigma St. Louis, Mo.), $1\times10^{-4}$ M ethanolamine (Fluka, Ronkonkoma, N.Y. ACS grade), $1\times10^{-4}$ M o-phosphoryl-ethanolamine (Sigma, St. Louis), 5 µg/ml insulin (Sigma, St. Louis, Mo.), 5 µg/ml transferrin (Sigma, St. Louis, Mo.), 20 pM triiodothyronine (Sigma, St. Louis, Mo.), and 6.78 ng/ml selenium (Sigma Aldrich Fine Chemicals Co., Milwaukee, Wis.), 50 ng/ml L-ascorbic acid (WAKO Pure Chemical Company), 0.2 µg/ml L-proline (Sigma, St. Louis, Mo.), 0.1 µg/ml glycine (Sigma, St. Louis, Mo.) and 0.05% poly-ethylene glycol (PEG) (Sigma, St. Louis, Mo., cell culture grade).

Samples were taken at day 21 and fixed in formalin, then embedded in paraffin. The formalin fixed samples were embedded in paraffin and 5 micrometer section were stained with hematoxylin-eosin (H&E) according techniques routinely used in the art. Using H&E stained slides, measurements were made at ten randomly picked microscopic fields utilizing a 10× Eyepiece (Olympus America Inc., Melville, N.Y.) loaded with a 10 mm/100 micrometer reticle (Olympus America Inc., Melville, N.Y.). The constructs created using this method are similar in structure and biochemical composition to those created with Example 1, and have a measured thickness of 82.00±7.64 microns.

Example 11: In Vitro Formation of a Collagenous Matrix by Pig Dermal Fibroblasts Pig Dermal Fibroblasts (originated at Organogenesis, Inc. Canton, Mass.) were seeded at $5\times10^5$ cells/162 cm$^2$ tissue culture treated flask (Costar Corp., Cambridge, Mass. cat #3150) and grown in growth medium as described below. The growth medium consisted of, Dulbecco's modified Eagle's medium (DMEM) (high glucose formulation, without L-glutamine, BioWhittaker, Walkersville, Md.) supplemented with 10% fetal calf serum (HyClone Laboratories, Inc., Logan, Utah) and 4 mM L-glutamine (BioWhittaker, Walkersville, Md.). The cells were maintained in an incubator at 37±1° C. with an atmosphere of 10%±1% $CO_2$. The medium was replaced every two to three days. Upon confluence, that is the cells had formed a packed layer at the bottom of the tissue culture flask, the medium was aspirated from the culture dish. To rinse the monolayer, sterile-filtered phosphate buffered saline was added to the monolayer and then aspirated from the dish. Cells were released from the flask by adding 5 ml trypsin-versene glutamine (BioWhittaker, Walkersville, Md.) to each flask and gently rocking to ensure complete coverage of the monolayer. Cultures were returned to the incubator. As soon as the cells were released 5 ml of SBTI (Soybean Trypsin Inhibitor) was added to each flask and mixed with the cell suspension to stop the action of the trypsin-versene. The suspension was removed from the flasks and evenly divided between sterile, conical centrifuge tubes. Cells were collected by centrifugation at approximately 800-1000×g for 5 minutes. Cells were resuspended and diluted to a concentration of $3\times10^6$ cells/ml, and seeded onto 0.4 micron pore size, 24 mm diameter tissue culture treated transwells in a six-well tray at a density of $3.0\times10^6$ cells/TW ($6.6\times10^5$ cells/cm$^2$). Cells were maintained overnight in a seed medium. The seed medium consisted of, a base 3:1 mixture of DMEM, Hams F-12 medium (Quality Biologics, Gaithersburg, Md.), 4 mM GlutaMAX (Gibco BRL, Grand Island, N.Y.) and additives: 5 ng/ml human recombinant epidermal growth factor (Upstate Biotechnology Lake Placid, N.Y.), 0.4 µg/ml hydrocortisone (Sigma St. Louis, Mo.), $1\times10^{-4}$ M ethanolamine (Fluka, Ronkonkoma, N.Y. ACS grade), $1\times10^{-4}$ M o-phosphoryl-ethanolamine (Sigma, St. Louis), 5 µg/ml insulin (Sigma, St. Louis, Mo.), 5 µg/ml transferrin (Sigma, St. Louis, Mo.), 20 pM triiodothyronine (Sigma, St. Louis, Mo.), and 6.78 ng/ml selenium (Sigma Aldrich Fine Chemicals Co., Milwaukee, Wis.), 50 ng/ml L-ascorbic acid (WAKO Pure Chemical Company), 0.2 µg/ml L-proline (Sigma, St. Louis, Mo.), and 0.1 µg/ml glycine (Sigma, St. Louis, Mo.). The cells were maintained in an incubator at 37±1° C. with an atmosphere of 10±1% $CO_2$ and fed fresh production medium every 2-3 days for 7 days. The production medium was composed of: a base 3:1 mixture of DMEM, Hams F-12 medium (Quality Biologics, Gaithersburg, Md.), 4 mM GlutaMAX (Gibco BRL, Grand Island, N.Y.) and additives: 5 ng/ml human recombinant epidermal growth factor (Upstate Biotechnology, Lake Placid, N.Y.), 2% newborn calf serum (Hyclone, Logan, Utah), 0.4 µg/ml hydrocortisone (Sigma St. Louis, Mo.), $1\times10^{-4}$ M ethanolamine (Fluka, Ronkonkoma, N.Y. ACS grade), $1\times10^{-4}$ M o-phosphoryl-ethanolamine (Sigma, St. Louis), 5 µg/ml insulin (Sigma, St. Louis, Mo.), 5 µg/ml transferrin (Sigma, St. Louis, Mo.), 20 pM triiodothyronine (Sigma, St. Louis, Mo.), and 6.78 ng/ml selenium (Sigma Aldrich Fine Chemicals Co., Milwaukee, Wis.), 50 ng/ml L-ascorbic acid (WAKO Pure Chemical Company), 0.2 µg/ml L-proline (Sigma, St. Louis, Mo.), 0.1 µg/ml glycine (Sigma, St. Louis, Mo.) and 0.05% poly-ethylene glycol (PEG) (Sigma, St. Louis, Mo.) cell culture grade. After 7 days the media was replaced with production medium without newborn calf serum. This media was fed fresh to the cells every 2-3 days for 20 more days, for a total of 28 days in culture.

Samples were taken at day 21 and fixed in formalin, then embedded in paraffin. The formalin fixed samples were embedded in paraffin and 5 micrometer section were stained with hematoxylin-eosin (H&E) according to techniques customarily used in the art. Using H&E stained slides, measurements were made at ten randomly picked microscopic fields utilizing a 10× Eyepiece (Olympus America Inc., Melville, N.Y.) loaded with a 10 mm/100 micrometer reticle (Olympus America Inc., Melville, N.Y.). The sample exhibited a structure composed of cells and matrix with a measured thickness of 71.20±9.57 microns. Besides endogenously produced fibrillar collagen, decorin and glycosaminoglycan were also present in the cell-matrix construct.

Example 12: In Vitro Formation of a Bilayer Skin Construct Containing Cells of Dermal Papilla A cell-matrix was made according to the method in Example 1 using Human Neonatal Foreskin Fibroblasts as a first matrix producing cell type. The cell-matrix was locally seeded with spots of dermal papilla cells as a second cell population which was in turn seeded with keratinocytes as a third cell population, to form a continuous epidermal layer over the cell-matrix and the dermal papilla cells.

First, a cell-matrix construct was formed using human dermal fibroblasts (HDF) derived from neonatal foreskin. HDF were scaled up by seeding them at $5\times10^5$ cells/162 cm$^2$ tissue culture treated flask (Costar Corp., Cambridge, Mass.) in growth medium consisting of: Dulbecco's Modified Eagle's medium (DMEM) (high glucose formulation, without L-glutamine, BioWhittaker, Walkersville, Md.) supplemented with 10% newborn calf serum (NBCS) (HyClone Laboratories, Inc., Logan, Utah) and 4 mM L-glutamine (BioWhittaker, Walkersville, Md.). When confluent, HDF were released from the plate using trypsin-versene and resuspended using fresh medium to a concentration of $3.0\times10^6$ cells/ml, and seeded onto 0.4 micron pore size, 24 mm diameter tissue culture treated inserts (TRANSWELL®, Corning Costar) in a six-well tray at a density of $3.0\times10^6$ cells/insert ($6.6\times10^5$ cells/cm$^2$). HDF cultures were maintained in an incubator at 37±1° C. with an atmosphere of 10±1% $CO_2$ and fed fresh production medium every 2 to 3 days for 23 days according the method detailed in Example 1.

After the cell-matrix construct had formed, it was seeded with spots of dermal papillae cells as a second cell population. Dermal papilla cells are a discrete population of specialized fibroblasts surrounded by the hair bulb of hair follicles to play a support role in the hair growth. Dermal papillae can be isolated by microdissecting hair follicles and cultured in vitro using the method previously described by Messenger, A. G., The Culture of Dermal Papilla Cells from Human Hair Follicles. Br. J. Dermatol. 110: 685-9 (1984), the method of which is incorporated herein. When a culture of dermal papilla cells reach confluence they form aggregates that can be replated on culture flasks to reform new aggregates. Dermal papillae were isolated from a skin biopsy obtained from a 4-week old pig. Cells from the dermal papilla (PDP) were serially cultured in DMEM containing 20% of NBCS until passage 8. After 3 weeks in culture, the PDP cells reformed dermal papilla-like structures, or aggregates, that each had a diameter approximately between 90 to 210 microns. The aggregates were then removed from the culture plate by vigorous pipetting of medium against them, and then seeded onto the Human Collagenous Matrix at the density of 200 aggregates per $cm^2$. The aggregates were cultured submerged for an additional 15 days in DMEM 20% NBCS with spent medium exchanged with fresh medium every 2-3 days.

The cell-matrix cultures containing dermal papilla cells thereon were seeded with keratinocytes and cultured to form a continuous epidermal layer over the cell-matrix and the dermal papillae. Two different constructs were made: the first with human keratinocytes, the second with pig keratinocytes. Normal epidermal keratinocytes were isolated from human neonatal foreskin (HEP), or from pig keratinocytes (PEP) using explant outgrowth to establish primary cultures. These cells were then cultured and expanded until passage 3 for the pig strain, or until passage 4 for the human strain. After about 5 to 6 days in culture, cells were then released from the culture dishes using trypsin-versene, pooled, centrifuged to form a cell pellet, resuspended in epidermalization medium, counted and seeded on top of the membrane at a density of $4.5 \times 10^4$ cells/$cm^2$ for HEP cells, or $1.6 \times 10^5$ cells/$cm^2$ for PEP cells. Epidermalized cultures were cultured for 12 days as previously described in Example 2.

Final samples were submitted for hematoxylin and eosin processing for light microscopy. The resulting skin constructs exhibited the basic morphological organization similar to skin: a dermal layer consisting of fibroblasts surrounded by endogenously produced matrix, including endogenously produced fibrillar collagen, decorin and glycosaminoglycan, localized areas of dermal papilla cells and a continuous, stratified layer of keratinocytes across the cell-matrix construct and the dermal papillae. In both tissue constructs overlaid with either human or pig keratinocytes, the dermal papilla maintained a packed structure that induced small undulations of the overlaid epithelium. Differentiated epithelial cells are often present close to the dermal papilla cells.

Example 13: Hyaluronic Acid Measurement by Sandwich ELISA

Hyaluronic acid (HA) was measured in cell-matrix constructs formed by dermal fibroblasts in serum-containing medium and chemically defined medium according to the methods of Examples 1 and 3, respectively.

Cell-matrix constructs were formed on circular 75 mm diameter carriers incorporating a porous membrane (TRANSWELL®, CorningCostar). Extracts from the cell-matrix constructs were prepared by adding 10 mL ammonium acetate buffer and 0.5 mg/mL Proteinase K to a test-tube containing a cell-matrix construct. The mixture was incubated at 60° C. overnight. After completion of digestion, the mixture was spun down and the supernatant extract was transferred to a separate tube for hyaluronic acid assay. A 96-well plate was coated with 50 L of 20 µg/mL HA binding protein in 0.1 M $NaHCO_3$ solution and stored overnight at 4° C. The plate was then washed three times with 0.85% NaCl containing 0.05% Tween 20. To each well was then added 250 µL blocking solution (sodium phosphate buffer, 10 mmol, pH=7.4 containing 3% BSA and 0.9% NaCl, PBS+ 3% BSA) and the plate was incubated at RT for 2 h. The plate was then washed three times with 0.85% NaCl containing 0.05% Tween 20. To the plate was then added 50 µL of standard HA solutions and extracts from both experimental conditions, including various dilutions of these conditions. The plate was incubated at room temperature (about 20° C.) for 2 hours. The plate was then washed three times with 0.85% NaCl containing 0.05% Tween 20 and to each well was added 50 µL of biotinylated HA (1:2000 dilution) and then incubated for 2 hours at room temperature. The plate was then washed three times with 0.85% NaCl containing 0.05% Tween 20 and then added to each well was 50 µL of HRP-avidin D (1:3000 dilution). The plate was then incubated for 45 minutes at room temperature. The plate was then washed three times with 0.85% NaCl containing 0.05% Tween 20 and to each well was added 100 µL of orthophenylenediamine substrate solution. The plate was incubated at 37° C. for 10 minutes. The reaction was stopped by addition of 50 µL of 1M HCl. Finally, using a plate reader, the absorbance was read at 492 nm and recorded.

Absorbance measurements were averaged and converted to quantity measures. Circular cell-matrix constructs (75 mm diameter) formed in a serum containing media were determined to each contain about 200 µg hyaluronic acid while those formed in chemically defined medium each contained about 1.5 mg hyaluronic acid.

Example 14: Physical Testing and Mechanical Properties of the Cell-Matrix Construct Produced The mechanical properties of the tissue constructs of Example 1 (cell-matrix construct), Example 2 (cell-matrix construct with a keratinocyte layer thereon), and Example 3 (cell-matrix construct formed in defined medium) were quantified by membrane inflation tests. These tests are similar to assays used clinically (e.g. Dermaflex®, Cyberderm Inc., Media, Pa., and Cutameter®, Courage Khazaka, Cologne, Germany) but involve higher pressures including pressures able to burst the membrane. The sample cell-matrix construct was laid flat on a polycarbonate block centered over a cylindrical well 10 mm in diameter filled with normotonic saline. A metal plate with a circular hole corresponding to the diameter of the cylindrical well was placed over the sample and clamped to the block. The samples were then inflated by infusing additional saline into the well with a syringe pump. The resulting pressure was measured with a pressure transducer. Pressurization was carried out until device failure, the burst strength, which averaged at 439.02 mm Hg for the cell-matrix construct generated by the method of Example 1; 998.52 mm Hg for the samples of the cell-matrix construct with a keratinocyte layer generated by the method of Example 2; and, 1542.26 mm Hg for the samples cell-matrix construct formed in defined medium generated according to the method of Example 3.

To determine the thermal melting point of the dermal matrix, samples (cell-matrix construct), taken at 21 days were prepared using procedure described in Example 1. The samples denaturation temperature was determined by analysis with Mettler Toledo (Highston, N.J.) differential scanning calorimeter (DSC product #DSC12E). For our purposes, the melting temperature was determined by heating the sample from 45 and 80° C. at a rate of 1° C./minute. The average denaturation temperature for the samples is 60.8±1.2° C. (n=3).

The suture retention and pull strength of the epidermalized matrix created using the procedures in Examples 1 (cell-matrix construct) and 3 (cell-matrix construct formed in defined medium) were measured to determine the suturability of the construct in certain clinical situations. Suture retention strength of the 21 day old human dermal matrix was determined using method described in American National standards publication for Vascular Graft Prosthesis (Instruments, 1986) using a Mini-Bionex 858 test system (MTS systems Corporation, Minneapolis, Minn.)

For the samples of Example 1, (cell-matrix construct), the tensile strength was determined to be 365 N/m; for samples prepared according to Example 2 (cell-matrix construct with a keratinocyte layer), the tensile strength was 2720 N/m.

The suture retention strength for samples prepared according to Example 1 was 0.14 N; for those prepared according to Example 2, 0.22 N.

The constructs created as described in Examples 1, 2 and 3 have been made in both 24 mm and 75 mm diameters. The constructs made by the culturing techniques of all 3 methods are cohesive tissue-like structures are easily peeled form the membrane with minimal force, hence "peelable", and able to be physically handled and manipulated for use and testing without damage occurring.

Example 15: In Vitro Formation of a Collagenous Matrix by Human Neonatal Foreskin Fibroblasts in Chemically Defined Medium Human neonatal foreskin fibroblasts were expanded using the procedure described in Example 1. Cells were then resuspended to a concentration of $3 \times 10^6$ cells/ml, and seeded on to 0.4 micron pore size, 24 mm diameter tissue culture treated membrane inserts in a six-well tray at a density of $3.0 \times 10^6$ cells/TW ($6.6 \times 10^5$ cells/cm$^2$). Cells in this example were cultured in chemically defined medium throughout.

The medium contained: a base 3:1 mixture of DMEM, Hams F-12 medium (Quality Biologics, Gaithersburg, Md.), 4 mM GlutaMAX (Gibco BRL, Grand Island, N.Y.) and additives: 5 ng/ml human recombinant epidermal growth factor (Upstate Biotechnology, Lake Placid, N.Y.), $1 \times 10^{-4}$ M ethanolamine (Fluka, Ronkonkoma, N.Y. cat. #02400 ACS grade), $1 \times 10^{-4}$ M o-phosphoryl-ethanolamine (Sigma, St. Louis, Mo.), 5 µg/ml transferrin (Sigma, St. Louis, Mo.), 20 µM triiodothyronine (Sigma, St. Louis, Mo.), and 6.78 ng/ml selenium (Sigma Aldrich Fine Chemicals Company, Milwaukee, Wis.), 50 ng/ml L-ascorbic acid (WAKO Chemicals USA, Inc.), 0.2 µg/ml L-proline (Sigma, St. Louis, Mo.), 0.1 µg/ml glycine (Sigma, St. Louis, Mo.).

To the basic medium above, other components were added in these separate Conditions:
1. 5 µg/ml insulin (Sigma, St. Louis, Mo.), 0.4 µg/ml hydrocortisone (Sigma, St. Louis, Mo.), 0.05% polyethylene glycol (PEG) (Sigma, St. Louis, Mo.).
2. 5 µg/ml insulin (Sigma, St. Louis, Mo.), 0.4 µg/ml hydrocortisone (Sigma, St. Louis, Mo.).
3. 375 µg/ml insulin (Sigma, St. Louis, Mo.), 6 µg/ml hydrocortisone (Sigma, St. Louis, Mo.).

Figure 2:
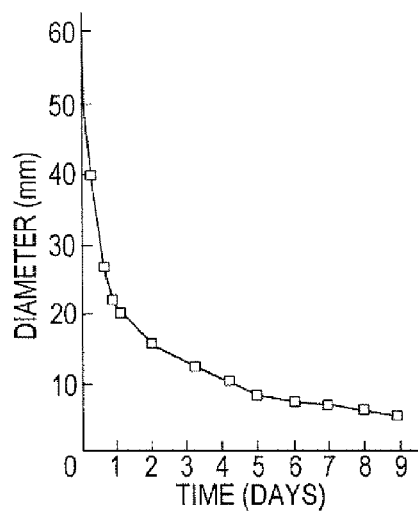
FIG. 2 is a plot of data illustrating the contraction with fibroblast cells of a hydrated collagen lattice.

Samples were formalin fixed and processed for hemotoxylin and eosin staining for light microscope analysis. Visual histological evaluation demonstrated that the Condition 2 lacking PEG demonstrated a comparably similar matrix as Condition 1 containing PEG. Biochemical analysis measuring the collagen content of the construct showed nearly the same amount of collagen in both: 168.7±7.98 µg/cm$^2$ for Condition 1 with PEG as compared to 170.88±9.07 µg/cm$^2$ for Condition 2 without PEG. Condition 3 containing high levels of insulin and hydrocortisone showed a higher expression of matrix, including collagen, at a timepoint earlier than the other two conditions. Besides endogenously produced fibrillar collagen, decorin and glycosaminoglycan were also present in the cell-matrix constructs in all Conditions. The cultured dermal construct formed by the method of Condition 2 of this Example is shown in FIG. 2. Shown in FIG. 2 is a photomicrograph of a fixed, paraffin embedded, hematoxylin and eosin stained section of a cell-matrix construct formed from cultured human dermal fibroblasts in chemically defined medium at 21 days. The porous membrane appears as a thin translucent band below the construct and it can be seen that the cells grow on the surface of the membrane and do not envelope in integrate the membrane with matrix.

Figure 3:
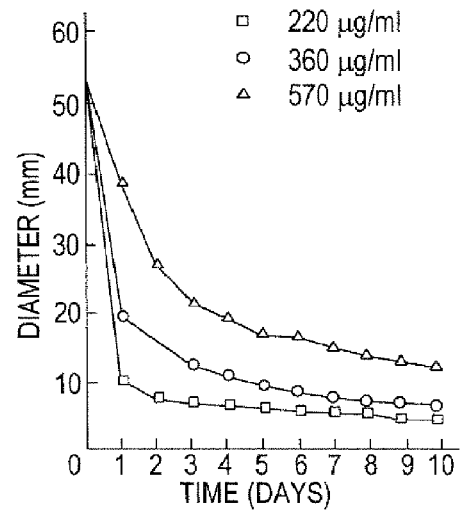
FIG. 3 is a plot of data illustrating the contraction with fibroblast cells of hydrated collagen lattices having different collagen contents.

FIG. 3 shows transmission electron microscope (TEM) images of two magnifications of cultured dermal construct formed by the method of Condition 2 of this Example at 21 days. FIG. 3A is a 7600× magnification showing alignment of endogenous collagen fibers between the fibroblasts. FIG. 3B is a 19000× magnification of fully formed endogenous collagen fibers demonstrating fibril arrangement and packing.

In all Conditions of this Example, the cultured dermal constructs formed comprise dermal fibroblasts and endogenously produced matrix. All have fully formed collagen fibrils in packed organization arranged between the cells. Their fibrous qualities, thickness, and cohesive integrity give the construct considerable strength to allow it to be peelably removed from the culture membrane and handled as it is transferred to a patient to be treated with the construct, as in a graft or implant.

Example 16: Full Thickness Skin Construct

Using a 21 day dermal construct formed by human dermal fibroblasts under chemically defined conditions according to the method of Condition 2 (without PEG) described in Example 15, above, normal human neonatal foreskin epidermal keratinocytes were seeded on the top surface of the cell-matrix construct to form the epidermal layer of the skin construct.

The medium was aseptically removed from the culture insert and its surrounds. Normal human epidermal keratinocytes were scaled up to passage 4 from frozen subculture cell stock to confluence. Cells were then released from the culture dishes using trypsin-versene, pooled, centrifuged to form a cell pellet, resuspended in epidermalization medium, counted and seeded on top of the membrane at a density of $4.5 \times 10^4$ cells/cm$^2$. The constructs were then incubated for 90 minutes at 37±1° C., 10% $CO_2$ to allow the keratinocytes to attach. After the incubation, the constructs were submerged in epidermalization medium. The epidermalization medium is composed of: a 3:1 base mixture of Dulbecco's Modified Eagle's Medium (DMEM) (containing no glucose and no calcium, BioWhittaker, Walkersville, Md.) and Hams F-12 medium (Quality Biologics Gaithersburg, Md.), supplemented with 0.4 µg/ml hydrocortisone (Sigma St. Louis, Mo.), $1 \times 10^{-4}$ M ethanolamine (Fluka, Ronkonkoma, N.Y.), $1 \times 10^{-4}$ M o-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), 6.78 ng/ml selenium (Aldrich), 24.4 µg/ml adenine (Sigma Aldrich Fine Chemicals Company, Milwaukee, Wis.), 4 mM L-glutamine (BioWhittaker, Walkersville, Md.), 50 µg/ml L-ascorbate sodium salt (Sigma Aldrich Fine Chemicals Company, Milwaukee, Wis.), 16 µM linoleic acid (Sigma, St. Louis, Mo.), 1 µM tocopherol Acetate (Sigma, St. Louis, Mo.) and 50 µg/ml gentamicin sulfate (Amersham, Arlington Heights, Ill.). The constructs were cultured in the epidermalization medium for 2 days at 37±1° C., 10±1% $CO_2$.

After 2 days the medium was exchanged with fresh medium composed as above, and returned to the incubator set at 37±1° C., 10±1% $CO_2$ for 2 days. After the 2 days, the carrier containing the construct was aseptically transferred to new culturing trays with sufficient media to achieve a fluid level just to the surface of the carrier membrane to maintain the developing construct at the air-liquid interface. The air contacting the top surface of the forming epidermal layer allows stratification of the epithelial layer. The constructs were incubated at 37±1° C., 10% $CO_2$, and low humidity, in media with media changes every 2-3 days for 7 days. This medium contained a 1:1 mixture of Dulbecco's modified Eagle's medium (DMEM) (containing no glucose and no calcium, BioWhittaker, Walkersville, Md.), Hams F-12 medium (Quality Biologics, Gaithersburg, Md.), supplemented with 0.4 µg/ml hydrocortisone (Sigma, St. Louis, Mo.), $5\times10^{-4}$ M ethanolamine (Fluka, Ronkonkoma, N.Y.), $5\times10^{-4}$ M o-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), 6.78 ng/ml selenium (Sigma Aldrich Fine Chemicals Company), 24.4 µg/ml adenine (Sigma Aldrich Fine Chemicals Company), 4 mM L-glutamine (BioWhittaker, Walkersville, Md.), 2.65 µg/ml calcium chloride (Mallinckrodt, Chesterfield, Mo.), 16 µM linoleic acid (Sigma, St. Louis, Mo.), 1 µM tocopherol acetate (Sigma, St. Louis, Mo.), 1.25 mM serine (Sigma, St. Louis, Mo.), 0.64 mM choline chloride (Sigma, St. Louis, Mo.) and 50 µg/ml gentamicin sulfate (Amersham, Arlington Heights, Ill.). The cultures were fed every 2-3 days, for 14 days.

Figure 4:
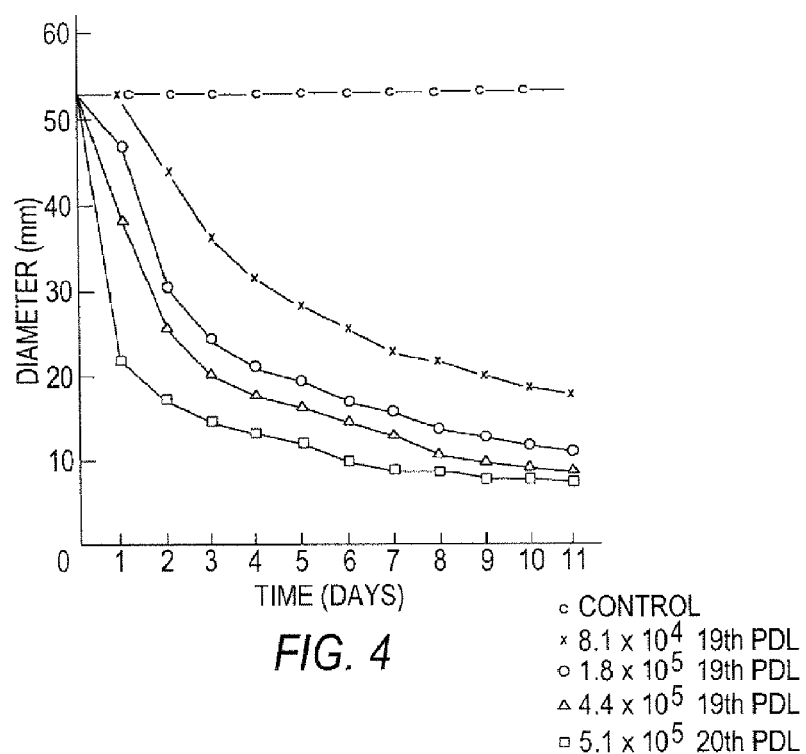
FIG. 4 is a plot of data illustrating the contraction with fibroblast cells of hydrated collagen lattices containing different numbers of fibroblast cells.

Samples, in triplicate, were submitted 10, 12, and 14 days after the construct was lifted to the air-liquid interface for hematoxylin and eosin processing as described in Example 1 to determine gross appearance under light microscopy. The resulting construct was a bilayer skin construct consisted of a lower dermal layer consisting of dermal fibroblasts surrounded by matrix overlaid by an upper epidermal layer of stratified and differentiated keratinocytes. The bilayer skin construct of this Example is shown in FIG. 4. FIG. 4 is a photomicrograph of a fixed, paraffin embedded, hematoxylin and eosin stained section of a cultured skin construct formed in chemically defined media in the absence of exogenous matrix components comprising a cell-matrix construct formed from cultured human dermal fibroblasts in chemically defined medium with a multilayered, differentiated epidermis formed from cultured human keratinocytes in chemically defined medium.

Example 17: Formation of a Collagenous Matrix by Human Buccal Fibroblasts

The purpose of this experiment is to produce a cell-matrix construct from buccal fibroblasts isolated from human cheek tissue. Buccal were cultured in T-150 flasks in DMEM containing 10% NBCS medium. After 7 days, to expand the number of cells further, buccal cells were harvested and passaged into nine T-150 flasks at $4.0\times10^6$ cells in DMEM containing 10% NBCS medium and cultured until confluence at which time the cells were harvested.

To harvest the cells, the medium was aspirated from the culture flask. To rinse the monolayer, sterile-filtered phosphate buffered saline was added to the bottom of each culture flask and then aspirated from the flasks. Cells were released from the flask by adding 5 mL trypsin-versene glutamine (BioWhittaker, Walkersville, Md.) to each flask and gently rocking to ensure complete coverage of the monolayer. Cultures were returned to the incubator. As soon as the cells were released 5 ml of SBTI (Soybean Trypsin Inhibitor) was added to each flask and mixed with the suspension to stop the action of the trypsin-versene. The cell suspension was removed from the flasks and evenly divided between sterile, conical centrifuge tubes. Cells were collected by centrifugation at approximately 800-1000×g for 5 minutes.

Cells were resuspended using fresh medium to a concentration of $3.0\times10^6$ cells/ml, and seeded onto 0.4 micron pore size, 24 mm diameter tissue culture treated inserts (TRANSWELL®, Corning Costar) in a six-well tray at a density of $3.0\times10^6$ cells/insert ($6.6\times10^5$ cells/cm$^2$). The cells were maintained in an incubator at 37±1° C. with an atmosphere of 10±1% $CO_2$ and fed medium containing: a base 3:1 mixture of DMEM, Hams F-12 medium (Quality Biologics, Gaithersburg, Md.), 4 mM GlutaMAX (Gibco BRL, Grand Island, N.Y.) and additives: 5 ng/ml human recombinant epidermal growth factor (Upstate Biotechnology, Lake Placid, N.Y.), 0.4 µg/ml hydrocortisone (Sigma, St. Louis, Mo.), $1\times10^{-4}$ M ethanolamine (Fluka, Ronkonkoma, N.Y. cat. #02400 ACS grade), $1\times10^{-4}$ M O-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 µM triiodothyronine (Sigma, St. Louis, Mo.), and 6.78 ng/ml selenium (Sigma Aldrich Fine Chemicals Company, Milwaukee, Wis.), 50 ng/ml L-ascorbic acid (WAKO Chemicals USA, Inc.), 0.2 µg/ml L-proline (Sigma, St. Louis, Mo.), 0.1 µg/ml glycine (Sigma, St. Louis, Mo.) and 0.05% poly-ethylene glycol (PEG) (Sigma, St. Louis, Mo.).

At day 1 post seeding, medium was replaced with Serum Free Production Media, exchanged every 2-3 days for 21 days. At day 21, samples were fixed in formalin for histology. Three samples were used for protein and collagen production analysis.

Collagen production for 24 mm diameter constructs averaged 519 µg per construct after 21 days in culture. Total protein production for 24 mm diameter constructs averaged 210 µg per construct after 21 days in culture. Morphologically, the buccal fibroblast cell-matrix construct, a cultured tissue construct of oral connective tissue, showed buccal fibroblasts surrounded by matrix while physically, the construct had physical bulk and integrity.

Example 18: Preparation of Tissue-Equivalent by Contracting Collagen Lattices Seeded with Fibroblast Cells Crude collagen solutions were prepared as follows. Frozen rat tails from 450 gm rats were thawed in 70% EtOH for 20 minutes. The tendon bundles were excised in 70% EtOH in a laminar flow hood. Individual tendons were pulled out of the tendon sheath, minced and placed in dilute acetic acid (1:1,000) using 250 ml per tail. This solution was left standing for 48 hours at 4° C. at which point the minced tendons had swelled to occupy the total volume. This viscous solution was centrifuged at 23 k rpm in a Beckman L ultracentrifuge in an SW25 rotor for 1 hour. The supernatant was drawn off and stored at 40. C. as crude collagen solution (Protein "C").

Refined collagen solution was prepared by mixing crude collagen solution with 0.1 M NaOH in a 6:1 ratio to neutralize the acetic acid, upon which collagen precipitated. This solution was centrifuged at 1500 rpm for 5 minutes in a clinical centrifuge. The supernatant was discarded and an equal volume of fresh acetic acid (1:1,000) was introduced to resolubilize the collagen. This solution was stored at 4° C. as refined collagen solution (Protein "R").

Protein concentration was determined by the method of Lowry et al. See Lowry, 0. H., Rosebrough, N. J., Farr, N. J. and Randall, R. J., J. Biol. Chem., 193, 265-275 (1951) and Waddel, W. J., J. Lab and Clin. Med. 48, 311-314 (1956).

Protein lattices were prepared in 60 mm Falcon bacteriological dishes to which fibroblasts adhere poorly. Each dish contained: 1.0 ml 5× McCoy's 5a medium, 1.0 ml Fetal Calf Serum, 0.25 ml 0.1 M NaOH, 1.5 ml collagen solution, and 1.0 ml fibroblasts suspended in 1× McCoy's medium. The dishes were first filled with the above volume of McCoy's medium, serum and NaOH and then set aside until the fibroblast suspension was prepared. Speed was important in simultaneous addition of collagen solution and fibroblasts since the gel started setting immediately. Dishes were placed in an incubator at 37° C. in a 5% $CO_2$ atmosphere at 100% humidity. Gels incorporating the fibroblasts were completely set after 10 minutes.

The fibroblasts employed were human foreskin fibroblasts, strain 1519, obtained from the Human Genetic Cell Repository at the Institute for Medical Research in Camden, N.J. These cells were grown and maintained in McCoy's 5a modified medium with 20% serum, penicillin, and streptomycin. The cultures were free of mycoplasma. The M.I.T. Cell Culture Center prepared and froze cells of every tenth population doubling level (PDL).

To measure lattice diameters, the dishes were placed on top of a transparent metric ruler on a dark background. Optimum visibility of gel edges was obtained by shining white light horizontally against the edge of the dish. Contracted gels were well formed discs; they showed very slight differences of diameter at various points. The average of the major and minor axes was taken as the diameter.

Example 19: Measurement of Contraction of Hydrated Collagen Lattice By Fibroblast Cells The contraction of a hydrated collagen lattice prepared according to the procedures of Example 18 and containing 570 .mu.g/ml of Protein "C" by $7.5 \times 10^6$ human foreskin fibroblasts, strain 1519, 19th PDL, was determined. Medium was changed in the dish on the first, fourth and eighth days. The data obtained are plotted in FIG. 3 which indicates a 112-fold reduction of lattice area in a little over seven days. Within one day, there had been a seven-fold area contraction.

Example 20: Contraction of Hydrated Collagen Lattices of Different Protein Concentration The effect of protein concentration in hydrated collagen lattices on contraction of the lattice was determined as follows. Three hydrated collagen lattices were prepared according to the procedures of Example 18 except that each contained a different concentration of Protein "R". Human foreskin fibroblasts, strain 1519, 19th PDL were employed and medium was changed on the fourth day.

The data obtained are plotted in FIG. 4 where it can be seen that the rate of lattice contraction varied inversely with gel protein concentration. The lattice areas diminished as time went on.

Example 21: Effect of Number of Cells on Contraction of Hydrated Collagen Lattices The effect of the number of cells on contraction of hydrated collagen lattices was determined as follows. A number of hydrated collagen lattices containing 720 .mu.g/ml of Protein "R" were prepared according to the procedure of Example 18. Human foreskin fibroblasts, strain 1519, were employed and the medium in each of the cultures was changed in the third, seventh and tenth days.

Controls were employed to which no cells were added. In addition, four series of experiments were run in which varying numbers of cells were added. The data obtained are plotted in FIG. 5 in which each point represents the average of the contraction of three or four lattices. Deviations are not shown because they were all very small (<.+−.1.0 mm).

As can be seen, the number of cells did have an effect on the rate of lattice contraction but this difference in contraction became less significant as a function of time. Lattice diameters approached a common small number for concentrations above some minimum value. Below the minimum value, the relationship between rate of lattice contraction and cell number was distinctly non-linear. The lattices with $8.1 \times 10^4$ cells did not begin to contract for 24 hours. These sparsely populated lattices lagged well behind the more densely populated ones throughout the period of the experiments.

Example 22: Contractile Capacity in Hydrated Collagen Lattices of Cells of Different PDL The contractile capacity in hydrated collagen lattices of cells of different population doubling level (PDL), that is cells which had undergone different numbers of cell divisions, was determined as follows. Cultures were formed of hydrated collagen lattices prepared according to the procedures of Example 18 and containing 720 .mu.g/ml Protein "R". Medium was changed on the third, seventh and tenth days.

Control cultures contained no cells. In addition, a series of experiments with cells of different PDLs was carried out.

Figure 5:
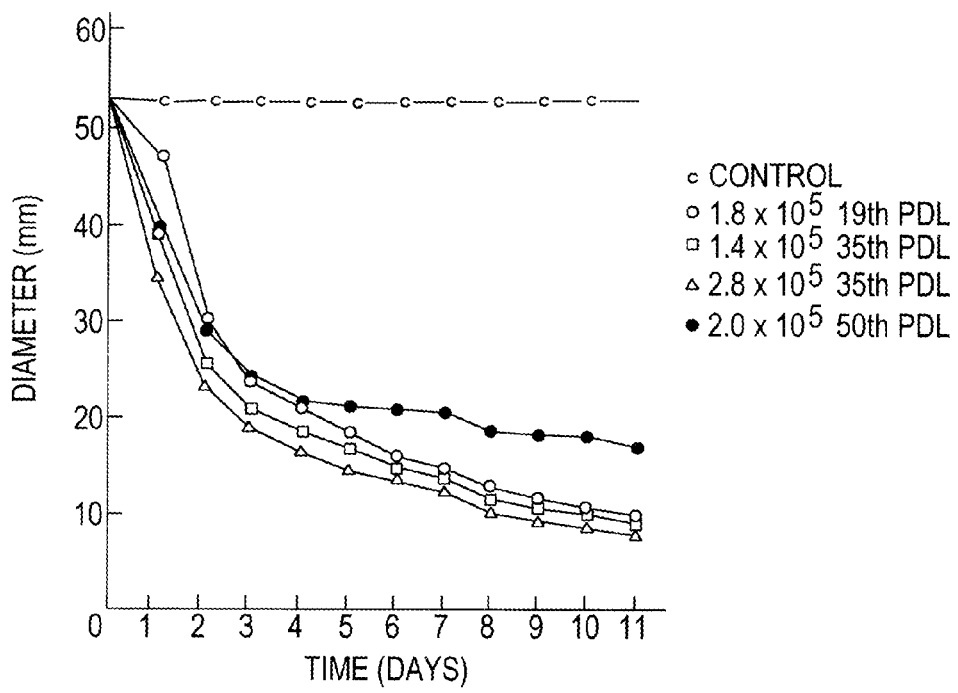
FIG. 5 is a plot of data indicating the contractile capacity of fibroblast cells on hydrated collagen lattices employing cells of different population doubling levels.

The data collected are plotted in FIG. 5 in which each point represents the average of three or four lattice contractions. Deviations were <.+−.1.0 mm. As can be seen, cells of the 35th PDL performed as well as those of the 19th PDL, but cells of the 50th PDL were unable to contract lattices at a commensurate rate.

Example 23: Effect of Cytochalasin B on Capacity of Cells to Contract a Hydrated Collagen Lattice The effect of the inhibitor cytochalasin B on the capacity of cells to contract a hydrated collagen lattice was determined as follows. Hydrated collagen lattices were prepared according to Example 18 which contained a Protein "C" content of 570 .mu.g/ml. Fibroblast (human foreskin, strain 1519, 19th PDL) cell concentration in the cultures was $5.0 \times 10^5$. 10.0 .mu.g/ml cytochalasin B was added to each culture and medium was changed on the fourth and eighth days.

Data obtained are plotted in FIG. 6, and as can be seen, this concentration of cytochalasin B completely blocked lattice contraction even at the relatively high cell concentration employed.

Example 24: Effect of Colcemid on Collagen Lattice Concentration

Figure 7:
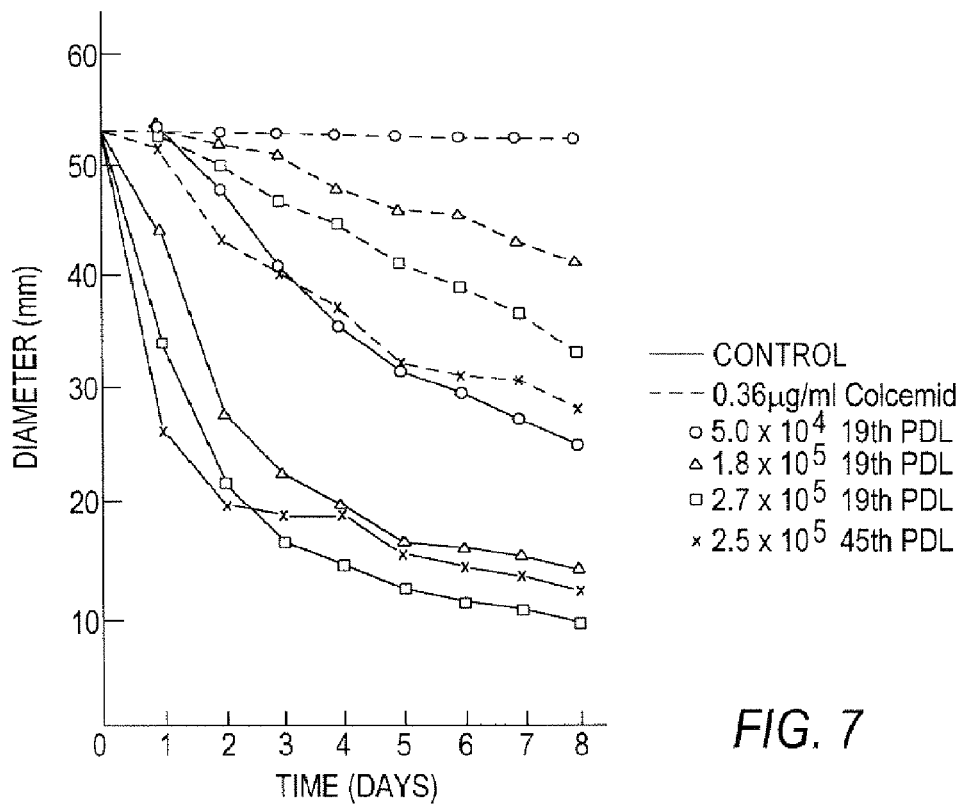
FIG. 7 is a plot of data illustrating the effect of 0.36 .mu.g/ml of the inhibitor colcemid on the capacity of fibroblast cells to contract a hydrated collagen lattice.

The effect of the inhibitor colcemid on protein lattice contraction was determined as follows. Cultures containing hydrated collagen lattices prepared according to the procedures of Example 18 which contained 570 .mu.g/ml of Protein "C" 0.36 .mu.g/ml colcemid was added to each of these except for the controls which contained no colcemid. The same number of cells was added to both test cultures and control cultures, and data obtained are plotted in FIG. 7. As can be seen, the 45th PDL cells outstripped the performance of 19th PDL cells, while 45th PDL untreated cells lagged behind the 19th PDL untreated cells. It is clear that colcemid can be used to regulate the rate and extent of contraction of the lattices.

Figure 8:
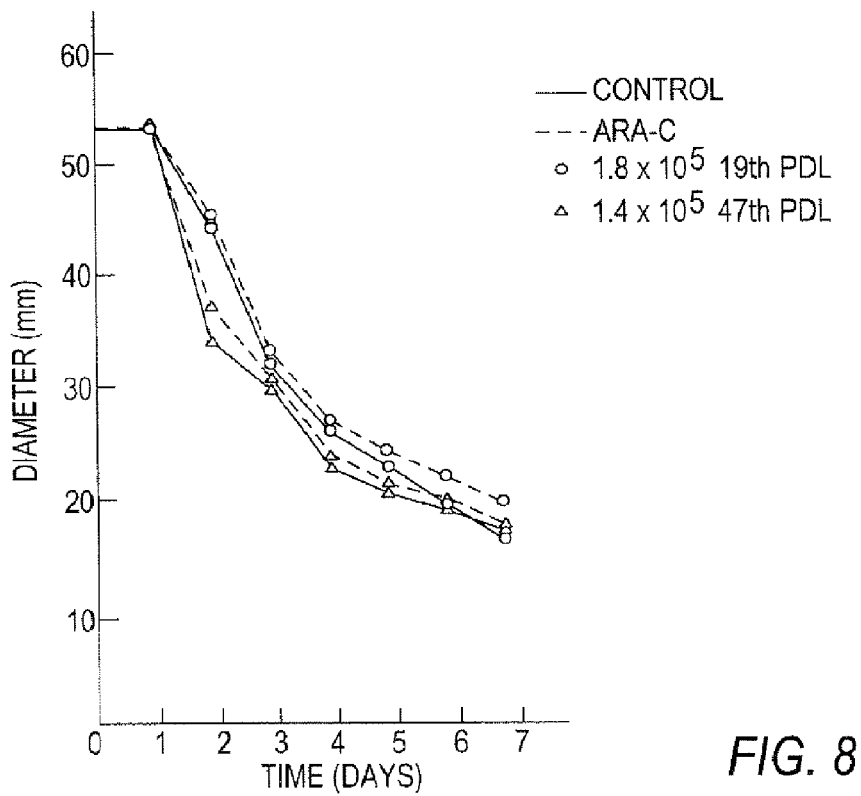
FIG. 8 is a plot of data illustrating the effect of cytosine arabinoside on the capacity of fibroblast cells to contract a hydrated collagen lattice.

Example 25: Effect of Cytosine Arabinoside on Collagen Lattice Contraction by Cells of Different PDL The effect of 1.0 .mu.g/ml of cytosine arabinoside on protein lattice contraction by cells of different PDL level was tested as follows. Cultures containing hydrated collagen lattices containing Protein "C" in a concentration 570 .mu.g/ml were prepared. Human foreskin fibroblasts, strain 1519, of the 19th PDL or 47th PDL were added to both controls containing no cytosine arabinoside and test cultures containing cytosine arabinoside. Data obtained are plotted in FIG. 8, where it can be seen that the 47th PDL cells outperformed the lower PDL cells even though they were fewer in number. In these experiments cytosine arabinoside was used to block DNA synthesis and thereby keep the number of cells in the lattice constant.

Example 26: Formation of Skin-Equivalent Employing Human Foreskin Fibroblasts and Keratinocytes A hydrated collagen lattice was prepared according to the procedures of Example 18 which contained 500 .mu.g/ml of Protein "C". Human foreskin fibroblasts obtained in a biopsy were removed from a culture plate with a solution of EDTA and trypsin. The suspension of single cells was centrifuged to pellet the cells, after which the cells were resuspended in culture medium and then deposited on top of the hydrated collagen matrix seven days after the fibroblast cells had been introduced. Within three days, the keratinocyte cells had attached to the lattice substrate and the process of keratinization began leading to the formation of an impervious cornium. Histological observations were made by means of electron microscopy.

Example 27: In Vivo Studies with Skin-Equivalent Employing Guinea Pig Skin Fibroblasts and Keratinocytes Skin biopsies were taken from guinea pigs and dermis was separated from epidermis surgically. Dermis was dissociated enzymatically into constituent cells which were plated onto tissue culture dishes and allowed to undergo proliferation. Cells from each experimental animal were grown in separate dishes so that their identity was preserved. Tissues were made up in vitro by forming contracted-hydrated collagen lattices according to the procedures of Example 18 except employing fibroblasts from the guinea pigs. Some of the lattices, after contraction, were plated according to Example 26 with epidermal cells or keratinocytes taken from second biopsies so that keratinocytes as well as fibroblasts in each graft were from the animal which was to become the recipient of the graft.

Grafts of these skin-equivalents were made to the dorsum of the experimental animals (guinea pigs), and it was found that such grafts were thoroughly integrated at all levels within one week. From below, they had become vascularized; at the level of the dermis, collagen fibrils of the graft were interwoven with those of the surrounding host tissue. In histological sections, the grafts could be distinguished by their high fibroblast cell density and by the reduced degree of birefringence as compared with that of surrounding skin when viewed through a polarization microscope. Even those grafts hot provided with epidermis were completely covered with an epidermal cell layer (keratinocytes) many cells deep. The layer was continuous with that of the adjacent host skin. It was clear also that dermal wound contraction was inhibited by the presence of the skin-equivalent graft just as it is when an autograft is made.

Example 28: In Vivo Studies with Skin-Equivalent Employing Rat Skin Fibroblasts, Dermal and Epidermal Cells Formation of Dermal-Equivalent A small biopsy from a potential graft recipient was cut into 1.0 mm.sup.2 fragments. Fibroblasts grew out of the fragments and populated the Lux tissue culture dish, and after 4-7 days, the fragments were removed and discarded or transferred to new plates. The cells on one or more plates were allowed to propagate until they became nearly confluent, at which time the cells were removed by treatment with trypsin, washed, and thereafter propagated in tissue-culture flasks. About 5.times.10.sup.4 cells were needed for each square centimeter of dermal equivalent, and an appropriate number of cells was cast by removing them from the substrate with trypsin after which they were suspended and combined with a collagen solution, rat serum, and tissue-culture medium. Collagen was obtained by extracting rat tail tendons in 0.02 M acetic acid and purifying by centrifugation. When kept at an acid pH and a protein concentration of 1.5 mg/ml, the collagen was a viscous slightly opalescent solution. It consisted only of collagen type I with no contaminating proteins detectable by SDS polyacrylamide gel electrophoresis. At the moment the collagen was combined with the cells and other ingredients, the pH was adjusted to 7.2 with NaOH, which caused the collagen to come out of the solution in the form of fibrils. As this occurred, a gel or lattice in which fluid was trapped formed. The cells in the lattice were more or less uniformly distributed through it. By a process of active compaction of collagen fibrils by the cells, the lattice was transformed into a tissue of firm consistency. The result was loss of trapped fluid and a many-fold decrease in volume of the original lattice. A tissue resulted which constituted a dermal-equivalent (DE).

Addition of Epidermis

Epidermal cells dissociated from the biopsy fragments by means of trypsin were distributed as a suspension on the dermal equivalent. In 2-4 days, the epidermal cells formed a continuous sheet that covered the dermal substratum. Within this time, the confluent sheet of cells began to differentiate. Desmosomal junctions, tonofilaments, and keratohyalin granules were apparent, and the process of keratinization proceeded leading to formation of an impervious stratum corneum. The entire process would occur in vitro on the DE if permitted. However, in this work, the living, two-layered tissue was considered ready for grafting as soon as the epidermal cells formed a confluent sheet which served as a skin-equivalent (SE).

Skin-equivalents were grafted to a large number of rats with the following results. First, by 3-5 days after implantation, vascularization of the graft had begun and continued rapidly with no necrosis or ischemia occurring. Second, with few exceptions, the graft inhibited would contraction. When the graft was made, the periphery of normal skin adjacent to the graft was tattooed to mark the limits of the grafts, a procedure which enabled the monitoring with time of the dimensions of the graft. The exceptions to inhibition of wound contraction may have been due to inadequate initial coverage of the dermal equivalent by the epidermis, to dislodgement of the graft by the animal, or to formation of an inadequate lattice which was a function of the quality of the collen preparation used.

In one study of thirty-one such grafts examined at the time the bandage was removed (9-14 days), seven inhibited wound contract completely, fifteen blocked would contraction by 75% or more, and twenty-three blocked it by 50% or more.

In another study of fifty-two grafts, wound contraction was blocked in at least 75-80% of the grafts.

Although a number of grafts showed a decrease in size with time, most were stabilized by sixty days and none were rejected. Grafts of large size (approximately 8.times.12 cm) with good epidermal coverings, effectively blocked wound contraction (75% or more) and took well as replacements for burned skin.

Grafts persisted for long periods, the longest having been in place for over two years.

In addition to becoming well vascularized, the matrix of the dermal equivalent underwent considerable remodeling during the first few months after grafting. Changes in its structure were studied by examining the birefringence of histologic section from which it was apparent that the matrix exhibited birefringence by one week after grafting, a phenomenon not observed in granulation tissue of comparable age. Whereas the birefringence increased in intensity with time, the pattern, generally, was not one of the basket-weave configuration characteristic of normal dermis. However, by ten weeks in the transition region where the graft meets normal tissue, the basketweave pattern had begun to develop.

In vivo, the epidermis hypertrophies, and even ten weeks after grafting, was considerably thicker than adjacent normal tissue. Tongues or pegs or epidermis were seen penetrating the dermal equivalent. Externally, for a period of several months, the epidermis appeared somewhat scaley, and the graft had a reddish tint. By about three months, grafts were smooth and pinkish in color resembling normal skin of the albino rat but lacking hair. A degree of scaliness persisted even to seven months which might be attributed to the absence of sebaceous glands.

Example 29: Preparation of Tissue-Equivalent by Contraction of Collagen Lattice with Platelets Outdated platelet concentrates were obtained from the Red Cross Blood Center in Boston, Mass. Rat and pig tail tendon collagens were extracted as described in Example 18; pigskin collagen was supplied by Dr. Paul Ehrlich of the Shriners' Burns Institute of Boston; and telogen, a bovine collagen, was obtained from Collagen Corporation, Palo Alto, Calif. Collagen concentrations were determined using a modification of the method of Waddel. See Waddel, W. J., J. Lab and Clin. Med. 48, 311-14 (1956). The formula employed was: $\mu g/ml = O.D.\ 215 - O.D.\ 225/64.6$.

The platelet concentrate, concentrated to 60× as obtained from the Red Cross, was further concentrated by centrifugation for 50 minutes at 500 rpm in an IEC PR-2 centrifuge using a 253 rotor at 4° C. to remove red blood cells. The supernatant was then centrifuged an additional 50 minutes at 1500 rpm using the same rotor to concentrate the platelets. Supernatant was drawn off and used to resuspend the platelet pellets obtained. The absolute platelet concentration varied from one experiment to the next depending upon the platelet concentrations in the blood of the donors, but all concentration values within each experiment are based on the use of one or pooled samples which are concentrated and then diluted. A 1× platelet concentration is equivalent to the concentration of platelets in 1.0 ml of blood.

Platelet lattices were cast by combining, in order, the following: 2.3 ml DMEM 1.76× medium, (Flow Laboratories), 1.5 ml rat tail tendon collagen, 0.25 ml 0.1 N NaOH (the concentration of NaOH needed to neutralize the collagen varied slightly depending upon the acidity of the collagen preparations used), and 0.45 ml FBS (Flow Laboratories). This mixture was poured into a 60 mm Falcon 0007 Petri dish with 0.5 ml of a 5× platelet concentrate applied in small drops on the dish surface. Alternately, all ingredients were combined in a separate vessel and poured into the empty Petri dish. The resulting lattices were incubated at 37° C. in a 90% air/10% $CO_2$ atmosphere of 100% humidity. Lattice thickness was controlled by increasing or decreasing the total lattice volume cast. No differences were observed in rates of lattice contraction as a function of casting procedure.

The rates of contraction were determined by drawing the fluid released by the lattice into a 1 ml pipette at first, and larger ones later, and then recording the volume of withdrawn fluid after which the withdrawn fluid was returned to the dish. These measurements were repeated hourly until the lattice had contracted maximally. In those lattices having a platelet concentration of 1× or lower, the lattice edges were first detached from the dish using a fine scalpel to free fluid trapped beneath the lattice for measurement. Because a lattice will release additional fluid when torn, care was taken to avoid damaging the lattice to obtain measurements of fluid released only by platelet contraction. Experiments were also conducted to determine the effect of the addition of thrombin (Sigma Chemicals) by spotting thrombin and platelet concentrate onto the Petri dish in discrete droplets prior to the addition of the combined DMEM collagen, NaOH and FBS.

Figure 9:
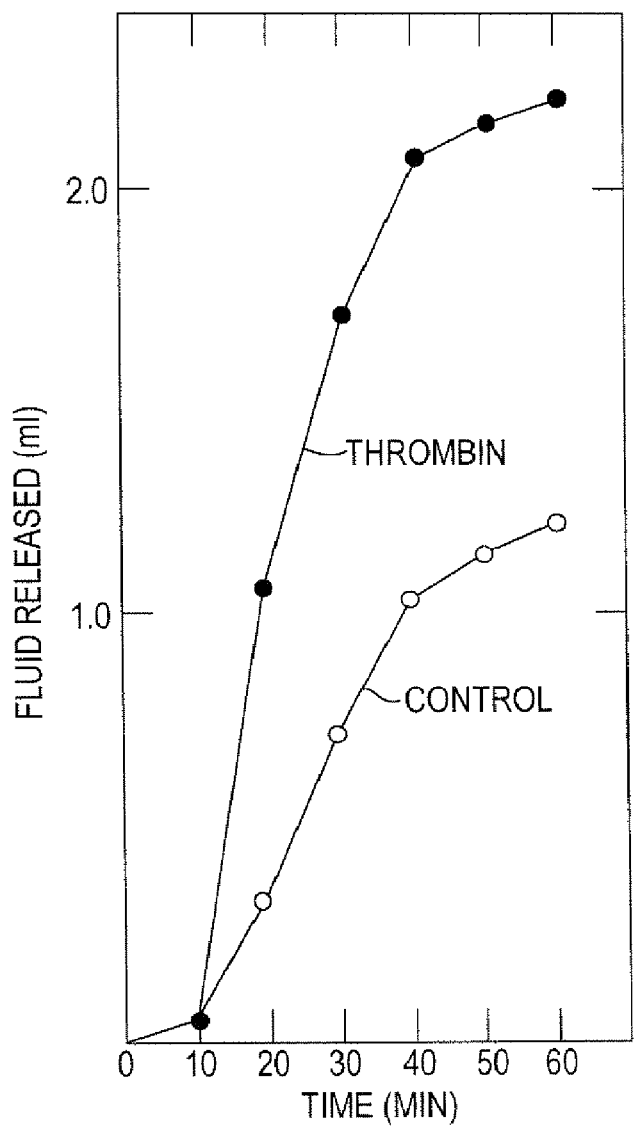
FIG. 9 is a plot illustrating the effect of thrombin on the contraction by platelets of collagen lattices at a thrombin concentration of 4.0 units/ml.

FIG. 9 is a plot of data obtained which illustrate the effect of thrombin on the contraction by platelets of collagen lattices when the thrombin concentration was 4.0 units/ml.

Figure 10:
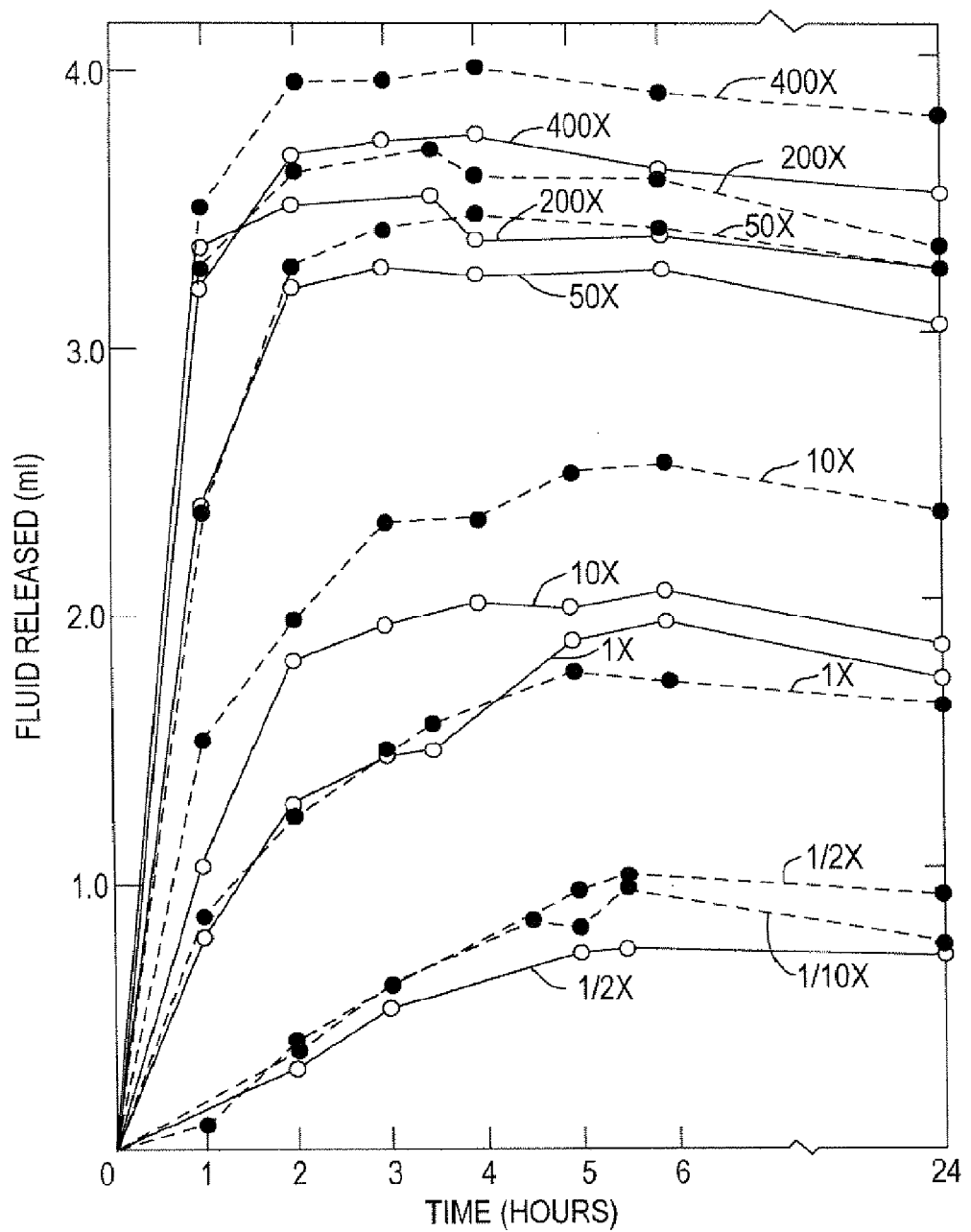
FIG. 10 is a plot illustrating collagen lattice contraction as a function of a platelet concentration and the presence of thrombin at a concentration of 4.0 units/ml.
Figure 11A:
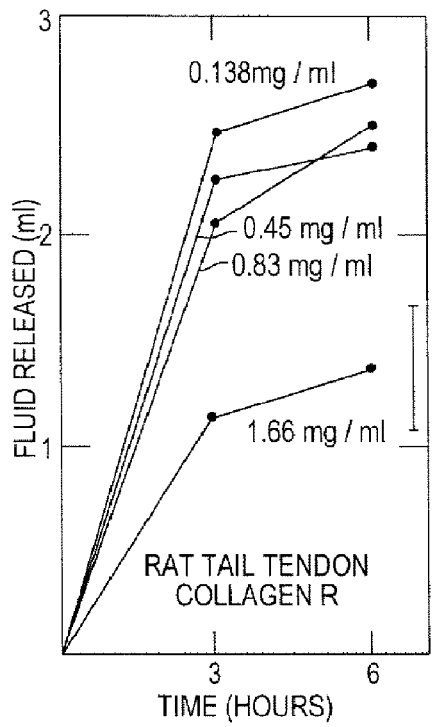
FIGS. 11A-11D are plots illustrating lattice contraction of collagen lattices as a function of the type and concentration of collagen employed; and, FIG. 12 is a plot illustrating the effects of the inhibitors cytochalasin B and colcemid on the contraction of hydrated collagen lattices by platelets.
Figure 11B:
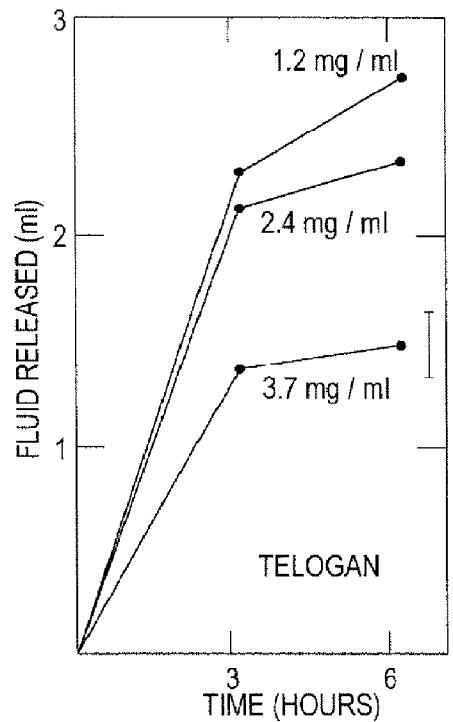
Figure 11C:
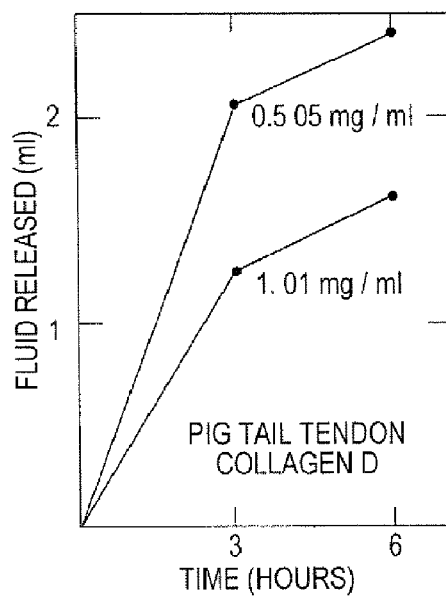
Figure 11D:
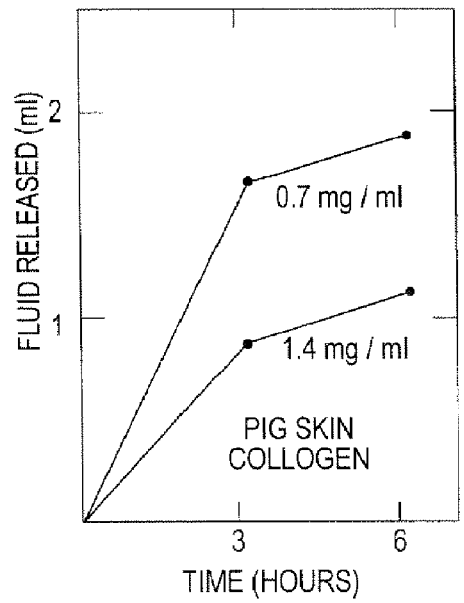

FIG. 10 is a plot illustrating the lattice contraction obtained as a function of platelet concentration and the presence of thrombin at a concentration of 4.0 units/ml.

As can be seen, the reaction is quite rapid. At a platelet concentration of 1×, 80-90% of the total fluid which will be expressed has taken place by the third hour after casting of the lattice. By six hours, the reaction is essentially complete and equilibrium is attained; that is, no further fluid release is observed under conditions of 100% humidity. At this point, 20-80% of the initial fluid volume has been expressed from the lattice, with the precise amount depending upon platelet and collagen concentrations and on other casting medium variables. The process of platelet lattice contraction results in the formation of a tissue-equivalent of relatively high tensile strength compared with that of a collagen lattice cast without platelets.

When thrombin is included in the casting mixture with a sufficient number of platelets, the tissue equivalent forms more quickly as indicated by FIG. 2. The tissue-equivalent containing thrombin has properties somewhat different from those cast without it, its tensile strength being somewhat less and its fluid content lower. Tensile strength was measured by tying gram weights to tissue equivalents after casting and measuring breaking time.

The rate of contraction of platelet lattices is related to the concentration of platelets. Increasing the platelet concentration speeds up the rate of lattice contraction and results in a lattice with proportionately less fluid, as can be seen in FIG. 10.

Example 30: Effect of Protein Concentration and Type on Contraction by Platelets The effect of protein concentration and source on contraction of lattices by platelets was determined by employing collagen from different sources in different concentrations, but otherwise following the procedures of Example 29. The resulting data are plotted in FIGS. 11A-11D.

As can be seen, increasing the collagen content of the casting medium reduces the rate of contraction and quantity of fluid expressed. These results correspond generally to those obtained when fibroblasts were used as the contractile agent.

Collagen from the four different sources employed functioned similarly, except that telogen offered considerably less resistance to contraction than collagen from the other three sources.

Example 31: Effect of Inhibitors Cytochalasin B and Colcemid on Contraction of Collagen Lattices By Platelets The effects of the inhibitors cytochalasin B and colcemid on the capacity of platelets to contract hydrated collagen lattices was determined following the general procedures of Example 29 except as follows.

Figure 12:
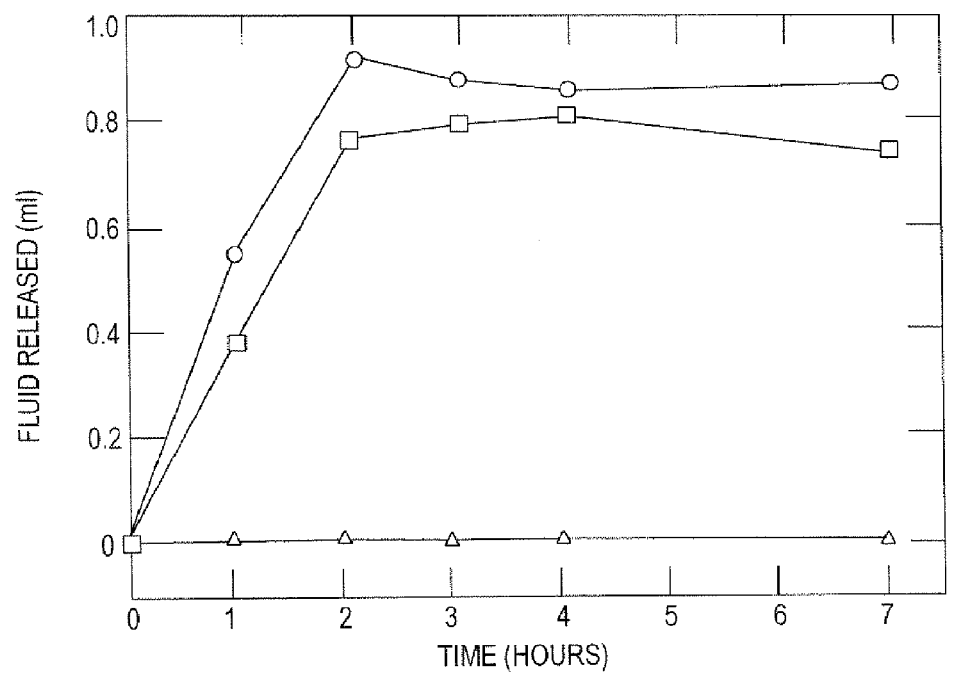

Cytochalasin B (Sigma Chemicals) and colcemid (CIBA Pharmaceutical Company) were added directly to the concentrated DMEM medium to give final concentrations in the 5 ml lattice volume of 10 .mu.g/ml and 0.5 .mu.g/ml, respectively. Data obtained are plotted in FIG. 12.

As can be seen, lattices cast with platelets in the presence of cytochalasin B failed to contract. Colcemid, on the other hand, had no apparent effect on lattice contraction; this was expected since Colcemid is known to have no effect on the ability of human platelets to contract fibrin clots. Cytochalasin B, on the other hand, stabilizes the discoid shape of platelets and prevents pseudopod formation.

Example 32: Rabbit Graft

Tissue-equivalents formed from hydrated collagen lattices contracted by platelets and suitable for grafting to the ears of rabbits were prepared as follows. Platelets were collected from 10 ml of rabbit blood taken from the potential graft recipient by heart puncture, and concentrated by differential centrifugation as described in Example 29. Rabbit platelet gels were cast, also following the procedures of Example 29. After contraction, the lattices were seeded with epidermal cells derived from a biopsy from the same rabbit following the procedures of Example 28.

The anesthetized rabbit was prepared for grafting by clipping the hair over the graft site. The graft bed was outlined, and tattoo marks were placed just outside the periphery of the outline. The site was washed with 70% ethanol and all tissue down to the fascia overlying the cartilage was removed. The tissue-equivalent was freed from the dish and placed on the graft bed with the edges of the graft slightly overlapping the edges of the graft bed. The graft was overlaid with tulle gras prepared by impregnating Telfa pads with vaseline. Telfa pads soaked in Earle's salt solution were placed over the tulle gras. A foam pad was used in the ear to hold it in shape and the ear was bandaged with three-inch Elastoplast. To prevent the rabbit from removing the bandage, both ears were taped together with three-inch Elastoplast. The bandages were removed seven days after grafting. The rabbit was fitted with an Elizabethan collar to prevent scratching for another two days.

The grafted region together with a border of normal skin was excised as a single piece from the rabbit ear and immersed in 10% formalin in 0.03 M phosphate buffer. The skin was fixed overnight, rinsed with distilled water, dehydrated in ethanol, cleaned in amyl acetate followed by toluene and embedded in Paraplast t. Seven micron sections were cut using a rotary microtome and these were stained with hematoxylin and eosin.

Grafts were accepted and inhibited wound contraction in all experiments. Grossly, the grafts appeared whiter than surrounding skin, the surface being somewhat scaly and lacking hair. Even after six weeks, a small centrally located scab remained.

A graft which had been in place for six weeks was examined histologically in part to determine the degree to which the graft was infiltrated by fibroblasts from surrounding tissue. The density of fibroblasts in the graft was considerably greater than that of the adjacent tissue. The graft was distinguished from surrounding tissue by the reduced level of birefringence noted viewed under a light microscope. Vascularization in the graft appeared to be greater than in adjacent tissue. The graft was further distinguished from surrounding tissue by the absence of secondary derivatives, that is, hair follicles and sebaceous glands. The epidermal covering of the graft was markedly hypertrophied.

Example 33: In Vivo Studies of Rejection of Skin-Equivalent in Rats Formation of Skin-Equivalent Small pieces of skin were removed from the backs of female Fischer-344 rats (Charles River Breeding Labs.). These biopsies were trimmed of extraneous tissue, cut into 2-3 mm.sup.3 pieces and dried down onto the surface of Lux tissue culture dishes. The fibroblasts which grew out of the biopsies were cultured in Dulbecco's modification of Eagle's Minimal Essential Medium (DMEM) supplemented with 10 percent fetal calf serum, penicillin, streptomyccin and fungizone (Flow Laboratories) in a 10 percent C0.sub.2 atmosphere at 37° C.

Collagen lattices were prepared following the procedures of Example 28. Briefly, 2-8.times.10.sup.5 fibroblast cells were combined in a 100 mm plastic dish with concentrated DMEM plus 10 percent fetal calf serum, antibiotics and 6 mg of rat tail collagen in a 1:1000 dilution of acetic acid in water. Within a week the fibroblasts had contracted the collagen lattice and a suspension of epidermal cells dissociated from a fresh biopsy was layered onto the surface of the lattice. Cholera toxin at 10.sup.-10 M, epidermal growth factor at 20 .mu.g/ml and hydrocortisone at 0.4 .mu.g/ml were added to the medium to promote the growth of epidermal cells and the dishes were moved to a 5 percent CO.sub.2 atmosphere. Within a week the epidermal cells formed a confluent sheet on the surface of the collagen lattice and the skin equivalent was ready for grafting.

To test allografts, lattices were prepared with cells from the female Sprague-Dawley rats and implanted onto male Fisher rats.

Grafting Procedure

Male Fischer rats weighing approximately 350-400 g. were anesthetized with sodium phenobarbital. A graft bed approximately the same size as the lattice was prepared by removing the full thickness of the skin from the back of each animal. The lattice was placed in the wound and covered with a vaseline-impregnated Telfa pad and a Telfa pad soaked in Earle's salt Solution. These bandages were covered by wrapping the body with several layers of Elastoplast. At time intervals ranging from nine days to thirteen months after the graft was originally applied, the animals were again anesthetized and the entire graft was excised. Half of the graft was fixed in phosphate-buffered formalin, dehydrated in ethanol, and embedded in paraffin. A central portion of the other half of the graft was trimmed of underlying fat tissue, cut into 2-3 mm.sup.3 pieces and placed in tissue culture to allow the resident fibroblasts to grow out.

Preparation of the Karyotypes

The population of fibroblasts which grew out of the grafts was subcultured to obtain three to six T-150 flasks of rapidly dividing cells. The fibroblasts were treated with colchicine at 2 .mu.g/ml for four hours, shaken off the flasks, swollen in hypotonic medium (1 part DMEM to 3 parts distilled H.sub.2 O), air-dried onto glass slides, and stained with aceto-orcein. Twenty to thirty complete chromosomal spreads for each time point were photographed and kayrotypes prepared to determine the proportion of female cells in the total population of fibroblasts.

Drafts with Sprague-Dawley female cells were received and retained by male Fisher hosts as determined by the presence of female cells in the graft 1-2 months afterward.

Example 34: Preparation of Skin Tissue Equivalent Test Systems

A. An apparatus similar to that shown in FIG. 16. was used in conducting the work described hereinafter. The cover is removed for conducting operation but is otherwise kept in place to maintain sterility. Pertinent information regarding the apparatus is listed below:

| Outer container 10: |
| --- |
| diameter 38 mm |
| capacity 35 ml |
| Inner container 20: |
| diameter 24 mm |
| capacity 4 ml |
| Permeable member 24: |
| Polycarbonate membrane from Nuclepore, pore size 3 .mu., thickness 5 .mu.. |

B. An acellular, hydrated collagen gel was formed on the permeable member 24 as follows:

| (1) Premix: | |
| --- | --- |
| 10X MEM | 16.2 ml |
| L-glutamine (200 mM) | 1.6 ml |
| gentamycin (50 mg/ml) | 0.2 ml |
| Fetal bovine serum | 18.0 ml |
| Sodium bicarbonate (71.2 mg/ml) | 5.0 ml |

The stock solutions were mixed at 37° C., combining in the above sequence, and stored at 4° C. for approximately 30 min. in 50 ml. tube (not gassed). (2) 27.8 g of a 1 mg/ml collagen solution (extracted by acid from calf common digital extensor tendon) in 0.05% v/v acetic acid, was weighed out into a 50 ml tube and stored 4° C. for 30 min. (3) 8.2 ml of the pre-mix described above and 4 ml of DMEM complete (containing 10% FBS, 4 mM L-glutamine, 50 .mu.g/ml gentamycin) was added (and 1 ml aliquots pipetted into the inner container 20 and allowed to gel in a hood.

C. Tissue equivalents were cast with human dermal fibroblasts and seeded with human epidermal (epithelial) cells as described below. A general description of procedures and reagents may also be found in the patents and copending application Ser. No. 07/361,041, filed Jun. 5, 1989.

(1) Casting Mixture:

8.2 ml of the pre-mix described above was added to 27.8 g of a 1 mg/ml collagen solution in 0.05% v/v acetic acid, as described in step A(2) above, and 4 ml of human dermal fibroblasts (2.5.times.10.sup.5 cells/ml) were combined. 3 ml aliquots were pipetted into the container 20 over the acellular, hydrated collagen gel formed in step B(2) above and allowed to gel. 4.5 ml DMEM complete was added to the outside container 20 and then incubated at 36° C./10% CO.sub.2 typically for 4-8 days.

The following medium was used:

| Components | mSBM |
| --- | --- |
| Hydrocortisone | 1.1 .mu.M |
| Insulin | 5 .mu.g/ml |
| Transferrrin | 5 .mu.g/ml |
| Triiodothyronine | 20 pM |
| Ethanolamine | 1 .times. 10.sup.−4 M |
| O-phosphorylethanolamine | 1 .times. 10.sup.−4 M |
| Adenine | 0.18 mM |
| Progesterone | 2 .times. 10.sup.−9 M |
| Selenium | 5.26 .times. 10.sup.−8 M |
| Bovine Serum | 0.3% |
| Epidermal Growth Factor | 10 ng/ml |
| Calcium Free DMEM | 75% |
| Ham's F-12 | 25% |

Two other media used were identical with mSBM except as noted below:

| | cSBM | mainSBM |
| --- | --- | --- |
| Progesterone | 0 | 0 |
| Bovine Serum | 2.0% | 1% |
| Epidermal Growth Factor | 1 ng/ml | 1 ng/ml |
| Calcium Free DMEM | 50% | 50% |
| Ham's F-12 | 50% | 50% |

In some instances calcium chloride was added to the media at 1.8 mM. This is indicated as medium plus calcium, e.g., mSBM plus calcium.

D. Epidermalization was initiated at 6 days after casting the tissue equivalent.

(1) Epidermalizing

The medium of step C above was removed from both the inside 20 and outside 10 containers. A 50 .mu.l suspension of human epidermal cells (3.33.times.10.sup.6 cells/ml) was placed on the tissue equivalent formed above in step C above. The container was then incubated at 36° C. and 10% $CO_2$ for 4 hours. 12.0 ml of mSBM was then added to the outside chamber and 4 ml to the well. The apparatus was then returned to the same incubator.

(2) Differentiating

At 2 days post epidermalization the medium was removed and replaced with mSBM plus calcium.

(3) Airlifting

At 5 days post epidermalization, the following procedure was performed: Medium was removed from inside and outside chambers. The inner container 20 was removed and two volumes cSBM plus calcium soaked cotton pads were positioned in the bottom of the outer chamber 10 and 9.0 ml of cSBM plus calcium added. The inner container 20 was then replaced and the apparatus incubated at 35.5° C. and 10% $CO_2$.

(4) Maintaining

Every 4 days the medium was removed and replaced with fresh main SBM plus calcium.

Example 35: Preparation of Test Systems Incorporating Agarose

A 2% agarose solution in water was sterilized by autoclaving, cooled to 40° C. and mixed with an equal volume of 2 concentrated main SBM. The absorbent cotton pads were removed and 13 ml of the mixture was poured into the outer area 14, allowed to set at 36° C. (10% $CO_2$) and the apparatus returned to the incubator for storage prior to shipment.

It is understood that the examples and embodiments described herein are for illustrative purposes only, and that various modifications or changes in light thereof that will be suggested to persons skilled in the art are to be included in the spirit and purview of this application and the scope of the approved claims.

Example 36: Efficacy of a Cultured Tissue Construct for Treatment of Recessed Oral Gingiva The primary objective was to determine whether the cultured tissue construct could provide a functional zone of attached gingiva comparable to free autogenous graft.

During this study, up to 25 subjects were enrolled. Subjects were aged at least 18-70. The first three subjects were used to determine surgical and material handling techniques, and were not included in the statistical analysis. Subsequent patients were enrolled until these three patients had completed four weeks of follow up. The subjects enrolled had at least two non-adjacent teeth with an insufficient zone of attached gingival which required tissue grafting. The two selected tooth must have been located in contralateral quadrants. Root coverage was not indicated or desired at the time of grafting. The subjects were treated with either the cultured tissue construct of the invention or with a free autogenous graft. The grafts were evaluated clinically to determine the change in the attached gingival and on at least three subjects, a small biopsy was taken to allow histologic evaluation and comparison of both grafts. Secondary efficacy variable were the changes from baseline in width of keratinized tissue, recession depth, inflammation score, color or texture match of the grafted tissue to the adjacent tissue, resistance to oral muscle pull, clinical attachment level, probing depth and subject discomfort.

The study utilized a randomized, controlled treatment comparison between subjects. Assessment of the amount and the quality of attached gingival generated through the cultured tissue construct and free autogenous grafts had occurred at one week postoperatively, and at months 1, 3 and 6. Primary end point had occurred at month 6. All postoperative evaluations were performed by the research coordinator who was blinded to the surgical procedures performed. Color, texture, inflammation and resistance to muscle pull was scored independently by a calibrate research coordinator.

Although the foregoing invention has been described in some detail by way of illustration and Examples for purposes of clarity and understanding, it will be obvious to one of skill in the art that certain changes and modifications may be practiced within the scope of the appended claims.

I claim:

1. A method for treating recessed oral gingiva in a subject, said method comprising: grafting a contracted cultured tissue construct to an oral tissue of the subject, wherein said contracted cultured tissue construct comprises a gel mixture of a collagen solution and a contractile agent, wherein the contractile agent comprises cultured dermal fibroblast cells derived from human neonate male foreskin, wherein the contracted cultured tissue construct does not comprise oral mucosal cells or autologous cells, and wherein the treatment of the recessed oral gingiva with the contracted cultured tissue construct in said subject results in a functional zone of attached gingiva that is comparable to the functional zone produced from grafting a free autogenous graft to an oral tissue.

* * * * *